United States Patent
Kuijpers et al.

(10) Patent No.: US 9,017,971 B2
(45) Date of Patent: Apr. 28, 2015

(54) MEANS AND METHODS FOR INVESTIGATING NUCLEIC ACID SEQUENCES

(75) Inventors: Taco Willem Kuijpers, Amstelveen (NL); Martin de Boer, Blokker (NL)

(73) Assignee: Stichting Sanquin Bloedvoorziening, Amsterdam (NL)

( * ) Notice: Subject to any disclaimer, the term of this patent is extended or adjusted under 35 U.S.C. 154(b) by 0 days.

(21) Appl. No.: 12/998,595

(22) PCT Filed: Nov. 5, 2009

(86) PCT No.: PCT/NL2009/050669
§ 371 (c)(1),
(2), (4) Date: Jul. 26, 2011

(87) PCT Pub. No.: WO2010/053363
PCT Pub. Date: May 14, 2010

(65) Prior Publication Data
US 2012/0003633 A1    Jan. 5, 2012

(51) Int. Cl.
C12P 19/34    (2006.01)
C12Q 1/68     (2006.01)
C07H 21/02    (2006.01)
C07H 21/04    (2006.01)
C07H 21/00    (2006.01)

(52) U.S. Cl.
CPC ............ *C12Q 1/6876* (2013.01); *C12Q 1/6858* (2013.01)

(58) Field of Classification Search
USPC ............... 435/6.1, 6.11, 6.12, 91.1, 91.2, 183; 436/94, 501; 536/23.1, 24.3, 24.33, 536/25.3
See application file for complete search history.

(56) References Cited

U.S. PATENT DOCUMENTS

| | | | |
|---|---|---|---|
| 6,033,854 A | * | 3/2000 | Kurnit et al. .................. 435/6.12 |
| 2003/0108913 A1 | * | 6/2003 | Schouten .......................... 435/6 |
| 2007/0092883 A1 | | 4/2007 | Schouten et al. |

FOREIGN PATENT DOCUMENTS

| | | |
|---|---|---|
| EP | 1 130 113 A1 | 9/2001 |
| WO | 0161033 A2 | 8/2001 |
| WO | 03/048732 A2 | 6/2003 |
| WO | 2007/041067 A2 | 4/2007 |

OTHER PUBLICATIONS

Hsu et al., "Killer Ig-Like Receptor Haplotype Analysis by Gene Content: Evidence for Genomic Diversity with a Minimum of Six Basic Framework Haplotypes, Each with Multiple Subsets" J Immunol; 169; 2002; 5118-5129.
Brown "Genetics and the pathogenesis of ankylosing spondylitis" Curr Opin Rheumatol; 21; 2009; 318-323.
Chan et al. "Expansion and Enhanced Survival of Natural Killer Cells Expressing the Killer Immunoglobulin-Like Receptor KIR3DL2 in Spondylarthritis" Arthritis & Rheumatism; vol. 52; No. 11; Nov. 2005; 3586-3595.
Cook et al. "A Multi-Laboratory Characterization of the KIR Genotypes of 10th International Histocompatibility Workshop Cell Lines" Human Immunology; 64; 2003; 567-571.

(Continued)

*Primary Examiner* — Frank Lu
(74) *Attorney, Agent, or Firm* — Nanda P. B. A. Kumar; Reed Smith LLP

(57) ABSTRACT

The invention provides improved methods for investigating nucleic acid sequences, wherein at least one additional probe is used which is specific for a (pseudo)gene variant of a target nucleic acid.

13 Claims, 40 Drawing Sheets

(56) References Cited

OTHER PUBLICATIONS

Crum et al. "Development of a PCR-SSOP approach capable of defining the natural killer cell inhibitory receptor (KIR) gene sequence repertoires" Tissue Antigens; 56; 2000; 313-326.
Du et al. "Receptor-ligand analyses define minimal killer cell Ig-like receptor (KIR) in humans" Immunogenetics; 59; 2007; 1-15.
Gomez-Lozano et al. "Some human KIR haplotypes contain two KIR2DL5 genes: KIR2DL5A and KIR2DL5B" Immunogenetics; 54; 2002; 314-319.
Gomez-Lozano et al. "The silent KIR3DP1 gene (CD158c) is transcribed and might encode a secreted receptor in a minority of humans, in whom the KIR3DP1, KIR2DL4 and KIR3DL1/KIR3DS1 genes are duplicated" Eur. J. Immunol.; 35; 2005; 16-24.
Hollenbach et al. "Susceptibility to Crohn's Disease is Mediated by KIR2DL2/KR2DL3 Heterozygosity and the HLA-C Ligand" Immunogenetics; 61 (10); Oct. 2009; 663.
Hsu et al. "The killer cell immunoglobulin-like receptor (KIR) genomic region: gene-order, haplotypes and alleic polymorphism" Immunological Reviews; vol. 190; 2002; 40-52.
Khakoo et al. "HLA and NK Cell Inhibitory Receptor Genes in Resolving Hepatitis C Virus Infection" Science; vol. 305; Aug. 6, 2004; 872-874.
Li et al. "Genetic Control of Variegated KIR Gene Expression: Polymorphisms of the Bi-Directional KIR3DL1 Promoter Are Associated with Distinct Frequencies of Gene Expression" PLOS Genetics; vol. 4, Issue 11; Nov. 2008; e1000254.
Marsh et al. "Killer-cell Immunoglobulin-like Receptor (KIR) Nomenclature Report, 2002" Human Immunology; 64; 2003; 648-654.
Martin et al. "Innate partnership of HLA-B and KIR3DL1 subtypes against HIV-1" Nature Genetics; vol. 39; No. 6; Jun. 2007; 733-740.
Middleton et al. "KIR genes" Transplant Immunology; 14; 2005; 135-142.
Parham et al. "Alloreactive Killer Cells: Hindrance and Help for Haematopoietic Transplants" Nature; vol. 3; Feb. 2003; 108-122.
Shilling et al. "Allelic Polymorphism Synergizes with Variable Gene Content to Individualize Human KIR Genotype" J Immunol; 168; 2002; 2307-2315.
Zhang et al. "Killer cell immunoglobulin-like receptor gene polymorphisms in patients with leukemia: Possible association with susceptibility to the disease" Leukemia Research; 34; 2010; 55-58.
Sun et al. "Development of a multiplex PCR-SSP method for Killer-cell immunoglobulin-like receptor genotyping" Tissue Antigens; 64; 2004; 462-468.
Trowsdale et al. "The genomic context of natural killer receptor extended gene families" Immunological Reviews; vol. 181; 2001; 20-38.
Uhrberg et al. "Human Diversity in Killer Cell Inhibitory Receptor Genes" Immunity; vol. 7; Dec. 1997; 753-763.
Uhrberg "The KIR gene family: life in the fast lane of evolution" Eur. J. Immunol.; 35; 2005; 10-15.
Vilches et al. "KIR: Diverse, Rapidly Evolving Receptors of Innate and Adaptive Immunity" Annu. Rev. Immunol.; 20; 2002; 217-251.
Williams et al. "Multiple Copies of KIR 3 DL/S1 and KIR 2DL4 Genes Identified in a Number of Individuals" Human Immunology; 64; 2003; 729-732.
Yen et al. "Major Histocompatibility Complex Class I—recognizing Receptors Are Disease Risk Genes in Rheumatoid Arthritis" J. Exp. Med.; vol. 193, No. 10; May 21, 2001; 1159-1167.
Vilches et al., "Facilitation of KIR genotyping by a PCR-SSP method that amplifies short DNA fragments" Tissue Antigens (2007) 70, 415-422, XP-002533250.
Giebel et al., "Association of KIR2DS4 and its variant K1R1D with leukemia" Leukemia (2008) 22, 2129-2130, XP-002569478.
Majorczyk et al., "Associations of killer cell immunoglobulin-like receptor genes with complications of rheumatoid arthritis" Genes and Immunity (2007) 8, 678-683, XP-002569479.
Jiao et al., "Polymorphisms of KIRs Gene and HLA-C Alleles in Patients with Ankylosing Spondylitis: Possible Association with Susceptibility to the Disease" J Clin Immunol (2008) 28: 343-349.
Verheyden et al., "Susceptibility to myeloid and lymphoid leukemia is mediated by distinct inhibitory KIR-HLA ligand interactions" Leukemia (2006) 20, 1437-1438, XP-002569480.
Carrington et al. "The KIR Gene Cluster" National Center for Biotechnology Information (US); Bookshelf ID: NBK10135; May 28, 2003; 1-48.
Schouten et al. "Relative quantification of 40 nucleic acid sequences by multiplex ligation-dependent probe amplification" Nucleic Acids Research; vol. 30, No. 12; 2002; e57.

\* cited by examiner

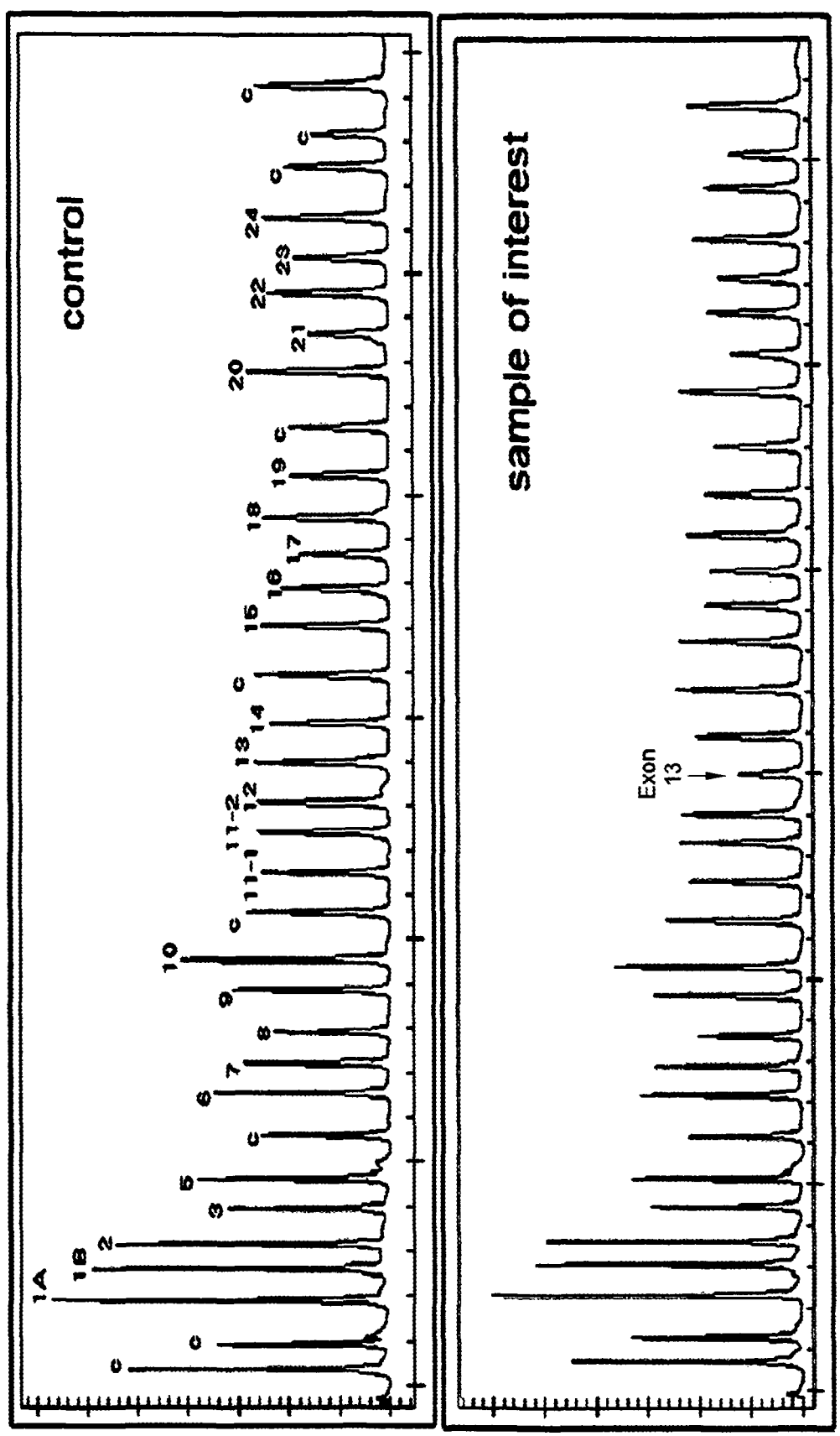
Fig. 1A, condt.

Degenerate bases

| IUB Code | Definition |
|---|---|
| R | A or G |
| Y | C or T |
| K | G or T |
| M | A or C |
| S | G or C |
| W | A or T |
| B | C or G or T |
| D | A or G or T |
| H | A or C or T |
| V | A or C or G |
| N | A or G or C or T |

Fig. 2

| code | Probe | Size [bp] | Probe Part | Size [bp] | SEQ ID NO | Sequence |
|---|---|---|---|---|---|---|
| 420A | 2DL2 rev | 96 | Left | 48 | 19 | 5'-GGGTTCCCTAAGGGTTGGACTGACCTTGGGCCCTGCAGAGAACCTACA-3' |
| 420B | ex 5 P3 | | Right | 48 | 20 | 5'PO4-TTCATGGGCCTCCCCCTCCTGGATGTCTAGATTGGATCTTGCTGGCAC-3' |
| 512A | 3DL3 | 100 | Left | 50 | 21 | 5'-GGGTTCCCTAAGGGTTGGATAGATGCTTCCGCTCTTCCGTGCCCTGCCC-3' |
| 512B | ex 5-6-7 | | Right | 50 | 22 | 5'PO4-CACGCGTGGTCAGAGCCGAGTGACCCGTCTAGATTGGATCTTGCTGGCAC-3' |
| 540A | 2DS3 P6 | 108 | Left | 54 | 23 | 5'-GGGTTCCCTAAGGGTTGGAGCCACATCACGATGTCAGAGGGTCACTGGGAGCTGAA-3' |
| 540B | ex 4 rev | | Right | 54 | 24 | 5'PO4-AACTGATAGGGGAGTGGAATGAGGAACAGAGACGTCTAGATTGGATCTTGCTGGCAC-3' |
| 404A | 3DL2 | 112 | Left | 56 | 25 | 5'-GGGTTCCCTAAGGGTTGGAATCCACCCTAAGGTTTGGGGAAGGACTCACCCATGA-3' |
| 404B | ex 2 | | Right | 56 | 26 | 5'PO4-GTGGCCAGGCCCCTGCAGCAAGAAGAACCTGTCTAGATTGGATCTTGCTGGCGC-3' |
| 405A | 2DP1 | 121 | Left | 65 | 27 | 5'-GGGTTCCCTAAGGGTTGGACCCAAGTGGTCAGGACACATGTGATTCTTCGGGTGCTGGATCTTGCTGGCGC-3' |
| 405B | ex 3 | | Right | 56 | 28 | 5'PO4-TGTGGTGCCTCCAGGACATGTGATTCTTGGGGTGCTGGGTGCTGACCACCAGTGAGGA-3' |
| 406A | 3DP1 | 125 | Left | 66 | 29 | 5'-GGGTTCCCTAAGGGTTGGAACCATGACCAGGGGTGTCCGTCTAGTGCCTGTCAGAAGAGTGCTCAAACATGACATCC-3' |
| 406B | ex 3 | | Right | 59 | 30 | 5'PO4-AGTGTGGGTGTGAAACCCGACATCGTAGGTCCCGTCTGTCAGAAGAAGTGCTCAAACATGACATCC-3' |
| 504A | 2DS4 rev | 137 | Left | 61 | 31 | 5'-GGGTTCCCTAAGGGTTGGAGACCAACATTGCAGGATGACTGCTCTTCTTGATTCACCAGGTGACCTGGGAGTCTAGATTGGATCTTG |
| 504B | ex 4 | | Right | 76 | 32 | 5'PO4-GACCAACATTGCAGGATGACTGCTCTTCTTGATTCACCAGGTGACCTGGGAGTCTAGATTGGATCTTGCTGGCAC-3' |
| 408A | 2DL5 | 142 | Left | 57 | 33 | 5'-GGGTTCCCTAAGGGTTGGACTCAGGTGAGGGGAGCTGTGACAAGGAAGAACCTCC-3' |
| 408B | ex 3-5 | | Middle | 32 | 34 | 5'PO4-CTGAGGAAACCTTCACTCTCAGCCAGGTCTATT-3' |
| 408C | | | Right | 53 | 35 | 5'PO4-TGGAAACCTTCACTCTCAGCCCAGGCTGTCTTATCTAGGATACTCCAAGGCCAATTCTCTAGATTGGATCTTGCTGGCGC-3' |
| 514A | 3DL1 | 149 | Left | 74 | 36 | 5'-GGGTTCCCTAAGGGTTGGACCTGTCTTAGGATACTCCAAGGCCAATTCTCCATCGGTCCCATGATGCT-3' |
| 514B | ex 4 | | Right | 75 | 37 | 5'PO4-TGCCCTTGCAGGGACCTACAGATGCTACGGTTCTGTCTCTCGTCAGACGTGTCTAGATTGGATCTTGCT GGCAC-3' |
| 507A | 2DL5A rev | 165 | Left | 66 | 38 | 5'-GGGTTCCCTAAGGGTTGGACGGGGCGGGGCTGCCTGTCGCACCGGCAGCACCATGTGCTCGCTCATGGTCA-3' |
| 507B | ex/InTr1 | | Middle | 32 | 39 | 5'PO4-TCAGCATGGCGTGTTGGTGGTGAGTCCTGGAAAA-3 |
| 507C | | | Right | 67 | 40 | 5'PO4-TGACATGAGCCGACACATGGTGCTGCCGGTGCAGACGGGCAGGTTGGTCTAGATTGGATCTTGCTGGCAC-3' |
| 419A | 2DL4 | 170 | Left | 59 | 41 | 5'-GGGTTCCCTAAGGGTTGGACCTGCTTCAGAACCTGGTAACCTGGTGCCTCCTCCCTCCAGGACTCACCCAAG-3' |
| 419B | ex/InTr1 | | Middle | 54 | 42 | 5'PO4-TCTGCAGGCCCATAGTGAACCTGGTGACATGGAGCATGATGACCGTGGGTGACATGGAGACTCACCCAAG-3' |
| 419C | | | Right | 57 | 43 | 5'PO4-ACATGCCAGGATGATGACCGTGGGTGACATGGAGATCTAGATTGGATCTTGCTGGCAC-3' |

Fig. 3A

| | | | | |
|---|---|---|---|---|
| 528A | | | Left | 67 | 44 | 5'-GGGTTCCCTAAGGGTTGGACCGAGTAAACGGAAAATTTCATCTGCACAGAGAGGGACGTTTAAC-3' |
| 528B | 185 | | Middle | 47 | 45 | 5'-PO4-CACACTTGCGCCTCATTGGAGAGCACATTGATGGGTCTCCAAGGG-3' |
| 528C | | | Right | 71 | 46 | 5'-PO4-CAACTTCCAATCGGTCGCATGACAAGACCTGGCATAGCGAATACGTCTAGATTGGATCTTGCTGGCAC-3' |
| 413A | | 189 | Left | 72 | 47 | 5'-GGGTTCCCTAAGGGTTGGACTACCCCATCGCTCTTCATGCTGGATCATTCACTCTGCATCCAATGACAATG-3' |
| 413B | | | Middle | 64 | 48 | 5'-PO4-AGAAGAAAAGTCTGGACACTGGAGTGAGTAACAGAAACCGTAGTCTAGATTGATCTTGCTGGCAC-3' |
| 413C | | | Right | 53 | 49 | 5'-PO4-CTGATAGGGGAGTGAGTAACAGAAACCGTAGTAACCGCATGAAAAGGCTGTTCCAGAATATTATGTTGTAGAGCTCAGGGA |
| 416A | 195 | | Left | 78 | 50 | 5'-GGGTTCCCTAAGGGTTGGACACAGGGCCCATGAAAAGGCTGTTCCAGAATATTATGTTGTAGAGCTCAGGGA CAGGCA-3' |
| 416B | | | Middle | 67 | 51 | 5'-PO4-CCCCATCTCCTTTTACAGAGAAGTGTAAACCCAAGATGAAGTTGTAAACCAAGATAAGAATGACACTGAAGAATCACATA |
| 416C | | | Right | 50 | 52 | 5'-PO4-TCCTGGAGGCACCAGGGGTTGGACTGCACAGTTGGATCACTGCGTTTCACACAGAAAAAATCACTCGCCCTT-3' |
| 415A | 213 | | Left | 75 | 53 | 5'-GGGTTCCCTAAGGGTTGGACTGCACAGTTGGATCACTGCGTTTCACACAGAAAAAATCACTCGCCCTT-3' |
| 415B | | | Middle | 69 | 54 | 5'-PO4-CTCAGAGGGCCCAAGACACCCCAACAGACATCATCGTCGTACAGGCCTTGTCTAGATTGATCTTGCTGGCGC-3' |
| 415C | | | Right | 69 | 55 | 5'-PO4-GATCCAAAGTGTCTCTGCCAGTCACACACAGTGAGGAAAATGCTGAGTGAGGGAGGGTGCTCAC |
| 418A | 218 | | Left | 81 | 56 | 5'-GGGTTCCCTAAGGGTTGGACTTGTTCATCAGAATGCTGAGTGAGGGAGGGTGCTCAC ATTTTC-3' |
| 418B | | | Middle | 64 | 57 | 5'-PO4-AGGACTCTTTGGGAATAACACTAGCCACGAGGCTGGGCGGAGGAGCACCTACCTCGTGTTCAC-3' |
| 418C | | | Right | 73 | 58 | 5'-PO4-TTCTGTTCCCTGCCAGGCTCTTGGTCCATTACAGCCAGCATCGTAGGAAGACGTCTAGATTGATCTTGCTGGCGC-3' |

Fig. 3A, contd.

| Code | Probe | Size [bp] | Probe Part | Size [bp] | SEQ ID NO | Sequence |
|---|---|---|---|---|---|---|
| 544A | 2DS2 | 100 | Left | 50 | 83 | 5'-GGGTTCCCTAAGGGTTGGACCGGCCGAGCACCCAGGGTCTCTCTTCCC-3' |
| 544B | intron 2/3 | | Right | 50 | 84 | 5'-PO4-AGTTTATGAGAGACTCCCTGACAGGAGTCTAGATTGCTGGCAC-3' |
| 537A | 2DL5 P4 | 108 | Left | 54 | 99 | 5'-GGGTTCCCTAAGGGTTGGACCGACCCGAGGCTTCGGCTCTCCATGACTC-3' |
| 537B | exon 5 | | Right | 54 | 101 | 5'-PO4-ACCCTATGAGTGGTCAGAGCCGAGTGACCCGTCTAGATTGCTGGCAC-3' |
| 513D | 2DS3 | 112 | Left | 52 | 105 | 5'-GGGTTCCCTAAGGGTTGGACGGGCCAGAAGTCGGCCTGAGCATCGTAGGTTCCTCCT-3' |
| 513B | | | Right | 60 | 106 | 5'-PO4-TGGGTGGCAGGGCCCAGAAGAAAGTCGGCCTGAGCCTGAAGATAGAGGAGGAGTGCCACATC-3' |
| 518A | 3DP1 | 121 | Left | 61 | 91 | 5'-GGGTTCCCTAAGGGTTGGACGCTGAGGCCTGGAAGGAATAGAGGGTCTAGATTGCTGGCAC-3' |
| 518B | | | Right | 60 | 92 | 5'-PO4-CTCCTCTAAGGTGGCGCCTCCTTCTCCCCAGGTGTCGTTGGTTACTCACTCCCC-3' |
| 542A | 2DP1 | 125 | Left | 60 | 87 | 5'-GGGTTCCCTAAGGGTTGGACTCAGCTCCCAGTGACCCTCTGGACATCGTCATGTCTAGATTGCTGGCAC-3' |
| 542B | exon 4 | | Right | 65 | 88 | 5'-PO4-CATCAGTTGTCAGCTCCCAGTGACCCTCTGGACATCGTCATGTCTAGATTGCTGGCAC-3' |
| 524A | 2DS4 | 137 | Left | 66 | 159 | 5'-GGGTTCCCTAAGGGTTGGACGATGGCAGGGCCCAGAGGAAAGTCGGCCTGGAAGTTCCGTTGAT-3' |
| 524B | | | Right | 71 | 160 | 5'-PO4-GCTGCGCACTGCAGGGAGCCTACGTTCCCCCTTCCCTTGGTCTAGATTGGATCTTGCTG GCAC-3' |
| 409A | 3DL1 | 149 | Left | 60 | 96 | 5'-GGGTTCCCTAAGGGTTGGACTCAGCTCAGGTCAGTCAGCTATGAGGGGAGCTATGACAAGGAAGAACCT-3' |
| 409B | | | Middle | 34 | 97 | 5'-PO4-CCCTGAGGAAAACCTTCCTCAGCCCAGGTCC-3' |
| 409C | | | Right | 55 | 98 | 5'-PO4-ATATGAGAATGAGAAGGTTCCCTAAGGGTCTAGATTGGATCTTGCTGGCAC-3' |
| 506A | 3DL3 | 154 | Left | 54 | 76 | 5'-PO4- GGGTTCCCTTGACAAGGGTGAGAGGCAGGTCACTGGGAGCGAGAACTCATAGGGTA-3' |
| 506B | | | Middle | 48 | 77 | 5'-PO4- CGACCACGATGTCACAGAGAACAAAGCATCTGTAGTCTAGATTGGATCTTGCTGGCAC-3' |
| 506C | | | Right | 52 | 78 | 5'-PO4-AGTGAGTTCCCTAAGGGTTGGACCTCTCCAGCAGGATGATCCATCCCGCACTCCCTCCTCTATTCC-3' |
| 507A | 2DL5A rev | 165 | Left | 66 | 161 | 5'-GGGTTCCCTAAGGGTTGGACCTCTCCAGCAGGATGATCCATCCCGCACTCCCTCCTCTATTCC-3' |
| 507B | ex/intr1 | | Middle | 32 | 162 | 5'-PO4-TTTCCAGGACTCACCAACACGCCATGCTGA-3' |
| 507C | | | Right | 67 | 40 | 5'-PO4-TGACCATGAGCGGACCATGGACCTGCAGTTGGTCTAGGAGTTGGTCTAGATTGGATCTTGCTGGCAC-3' |
| 538A | 3DL2 rev | 195 | Left | 70 | 120 | 5'-GGGTTCCCTAAGGGTTGGACCTCACCTGTGACAGAAAACAAGCAGTGGGTCACTTGAGTTTGACCACCACGCA-3' |
| 538B | ex/int 5 | | Middle | 60 | 121 | 5'-PO4-CGGGTTTTCCTCACCTGTGACAAGAGCCGAAGCATCTGTAGTTCCCTGTCTAGATGGGACAGAACA-3' |
| 538C | | | Right | 65 | 122 | 5'-PO4-GGGCAGGGCACGGAAAGAGCCGAAGCATCTGTAGTTCCCTGTCTAGATTGGATCTTGCTGGCAC-3' |

Fig. 3B

| | | | | | |
|---|---|---|---|---|---|
| 417A | 2DL3 | 213 | Left | 75 | 5'-GGGTTCCCTAAGGGTTGGACTGCTGCCTTGGGCCAGGGACCATCCTGTCTGTGAGGAACACACCTGAGTGCTC-3' |
| 417B | ex 7-8 | | Middle | 69 | 5'PO4-CCATCCTGCTTCCCCACATGGCCCTGAGCTCTGCCTCTTCGTGAGACTTACTTTTTTGTTGC-3' |
| 417C | | | Right | 69 | 5'PO4-AGCACCAGCGATGAAGGAGAAGAGGAGGATGAAGAGGATGTCTAGATTGGATCTTGCTGGCAC-3' |
| 517A | 2DL4 | 218 | Left | 73 | 5'-GGGTTCCCTAAGGGTTGGACCCGCTTAGAAGAAGAAATGGGGAGAATCTTGAGCACAGGGAGGGAGGGGC-3' |
| 517B | | | Middle | 68 | 5'-AGCTCAACATACTCCTCTGAGGCGGCCATCCTCTTCTCCCCAAGGTGGTCAGGACAAGCCCTTCTGC-3' |
| 517C | | | Right | 77 | 5'PO4-TCTGCCTGGCCCAGCGCTGTGGCCTCAAGGAGCACGTGACTCTTCGGTGGTCTAGATTGGATCTTGCTGGCAC-3' |

Fig. 3B, contd.

| Probe # | code | Gene | Probe part | Probe length | Total length | SEQ ID NO | 5'- Probe sequence |
|---|---|---|---|---|---|---|---|
| 512 | A | 3DL3 | left | 50 | 100 | 21 | GGGTTCCCTAAGGGTTGGATAGAATGCTTCGGCT |
| 512 | C | 3DL3 | right | 50 | 100 | 59 | CTTCCGTGTGGCCCAYGGATCTAA |
| 415 | D | 2DL3 | left | 70 | 190 | 60 | P-CAYGCCGTGGTTCCTGGCCCAAGTGACCCTAGA |
| 415 | B | 2DL3 | middle | 66 | 190 | 54 | TTGGATCTCCTTCAGATGGAACTTGCACACTCRC |
| 415 | C | 2DL3 | right | 54 | 190 | 55 | GGGTTCCCTAAGGGTTGGACACYRCAAAGTTGCACACTCRC |
| 703 | A | 2DS2 | left | 58 | 147 | 61 | P-CTCAGAAGGCCCAAAGTTTCCTAGCACCCCAAAATGAGCCCT |
| 703 | B | 2DS2 | middle | 30 | 147 | 62 | TCTTGTACCAAAGGCCTTAGATTCCAATTCCAAGGACACCAAC |
| 703 | C | 2DS2 | right | 59 | 147 | 63 | P-GGATCCAAAGGCCTTAGATTCCAAGTCTCTAGAA |
| 420 | A | 2DL2 | left | 48 | 96 | 19 | P-ATCTTGGTGCTCTAAGGGTTGGACTTGCAAAGTTCAGGTCTCTG |
| 420 | B | 2DL2 | right | 48 | 96 | 20 | GGGTTCCCATGGGTTGGACCCTTCAAAGGTTGGTCAGG |
| 405 | A | 2DP1 | left | 65 | 121 | 27 | P-TTTCATCTGCTTAAGGCCTTGGACTCTCCAAAGGCATTCTTTGGTC |
| 405 | B | 2DP1 | right | 56 | 121 | 28 | GGACAAGGTACAATGCCAGGACACAT |
| 413 | A | 2DL1 | left | 72 | 189 | 47 | P-TGTGGTCTAGATCCTCATGGGCTGCACTTCCCATCCTTGCGCC |
| 413 | B | 2DL1 | middle | 64 | 189 | 48 | P-AGAAAGAAATCCAGGAATCCTACCTCATGGAATGACAC |
| 413 | C | 2DL1 | right | 53 | 189 | 49 | P-CTGATAGGAATTGGCTCAGAAACCCTAGTC |

| Probe # | code | Gene | Probe part | Probe length | Total length | SEQ ID NO | 5'- Probe sequence |
|---|---|---|---|---|---|---|---|
| 506 | A | 3DL3 | left | 54 | 154 | 76 | |
| 506 | D | 3DL3 | middle | 48 | 154 | 77 | P- |
| 506 | C | 3DL3 | right | 52 | 154 | 78 | P- |
| 417 | A | 2DL3 | left | 75 | 214 | 80 | |
| 417 | B | 2DL3 | middle | 69 | 214 | 81 | P- |
| 417 | C | 2DL3 | right | 70 | 214 | 82 | P- |
| 544 | A | 2DS2 | left | 50 | 100 | 83 | |
| 544 | B | 2DS2 | right | 50 | 100 | 84 | P- |
| 706 | A | 2DL2 | left | 74 | 145 | 85 | |
| 706 | B | 2DL2 | right | 71 | 145 | 86 | P- |
| 542 | A | 2DP1 | left | 60 | 125 | 87 | |
| 542 | B | 2DP1 | right | 65 | 125 | 88 | P- |

| Probe # | code | Gene | Probe part | Probe length | Total length | SEQ ID NO | 5' | Probe sequence |
|---|---|---|---|---|---|---|---|---|
| 201 | A | Control 2 | left | 45 | 92 | 124 | | GGGTTCCCTAAGGGTTGGATAGAGGGCTCCAGGTTATCCGGGCTC |
| | B | | right | 47 | 92 | 125 | P- | TGCTTCTGCCGCCGTGGATTCAGgggTCTAGATTGGATCTTGCTGGCac |
| 202 | | Control 3 | left | 52 | 104 | 126 | | GGGTTCCCTAAGGGTTGGATTCAGGAGTGATACTTCACAGATCCTGGAGGAA |
| | | | right | 52 | 104 | 127 | P- | AACATCCAGTCCTTAAGGCCAAACTGAgtCTAGATTGGATCTTGCTGGCaC |
| 203 | | Control 4 | left | 58 | 116 | 128 | | GGGTTCCCTAAGGGTTGGACTGGTGAGACCAAGCGCCGTCATGAGACCCGACTGGTG |
| | | | right | 58 | 116 | 129 | P- | GAGATTGACAATGGAAGCAGCTGAGTTTGAGAGTCTAGATTTGCTGGCac |
| 204 | | Control 5 | left | 44 | 130 | 130 | | GGGTTCCCTAAGGGTTGGACCAGGCGTTCTCAGCCTCCGGATGA |
| | | | middle | 41 | 130 | 131 | P- | CACAAATACCAGAGCACAGATTCAAGTGCAATCCATGTATC |
| | | | right | 45 | 130 | 132 | P- | TGTATGGTCATTCTCACCTGTCTAGATTGGATCTTGCTGGCaC |
| 205 | | Control 7 | left | 59 | 160 | 133 | | GGGTTCCCTAAGGGTTGGACGCAGGAGAAGGAATAGCTGTTATAGTTACAGGACAAGCTGTGGAATGGTATAAGAAAG |
| | | | middle | 42 | 160 | 134 | P- | GTATTGAAGAACTGGAAGAACATCCCAAATTAtGATAtATTCACACTCTAGATTGGATCTTGCTGGCaC |
| | | | right | 59 | 160 | 135 | P- | TTGTTTATAGCCATCCAAATTTATGAAccTGCTCCCAGTAGGGTCAGCATCTTGACCAAGTATG |
| 206 | | Control 8 | left | 58 | 175 | 136 | | GGGTTCCCTAAGGGTTGGACTCTGATTCGAGACTTTGAGACGTCCTATCAGCATCCATCATGAAGAAGCTCTTGACCAAGTATG |
| | | | middle | 59 | 175 | 137 | P- | GAGTCAGGCTCTGATTCGAGACTTTGAGACGTCCATCAGCtgTCTAGATTGGATCTTGCTGGCaC |
| | | | right | 58 | 175 | 138 | P- | ACAACCTCTTTGAGAGCGTTGGACGAGAAGAAGAGTAGCTGTTATAGTTACAGGACAAGCTGTGGAATGGTATAAGAAAG |
| 207 | | Control 9 | left | 60 | 180 | 139 | | GGGTTCCCTAAGGGTTGGACCATCCAAATTATGATATATCACACTCTAGATAAGAGTTGATCTTGCTGGCaC |
| | | | middle | 60 | 180 | 140 | P- | GTATTGAAGAACTGGAAGAACTGGACCATCCAAATTTGTATGAGCCACCCCAAGCTGTAGTTACAGGACAAGCTAAGAGTTGATCTTGCTGGCaC |
| | | | right | 60 | 180 | 141 | P- | TTGTTTATAGCCATCCAAATTATGATATATTAAAAGCAGTCCCAGACTTGAACTTGTTATGGAGCAAATTATGGt |
| 210 | | Control 1 | left | 73 | 208 | 142 | | gggttccctaaggggttgaCcAGGCTGATATGCTGAAACTTGTAGTTGTGAGCCAGAGCGTGAGGCATTTTCTCTGGtctagattggatcttgctggcac |
| | | | middle | 69 | 208 | 143 | P- | GTAATTCCTATGCTGAAACTTGTAGTTGTGAGGCATTTAATTTTTAAAGGTTTCATTTTCCTATTGGTCTGATTT |
| | | | right | 66 | 208 | 144 | P- | CACAGGAACATTTACCTGTTTGGACCCAGCCAGCAGCATTAATTTTTAAAGGTTTCATTTCCTTGGtctagattggatcttgctggcac |
| 209 | | Control 10 | left | 78 | 223 | 145 | | gggttcctaaggttgaCAGCCAGCAGCCCAAGCTGATAAGAGTTAATCTAAAGAGCAAATTATGGt |
| | | | middle | 69 | 223 | 146 | P- | GTAATTCCTATGCTGAAACTTGTAGTTAATTTTTAAAAGGTTTCATTTTCCTATTGGTCTGATTT |
| | | | right | 76 | 223 | 147 | P- | CACAGGAACATTTACCTGTTTGGACCCAGGCATTTTTTCTCCTGGtctagattggatcttgctggcac |
| X ex4 | A | X exon 4 | left | 65 | 134 | 148 | | GGGTTCCCTAAGGGTTGGACCCCTTAATCCAAAGTGCTGCTCAACAAGAGTTCGAAGACAACTG |
| X ex4 | B | X exon 4 | right | 69 | 134 | 149 | P- | GACAGGAATCTCACCTTTCATAAAATGTGGCATGGATGATTGCACtctagattggatcttggcac |
| X ex9 | A | X exon 9 | left | 57 | 170 | 150 | | GGGTTCCCTAAGGGTTGGACACCCTTTACACTGACATCCGCCCCTGAGGAAGACTT |
| X ex9 | B | X exon 9 | middle | 56 | 170 | 151 | P- | CTTTAGTATCCATATCCGCCATCGTTGGGACTGGACAGAGGGGCTGTTCAATGCTT |
| X ex9 | C | X exon 9 | right | 57 | 170 | 152 | P- | GTGGCTGTGATAAGCAGGAGTTTCAAGATGCGTGtctagattggatcttgctggcac |

Fig. 3E

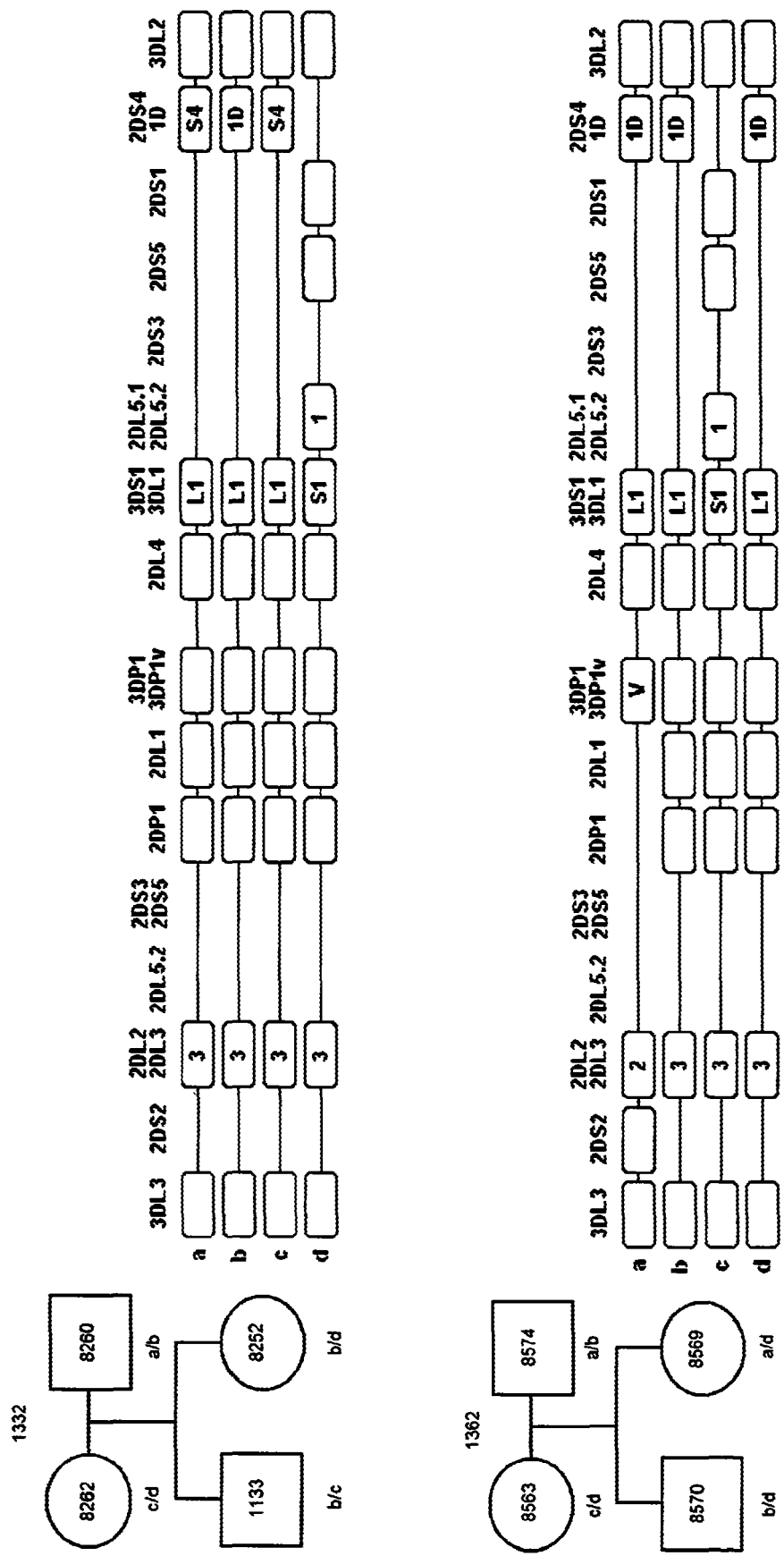
Fig. 7, condt.

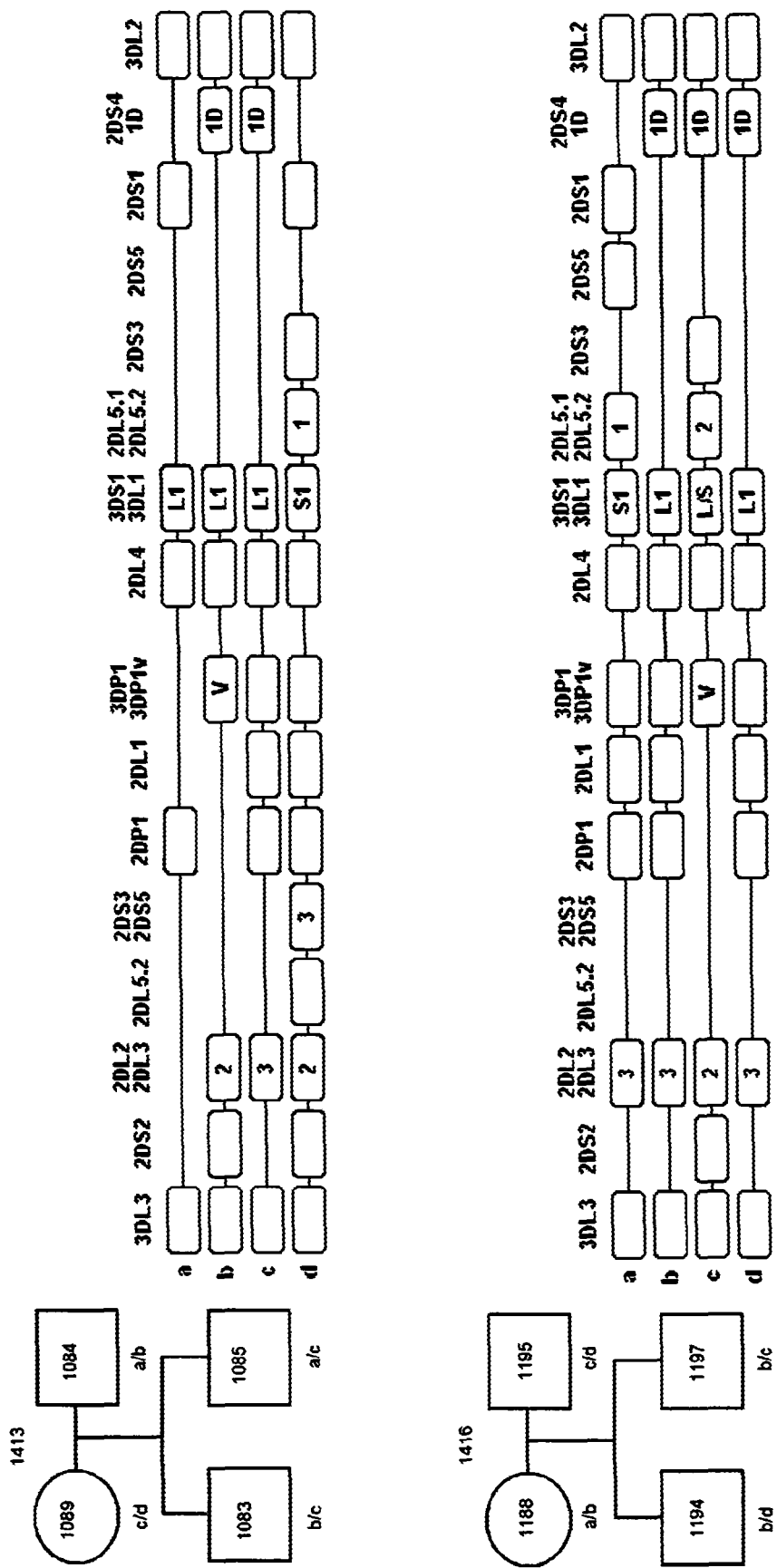
Fig. 7, condt.

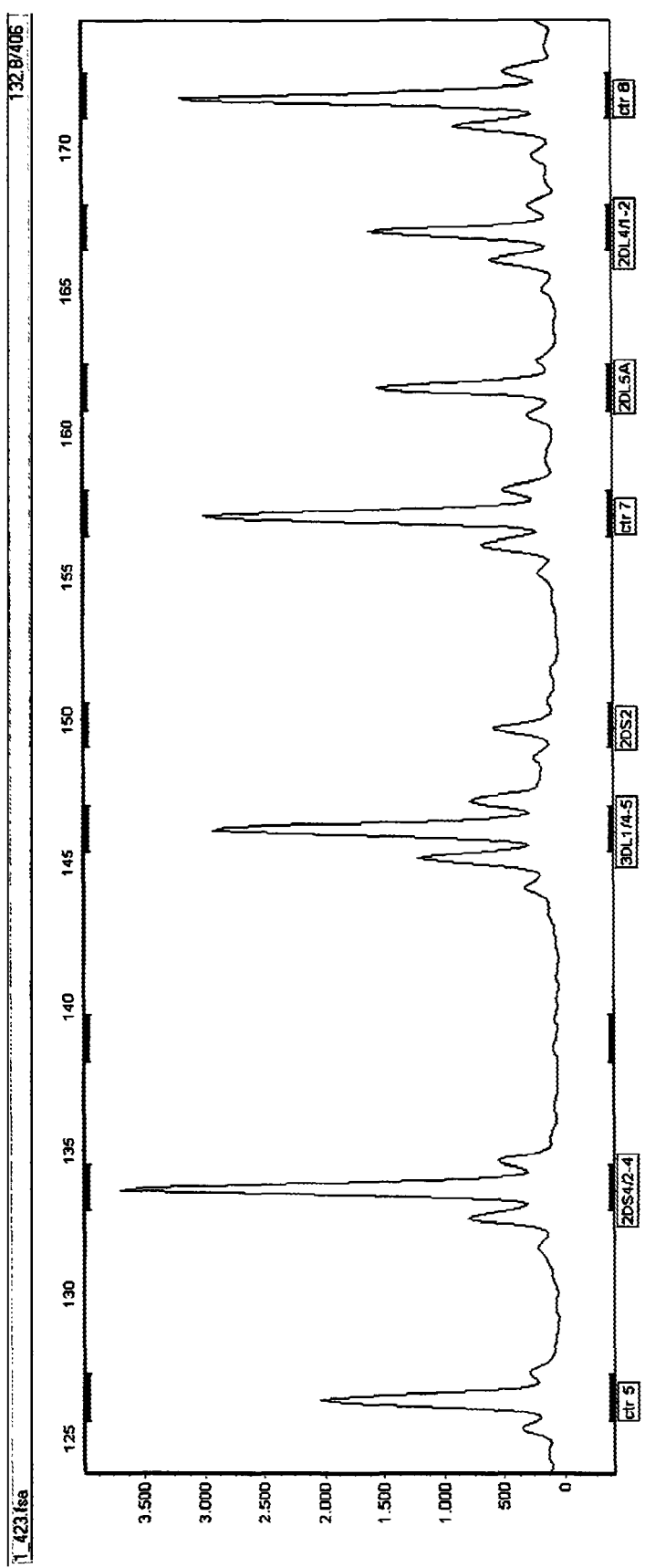
Fig. 9, condt.

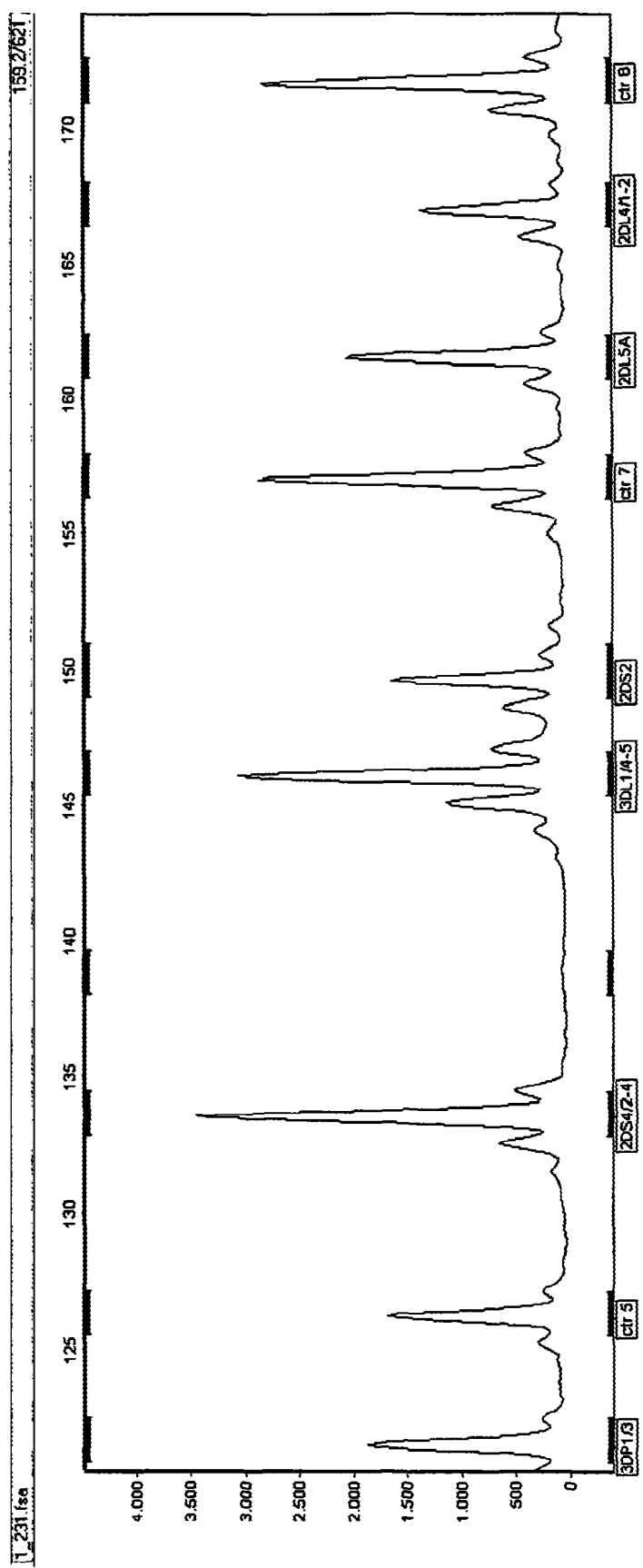
Fig. 10, condt.

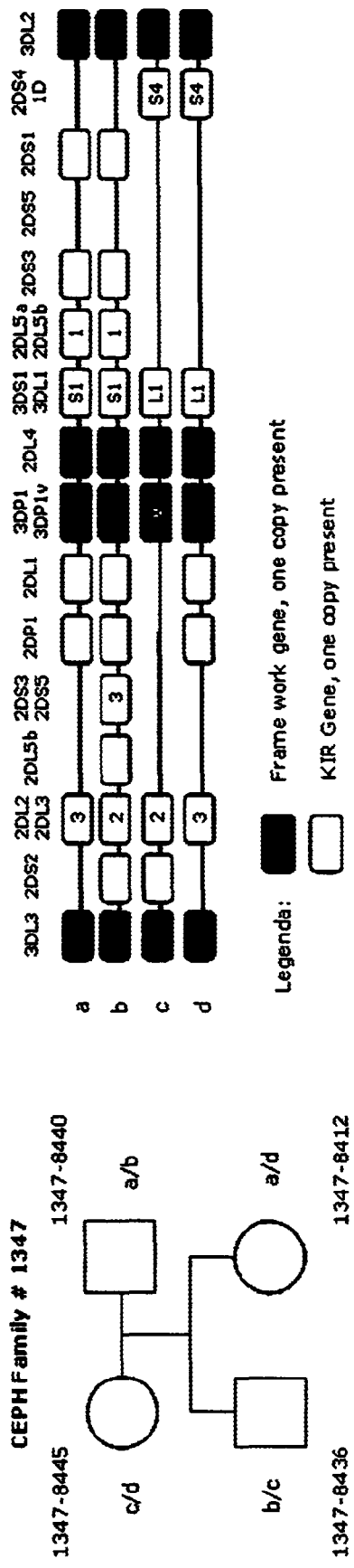
Fig. 11B1

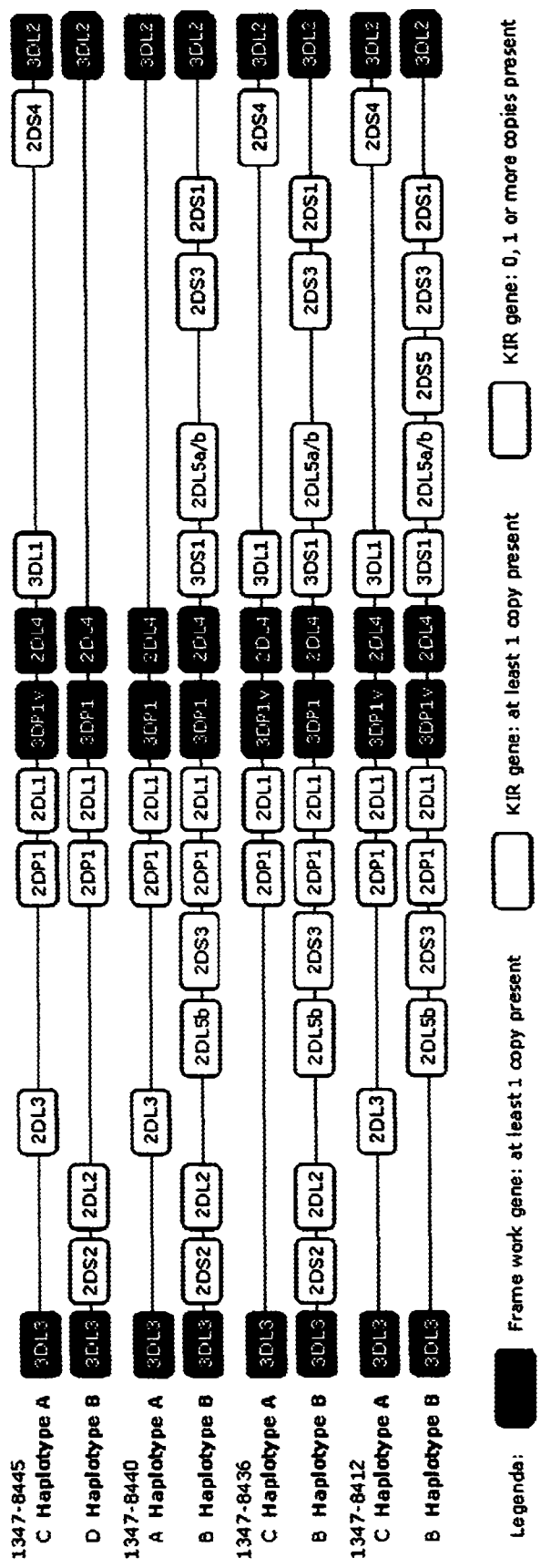
Fig. 11B2

1. Copy number variation by SSP-PCR using the conventional KIR haplotype model ¶

| | 3DL3 | 2DS2 | 2DL2 | 2DL3 | 2DP1 | 2DL1 | 3DP1 | 3DP1v | 2DL4 | 3DL1 | 3DS1 | 2DL5 | 2DL5a | 2DL5b | 2DS5 | 2DS3 | 2DS1 | 2DS4 | 1D | 3DL2 |
|---|---|---|---|---|---|---|---|---|---|---|---|---|---|---|---|---|---|---|---|---|
| 1347-8445 | 2 | 1 | 1 | 1 | 1 | 1 | 1 | 1 | 2 | 2 | 0 | 0 | | | 0 | 0 | 0 | 0 | 0 | 2 |
| 1347-8440 | 2 | 1 | 2 | 2 | 2 | 0 | 2 | 0 | 2 | 0 | 2 | 3 | | | 0 | 3 | 2 | 2 | 0 | 2 |
| 1347-8436 | 2 | 2 | 1 | 1 | 1 | 1 | 1 | 1 | 2 | 1 | 1 | 2 | | | 0 | 2 | 1 | 0 | 0 | 2 |
| 1347-8412 | 2 | 2 | 0 | 2 | 2 | 0 | 2 | 0 | 2 | 1 | 1 | 1 | | | 0 | 1 | 1 | 1 | 0 | 2 |

2. Copy number variation based on the novel KIR haplotype model using existing SSP-PCR data (CEPH-IHWG)

| | 3DL3 | 2DS2 | 2DL2 | 2DL3 | 2DP1 | 2DL1 | 3DP1 | 3DP1v | 2DL4 | 3DL1 | 3DS1 | 2DL5 | 2DS5 | 2DS3 | 2DS1 | 2DS4 | 1D | 3DL2 |
|---|---|---|---|---|---|---|---|---|---|---|---|---|---|---|---|---|---|---|
| 1347-8445 | 2 | 1 | 1 | 1 | 1/2 | 1/2 | 1 | 1 | 2 | 1 | 0 | 0 | 0 | 0 | 0 | 1 | 0 | 2 |
| 1347-8440 | 2 | 1 | 1 | 1 | 1/2 | 1/2 | 2 | 0 | 2 | 0 | 1 | 1/2 | 0 | 1 | 1 | 0 | 0 | 2 |
| 1347-8436 | 2 | 1 | 1 | 0 | 1/2 | 1/2 | 1 | 1 | 2 | 1 | 1 | 1/2 | 0 | 1 | 1 | 1 | 0 | 2 |
| 1347-8412 | 2 | 1 | 1 | 1 | 1/2 | 1/2 | 2 | 0 | 2 | 1 | 1 | 1/2 | 0 | 1 | 1 | 1 | 0 | 2 |

Legenda:
¶ Minimum number of copies present. 1/2 means (at least) 1 or 2 copies present depending on which allele the gene is present (either one or both).

Fig. 11B3

3. Copy number variation by KIR-MLPA using the new extended KIR probesets 1 and 2

| | 3DL3 | 2DS2* | 2DL2 | 2DL3 | 2DP1 | 2DL1 | 3DP1 | 3DP1v | 2DL4 | 2DL4N | 3DL1 | 3DL1N | 3DS1 | 3DS1N | 2DL5 | 2DL5a | 2DL5b | 2DS5 | 2DS3 | 2DS1 | 2DS4 | 2DS4N | 3DL2 |
|---|---|---|---|---|---|---|---|---|---|---|---|---|---|---|---|---|---|---|---|---|---|---|---|
| 1347-8445 | 2 | 1 | 1 | 1 | 1 | 1 | 2 | 0 | 2 | 0 | 1 | 0 | 0 | 0 | 0 | | | 0 | 0 | 2 | 2 | 0 | 2 |
| 1347-8440 | 2 | 1 | 1 | 1 | 2 | 2 | 2 | 0 | 2 | 0 | 0 | 0 | 2 | 0 | 4 | | | 0 | 2 | 2 | 0 | 0 | 2 |
| 1347-8436 | 2 | 1 | 1 | 0 | 1 | 1 | 2 | 1 | 2 | 0 | 1 | 1 | 1 | 1 | 2 | | | 0 | 1 | 2 | 1 | 0 | 2 |
| 1347-8412 | 2 | 0 | 0 | 2 | 2 | 2 | 2 | 0 | 2 | 0 | 0 | 1 | 0 | 0 | 2 | | | 0 | 1 | 2 | 1 | 0 | 2 |

Fig. 11B3, contd.

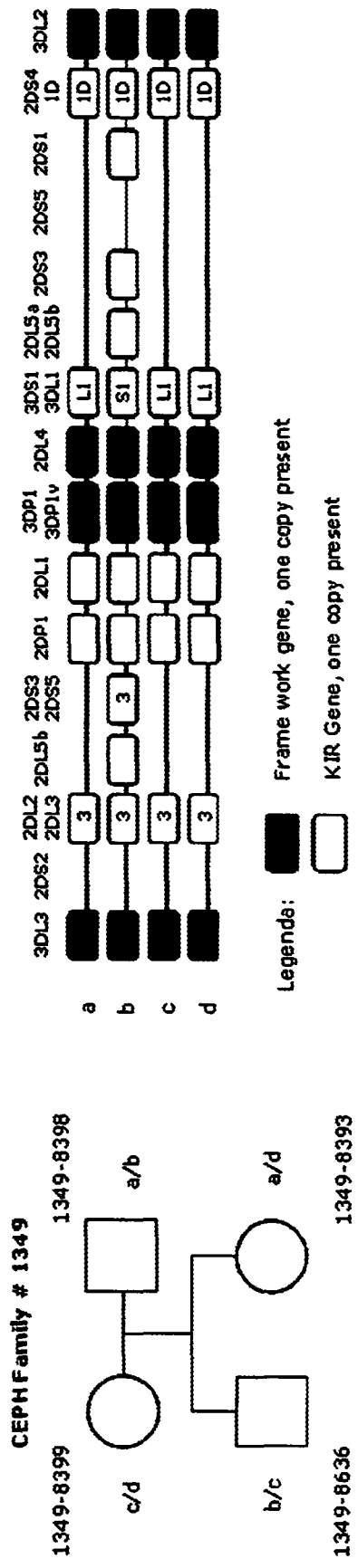
Fig. 12B1

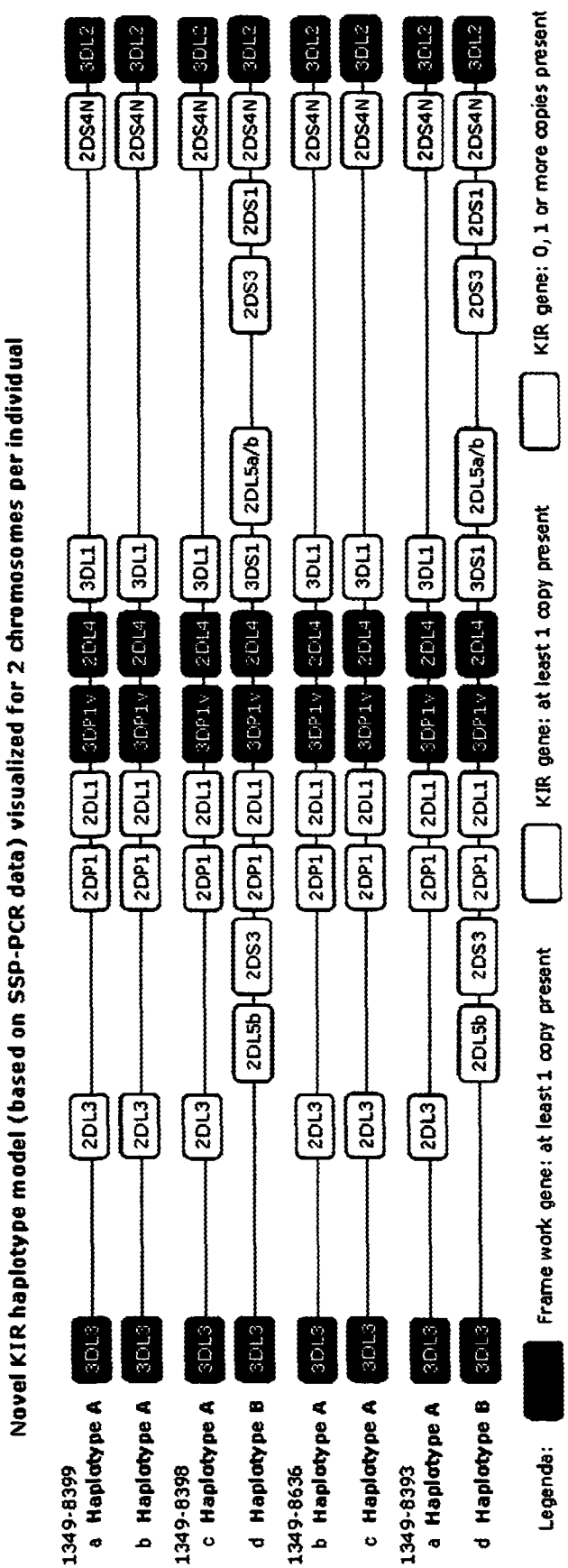
Fig. 12B2

1. Copy number variation by SSP-PCR using the conventional KIR haplotype model

| | 3DL3 | 2DS2 | 2DL2 | 2DL3 | 2DP1 | 2DL1 | 3DP1 | 3DP1v | 2DL4 | 3DL1 | 3DS1 | 2DL5 | 2DL5a | 2DL5b | 2DS5 | 2DS3 | 2DS1 | 2DS4 | 1D | 3DL2 |
|---|---|---|---|---|---|---|---|---|---|---|---|---|---|---|---|---|---|---|---|---|
| 1349-8399 | 2 | 0 | 0 | 2 | 2 | 2 | 2 | 0 | 2 | 2 | 0 | 0 | | | 0 | 0 | 0 | 0 | 2 | 2 |
| 1349-8398 | 2 | 0 | 0 | 2 | 2 | 2 | 2 | 0 | 2 | 1 | 1 | 1 | | | 0 | 1 | 1 | 0 | 2 | 2 |
| 1349-8636 | 2 | 0 | 0 | 2 | 2 | 2 | 2 | 0 | 2 | 2 | 0 | 0 | | | 0 | 0 | 0 | 0 | 2 | 2 |
| 1349-8393 | 2 | 0 | 0 | 2 | 2 | 2 | 2 | 0 | 2 | 1 | 1 | 1 | | | 0 | 1 | 1 | 0 | 2 | 2 |

2. Copy number variation based on the novel KIR haplotype model using existing SSP-PCR data (CEPH-IHWG)

| | 3DL3 | 2DS2 | 2DL2 | 2DL3 | 2DP1 | 2DL1 | 3DP1 | 3DP1v | 2DL4 | 3DL1 | 3DS1 | 2DL5 | 2DL5a | 2DL5b | 2DS5 | 2DS3 | 2DS1 | 2DS4 | 1D | 3DL2 |
|---|---|---|---|---|---|---|---|---|---|---|---|---|---|---|---|---|---|---|---|---|
| 1349-8399 | 2 | 0 | 0 | 1/2 | 1/2 | 1/2 | 2 | 0 | 2 | 1/2 | 0 | 0 | | | 0 | 0 | 0 | 0 | 1/2 | 2 |
| 1349-8398 | 2 | 0 | 0 | 1 | 1/2 | 1/2 | 2 | 0 | 2 | 1 | 1 | 1/2 | | | 0 | 1 | 1 | 0 | 1/2 | 2 |
| 1349-8636 | 2 | 0 | 0 | 1/2 | 1/2 | 1/2 | 2 | 0 | 2 | 1/2 | 0 | 0 | | | 0 | 0 | 0 | 0 | 1/2 | 2 |
| 1349-8393 | 2 | 0 | 0 | 1 | 1/2 | 1/2 | 2 | 0 | 2 | 1 | 1 | 1/2 | | | 0 | 1 | 1 | 0 | 1/2 | 2 |

Legenda: 1 — Minimum number of copies present. 1/2 means (at least) 1 or 2 copies present depending on which allele the gene is present (either one or both).

Fig. 12B3

3. Copy number variation by KIR-MLPA using the new extended KIR probesets 1 and 2

| | 3DL3 | 2DS2* | 2DL2 | 2DL3 | 2DP1 | 2DL1 | 3DP1 | 3DP1v | 2DL4 | 2DL4N | 3DL1 | 3DL1N | 3DS1 | 3DS1N | 2DL5 | 2DL5a | 2DL5b | 2DS5 | 2DS3 | 2DS1 | 2DS4 | 2DS4N | 3DL2 |
|---|---|---|---|---|---|---|---|---|---|---|---|---|---|---|---|---|---|---|---|---|---|---|---|
| 1349-8399 | 2 | 0 | 0 | 2 | 2 | 2 | 2 | 1 | 2 | 0 | 2 | 1 | 0 | 0 | 0 | | | 0 | 0 | 0 | 0 | 1 | 2 |
| 1349-8398 | 2 | 0 | 0 | 1 | 2 | 2 | 2 | 0 | 2 | 0 | 1 | 0 | 1 | 0 | 2 | | | 0 | 1 | 1 | 1 | 0 | 2 |
| 1349-8636 | 2 | 0 | 0 | 2 | 2 | 2 | 2 | 1 | 2 | 0 | 2 | 0 | 0 | 0 | 0 | | | 0 | 0 | 0 | 0 | 1 | 2 |
| 1349-8393 | 2 | 0 | 0 | 1 | 2 | 2 | 2 | 0 | 2 | 0 | 1 | 0 | 1 | 0 | 2 | | | 0 | 1 | 1 | 1 | 0 | 2 |

| Gene | SSP KIR Genotype | MLPA KIR Genotype | MLPA KIR CNV |
|---|---|---|---|
| 3DL3 *, ‡ | + | + | + |
| 2DL3 * | + | + | + |
| 2DS2 *, ‡ | + | + | + |
| 2DL2 | + | + | + |
| 2DP1 | + | + | + |
| 2DL1 * | + | + | + |
| 3DP1 | + | + | + |
| 3DP1v | + | + | |
| 2DL4 *, ‡ | + | + | + |
| 2DL4N *, ¶, ‡ | | + | + |
| 3DL1 *, ‡ | + | + | + |
| 3DL1N *, ¶, ‡ | | + | + |
| 3DS1 *, ‡ | + | + | + |
| 3DS1N *, ¶, ‡ | | + | + |
| 2DL5 * | + | + | + |
| 2DL5a *, ¶, ‡ | | + | |
| 2DL5b *, ¶ | | + | |
| 2DS3 | + | + | + |
| 2DS5 *, ‡ | + | + | + |
| 2DS4 *, ‡ | + | + | + |
| 2DS4N *, ‡ | + | + | + |
| 2DS1 *, ‡ | + | + | + |
| 3DL2 *, ‡ | + | + | + |

\* The probes for these genes are of the Tri-lig type in the MLPA probe sets described, as depicted in figures 3C and 3D.
¶ KIR variant genes that can only be detected by Tri-lig probes.
‡ Tri-lig probes that detect two different SNPs, one on each ligation site.

MEANS AND METHODS FOR INVESTIGATING NUCLEIC ACID SEQUENCES

INCORPORATION BY REFERENCE OF SEQUENCE LISTINGS

Incorporated by reference herein are 43 sequence listings uploaded to EFS Web on Sep. 15, 2011 in one file: 11-40082-US.txt (Sep. 6, 2011, 8.77 kb).

This application is the United States national stage of International Application No. PCT/NL2009/050669, filed Nov. 5, 2009, which was published under PCT Article 21 in English as International Publication No. WO 2010/053363, and which claims benefit of International Application No. PCT/NL2008/050698 filed Nov. 5, 2008 which is herein incorporated by reference.

The invention relates to the fields of biology, molecular biology, biotechnology and medicine.

Nucleic acid sequences are investigated in a wide variety of applications. For instance, for diagnosis of infection with a pathogen, a sample of an individual is often screened for the presence of pathogen nucleic acid. Furthermore, nucleic acid sequence investigation is often performed for the diagnosis of genetic disorders, such as for instance Prader-Willi syndrome, Angelman syndrome and Duchenne muscular dystrophy. Widely used methods for detection of deletions or duplications of chromosomal sequences are quantitative multiplex PCR and quantitative Southern blotting. Drawbacks of these methods are that they are time-consuming and that results are difficult to interpret.

One particularly suitable technique for investigation of nucleic acid sequences is multiplex ligation dependent probe amplification (MLPA). This technique is based on hybridisation of probes to target nucleic acids, where after probes are amplified. In currently used MLPA assays, each MLPA probe set consists of two half probes. These two half probes contain a target-specific sequence and a primer binding site sequence to which a nucleic acid amplification primer (preferably a PCR primer) can bind. One half probe is typically shorter in length then the other. The other half probe is longer due to a non-hybridizing stuffer sequence. The stuffer sequence of each probe set is unique in length, resulting in different lengths of amplification products (typically between 130 and 480 base pairs) that can be separated by electrophoresis. In an MLPA assay, typically a plurality of probe sets is used. The two half probes of each probe set are typically added to denatured sample nucleic acid and hybridized immediately adjacent to each other on their target sequence. Subsequently, the resulting nucleic acid is subjected to a ligation reaction. Usually a ligase is used which ligates only half probes that are perfectly matched with their target sequence (such as for instance the thermostable Ligase-65). A mismatch of a half probe at the ligation site prevents ligation and amplification. Thereby no amplification products of the probe will be detected. This allows MLPA to discriminate sequences that only differ in a single nucleotide. Sequences from pseudogenes or related genes can therefore be distinguished. Ligated half probes (which are also referred to as "ligated probes") are amplified, preferably by PCR, using primers capable of specifically binding the primer binding site sequences of the probes. The amplification products of each ligated probe are separated and analyzed, for instance by electrophoresis. Preferably, amplification products are represented graphically by separate peaks. Each peak is the product of an amplified MLPA ligated probe and a relative difference in peak intensity (height or surface) between a control sample and a sample of interest indicates copy number variation. FIG. 1A schematically outlines an MLPA reaction.

MLPA is particularly suitable for detecting nucleic acid (pseudo)gene variants, (pseudo)gene-specific nucleotides and/or copy number variation. MLPA has been employed in several studies, e.g. for the diagnosis of Prader-Willi or Angelman syndromes, for prenatal diagnosis of chromosomal aberrations in fetuses, and for the detection of exon deletions and/or duplications in the Duchenne muscular dystrophy gene. Overall, the conclusion was that MLPA could replace the existing methods used for screening of chromosomal abnormalities due to its relative simplicity, reproducibility and speed.

In an MLPA assay, targeted nucleic acid which is gene-specific or pseudogene-specific is preferably present at the ligation site of the half probes. When a gene-specific or pseudogene-specific nucleotide is present at (or within three nucleotides from) a ligation site, this will ensure that only perfectly matched half probes are ligated to each other. A mismatch of a half probe at the ligation site prevents ligation and amplification, whereas a perfect match of the half probe at the ligation site allows ligation and amplification. As said before, this allows MLPA to discriminate between sequences that only differ in a single nucleotide. Mismatches at four to six nucleotides away from the ligation site have been reported to have little effect on the ligation step.

Hence, the half probes are preferably designed such that the half probe whose 3' end hybridizes at a target sequence (called herein a "left probe" or a "left half probe") is complementary to a gene-specific sequence or pseudogene-specific sequence of the target sequence. This gene-specific or pseudogene-specific sequence of the target sequence comprises at least one but preferably more nucleotides that make the probe specific for a given gene or pseudogene. Preferably, at least one of the 3' end nucleotides of said left half probe is complementary to at least one gene-specific nucleotide and/or at least one pseudogene-specific nucleotide of the target sequence, so that the (pseudo)gene-specific nucleotide(s) or a single nucleotide polymorphism within a given (pseudo)gene is present at (or within three nucleotides from) the ligation site of said left half probe. In this case, said left half probe and the probe whose 5' end hybridizes at a target sequence (called herein a "right probe" or a "right half probe") are ligated to each other only when the sequence of the left half probe perfectly matches its target sequence.

As used herein the term "gene-specific nucleotide" or "gene-specific sequence" means a nucleotide or sequence, respectively, which is present in said gene but not present at the corresponding location in at least one other related gene or pseudogene. The term "pseudogene-specific nucleotide" or "pseudogene-specific sequence" means a nucleotide or sequence, respectively, which is present in said pseudogene but not present at the corresponding location in at least one other related gene or pseudogene. Hence, at least one other (pseudo)gene comprises another nucleotide or sequence at that location. The presence of a (pseudo)gene-specific nucleotide or (pseudo)gene-specific sequence in a (pseudo)gene thus distinguishes said (pseudo)gene from at least one other (pseudo)gene, even in case when the other (pseudo)gene has a high overall homology with said (pseudo)gene.

A pseudogene is defined herein as a nucleic acid sequence which does not encode a wild type, functional, protein. The term "pseudogene" encompasses nucleic acid sequences which do not encode protein at all. Additionally, the term "pseudogene" encompasses gene alleles which comprise a modification, for instance an insertion or deletion so that they encode a protein or a part of a protein with significantly impaired, or lost, function as compared to a wild type protein of the same kind. Such allele for instance encodes a truncated protein as a result of a frame shift caused by an insertion and/or deletion of at least one nucleotide, or caused by a premature stop codon.

Since ligases only ligate half probes which are adjacent to each other, half probes need to be designed which are capable of hybridizing immediately adjacent to each other on their target sequence. This is not always convenient, because the hybridization location of a left half probe on a target nucleic acid is often determined by a (pseudo)gene-specific site of the target nucleic acid (as explained above). In such case, the sequence of the corresponding right half probe is determined as well, since the right half probe should be capable of hybridizing to a region of said target nucleic acid which is immediately adjacent to said (pseudo)gene-specific nucleotide. However, such region may comprise sequences which are very commonly present in the nucleic acid sequences of a sample. As a result, a right half probe having a sequence which is complementary to such common sequence will hybridize at many different sites of the nucleic acids present in a sample. In such case, it would be more attractive to design a right half probe with a sequence which is more specific for a given site of interest of a target nucleic acid. However, if the left half probe and the right half probe do not hybridize to adjacent regions of a target nucleic acid, the commonly used ligases will not be capable of performing the ligation reaction. Patent application WO 01/61033 in the name of Schouten discloses a solution to this problem by adding a short third probe to the reaction mixture, which third probe will fill the gap between the left half probe and the right half probe. Such third probe is designed to hybridize to a region of a target nucleic acid which lies between the left and the right half probes. After hybridization of such third probe, the left half probe is connected to the right half probe via the third probe and ligation has become possible. The third half probe does not need to be perfectly complementary to the region of the target nucleic acid which lies between the left and the right half probes, as long as the third probe connects the left half probe and the right half probe so that a ligase reaction can occur. Moreover, since the third probe is small, it will hybridize more easily to the target nucleic acid as compared to the left and right half probes. Hence, mismatches between the third probe and the target nucleic acid are allowed. This way, one and the same third probe is suitable for connecting left and right half probes of different probe sets.

Instead of using a third probe, WO 01/61033 also discloses an embodiment wherein the 3' end of a left half probe is extended after hybridization of the half probes to the target sequence, so that the gap between the left half probe and the right half probe is filled. The resulting extended left half probe is adjacent to the right half probe and a ligase reaction has become possible.

In order to be capable of distinguishing between amplificates of different probe sets, currently used MLPA probe sets are designed such that the resulting amplificates have a different length. Differences in ligated probe length are typically realized by using a non-hybridizing stuffer sequence in one of the half probes. The stuffer sequence of the half probes of each probe set is unique in length, resulting in different lengths of amplification products that can be separated by electrophoresis. Typically, in order to be capable of discriminating between the different amplification products, the difference in length between different ligated probes is at least 5 nucleotides. Since a usual MLPA assay involves the use of many different probe sets in order to be capable of detecting a wide variety of (pseudo)gene variants, this means that long probes have to be generated. This is especially the case when complex loci carrying many (pseudo)gene-specific nucleotides are investigated for proper genotyping and/or additional single nucleotide polymorphisms are investigated for detection of subtle genetic variation within a specific genotype, as well as the presence of pseudogenes and single nucleotides in these pseudogenes. Such investigation requires the use of many different probe sets. This is inconvenient if probes are chemically synthesized, because a drawback of synthetic probes is the lower quality in comparison with cloned probes, due to contamination with incompletely synthesized probes. These incompletely synthesized probes lack or gain one nucleotide, which results in stutter peaks and split peaks. A method to remove these contaminants is to purify the synthesized probes, for instance by polyacrylamid gel electrophoresis (PAGE). If short and long probes are chemically synthesized, a higher proportion of longer probes is more likely to be affected by the incomplete oligonucleotides, causing a limitation of synthetic probe size. The upper limit of synthetic probes is typically about 100 base pairs.

On the other hand, the use of synthetic probes is preferred because they are easy to obtain and cost-effective whereas generating a probe by cloning in bacteriophage vectors is a time-consuming process and more expensive.

Hence, although good results have been obtained with currently used MLPA assays, it is desirable to provide alternatives and improvements, especially if complex (pseudo) gene loci are investigated which involves the use of many probe sets.

It is an object of the present invention to provide alternative and improved MLPA methods and MLPA-like methods.

Accordingly, the present invention provides MLPA assays and MLPA-like assays wherein at least one probe set is used which comprises a first nucleic acid probe ("left probe" or "left probe part"), a second nucleic acid probe ("right probe" or "right probe part") and a third nucleic acid probe ("third probe" or "middle probe" or "middle probe part"), wherein at least one third probe is complementary to a target nucleic acid region comprising a (pseudo)gene-specific nucleotide or (pseudo)gene-specific sequence.

The present invention provides a different approach as compared to the prior art. MLPA methods and MLPA-like methods are now provided wherein at least one third probe, but preferably a plurality of third probes, is used in order to detect at least one (pseudo)gene-specific nucleotide of a target nucleic acid. Hence, an additional probe is used in at least one of the probe sets, which is specific for a (pseudo)gene-specific target nucleic acid. As used herein, an MLPA-like method is defined as a method comprising the steps of hybridisation of at least two probes to a target nucleic acid and ligation of at least two probes. Preferably, said MLPA-like method comprises amplification of ligated probes as well.

MLPA methods and MLPA-like methods according to the present invention have several advantages as compared to current methods. For instance, if the left probe and the third probe of a probe set are both complementary to target nucleic acid regions comprising (pseudo)gene-specific nucleotides and/or additional single nucleotide polymorphism(s), two different (pseudo)gene-specific target nucleotides or two SNP's or a combination of one (pseudo)gene specific target nucleotide and one SNP are screened using one probe set. It has become possible to use one probe set in order to screen for at least two (pseudo)gene variations which are located within a region of about 150 nucleotides of a target nucleic acid. Contrary, in a currently used MLPA assay two separate probe sets are needed for screening for two variants in a target nucleic acid. This is illustrated by the following example. If a target (pseudo)gene contains a (pseudo)gene variant at location A and at location B, an individual may comprise the following alleles: a-b, a-B, A-b and A-B. In order to determine whether allele a-B is present in a sample of said individual, a currently used MLPA assay would need a probe set specific for the "a" and/or "A" (pseudo)gene variant and a probe set specific for the "B" and/or "b" (pseudo)gene variant. If both the probe set specific for "a" and the probe set specific for "B" provide a positive result, it is concluded that allele a-B is present in said individual. With a MLPA method according to the present invention, however, only one probe set is needed wherein the left probe is specific for the "a" (pseudo)gene variant and the third probe is specific for the "B" (pseudo)gene variant. If an amplification product is obtained, it is immediately concluded that allele a-B is present in said individual. If allele a-B is not present, said probe set according to the invention will not yield an amplification product. Hence, it has become possible to more specifically screen for a given allele.

Moreover, a method of the invention provides an additional advantage when two (pseudo)gene variations are located close to each other. If the (pseudo)gene variants at location A and at location B are close to each other, the use of two different probe sets according to conventional MLPA techniques is inconvenient or even not possible at all, because the two probe sets will hinder each other in view of their close proximity. This will result in less efficient hybridization of the two probe sets, resulting in a lower signal as compared to a method according to the invention, wherein two (pseudo)gene variants can be detected using only one probe set. Hence, a method according to the invention is more sensitive when (pseudo)gene variants are located close to each other (in practice, this effect will be most profound when the (pseudo)gene variants are located between 20-100 nucleotides from each other). Having two probes to detect a variant at the same position (such as in currently used MLPA assays) will result in a change in signal intensity, depending on the presence of the (pseudo)gene variant and the binding of the probe. The use of more than two probes for one position is not advised. FIG. 1B schematically outlines an MLPA reaction according to the invention in which a probe set consisting of three probes is used for detecting two SNPs. FIG. 1C shows a non-limiting example of two specific probe sets according to the invention for detecting two SNPs.

As another example, in case that an individual is heterozygous for the above mentioned (pseudo)gene, the individual for instance contains alleles a-B and A-b. A conventional MLPA assay would use four probe sets (one specific for "a", one specific for "A", one specific for "b" and one specific for "B"). Four positive results would be obtained, because all four probe sets would hybridize and result in an amplification product. However, in such case it would still be unknown whether the individual comprises the alleles a-b and A-B, or the alleles a-B and A-b. With a method according to the present invention, however, it has become possible to directly identify the alleles of said individual. For instance, a first probe set of the invention is used comprising a left probe specific for "a" and a third probe specific for "b", together with a second probe set of the invention comprising a left probe specific for "a" and a third probe specific for "B" and a third probe set of the invention comprising a left probe specific for "A" and a third probe specific for "b" and a fourth probe set of the invention comprising a left probe specific for "A" and a third probe specific for "B". Two of these probe sets according to the present invention will yield an amplification product, namely the second probe set of the invention comprising a left probe specific for "a" and a third probe specific for "B" and the third probe set of the invention comprising a left probe specific for "A" and a third probe specific for "b". The first and fourth probe sets according to the present invention will not yield (significant) amplification product. This way, it is immediately apparent which alleles are present in said individual. This, too, is an advantage as compared to currently used methods, especially when complex loci with many (pseudo)gene-specific nucleotides and additional single nucleotide polymorphisms within a given (pseudo)gene are investigated, because in such case many different combinations of such (pseudo)gene variants need to be screened for.

Another advantage of a method according to the present invention is the fact that more variations in length of the ligated probes are obtained. Since at least one probe set of the invention, but preferably a plurality of probe sets of the invention, comprise a third probe it has become possible to design the probe sets such that variations in length of the resulting ligated probes are obtained. This obviates the need of stuffer sequences. As a result, the individual probes of a probe set according to the invention can be kept shorter, which is particularly advantageous when chemically synthesized probes are used because chemical production of long probes is cumbersome, as explained above. Hence, a method according to the invention allows for the use of probe sets with relatively short probes, while the resulting ligated probes are long enough to allow for many size variations. Thus, the present invention allows the use of synthetic probes, which are easy to obtain and cost-effective, even when complex loci are investigated, and offers greater flexibility to adapt the assay in case of cross-reactivity or unclear results.

For instance, if 20 (pseudo)gene variants are investigated, probes with a stuffer sequence with a length varying from 4 to 100 nucleotides would need to be used in a conventional MLPA assay in order to be capable of distinguishing the resulting amplification products by size. Since the probe sequences hybridizing to a target sequence are typically about 30 nucleotides, and since the primer binding sequences of the probes are typically about 15-25 nucleotides, this would mean that probe sets with probes with a length varying from 45-125 nucleotides would need to be synthesized. When the probes are chemically synthesized, it is hardly possible to obtain reliable probe sets with these lengths. With a method according to the invention, however, differences of length between the various amplificates need not to be obtained by use of stuffer sequences in the probe sets. Instead, at least one third probe is used, preferably a plurality of third probes is used. By varying combinations of three probes, optionally in combination with probe sets consisting of two probes, the overall length differences of the ligated probes vary considerably whereas probe sets can be used with chemically synthesized probes with convenient lengths. Of course, this does not mean that the use of stuffer sequences is excluded. But the skilled person does no longer have to rely on these stuffer sequences only for length variations. If stuffer sequences are used in a method according to the invention, it is preferred to keep these sequences as short as possible.

Accordingly, the present invention provides a method for screening for the presence of at least one target nucleic acid sequence in a sample, comprising the steps of:
  a) adding to said sample at least two different probe sets, each probe set comprising:
    a first nucleic acid probe ("left probe"), said first probe comprising a first nucleic acid sequence complementary to a first region of said target nucleic acid sequence, and a second nucleic acid probe ("right probe"), said second probe comprising a second nucleic acid sequence complementary to a second region of said target nucleic acid sequence, wherein at least one of said probe sets comprises a third nucleic acid probe, said third probe comprising a third nucleic acid sequence complementary to a third region of said target nucleic acid sequence, and wherein, if said third probe is present in said probe set, said first and said third region of said target nucleic acid are located essentially adjacent to each other and said third and said second region of said target nucleic acid are located essentially adjacent to each other, and wherein, if said third probe is not present in said probe set, said first and said second region of said target nucleic acid are located essentially adjacent to each other, b) allowing hybridization of said at least two different probe sets to complementary nucleic acid of said sample, c) subjecting nucleic acid of said sample to a ligation reaction, and d) determining whether said at least one target nucleic acid sequence is present in said sample, wherein at least one third nucleic acid probe is complementary to a target nucleic acid region comprising a (pseudo)gene variation.

The advantage of probe sets comprising at least three probes according to the present invention is that at least two different SNPs can be detected with one probe set. For instance, in a probe set comprising three probes two sites for ligation are present. A left probe and middle probe are ligated, and a middle probe and right probe are ligated. At each ligation site a SNP can be detected. Thus it is possible to design two probes of the same probe set in such a way that they are used to detect two SNPs. In that case, using MLPA and a probe set comprising three probes according to the invention, a product will only be obtained when both SNPs are present in a sample, because only then ligation can occur at both ligation sites.

With conventional MLPA probesets consisting of two probes only one SNP can be detected, because only one site for ligation is present. Additional third probe parts in conventional MLPA, as described in WO 01/61033, are occasionally used to bridge the two half probes. Such an additional third probe part is not SNP-specific. Therefore, the advantages of probe sets comprising at least three probes according to the present invention are not obtained when using such additional third probe part for bridging purposes in conventional MLPA.

Therefore, in a preferred embodiment of the invention a probe set comprises three nucleic acid probes wherein each of at least two nucleic acid probes are specific for a different (pseudo)gene variation. Preferably, a first (or a second) nucleic acid probe of a probe set according to the invention is complementary to a target nucleic acid region comprising a gene-specific nucleotide and/or a pseudogene-specific nucleotide and/or a gene-specific sequence and/or a pseudogene-specific sequence and/or a polymorphism within a given gene or pseudogene, and a third nucleic acid probe of the same probeset is complementary to another target nucleic acid region comprising a gene-specific nucleotide and/or a pseudogene-specific nucleotide and/or a gene-specific sequence and/or a pseudogene-specific sequence and/or a polymorphism within a given gene or pseudogene. Said polymorphism preferably comprises an SNP.

Preferably, ligated probes are amplified. Accordingly, the present invention provides a method for screening for the presence of at least one target nucleic acid sequence in a sample, comprising the steps of:

a) adding to said sample at least two different probe sets, each probe set comprising:

a first nucleic acid probe ("left probe"), said first probe comprising a first nucleic acid sequence complementary to a first region of said target nucleic acid sequence and, located 5' thereof, a non-complementary nucleic acid sequence comprising a first primer binding site, and a second nucleic acid probe ("right probe"), said second probe comprising a second nucleic acid sequence complementary to a second region of said target nucleic acid sequence and, located 3' thereof, a non-complementary nucleic acid sequence comprising a second primer binding site, wherein at least one of said probe sets comprises a third nucleic acid probe, said third probe comprising a third nucleic acid sequence complementary to a third region of said target nucleic acid sequence, and wherein, if said third probe is present in said probe set, said first and said third region of said target nucleic acid are located essentially adjacent to each other and said third and said second region of said target nucleic acid are located essentially adjacent to each other, and wherein, if said third probe is not present in said probe set, said first and said second region of said target nucleic acid are located essentially adjacent to each other, b) allowing hybridization of said at least two different probe sets to complementary nucleic acid of said sample, c) subjecting nucleic acid of said sample to a ligation reaction, d) subjecting nucleic acid of said sample to a nucleic acid amplification reaction, using at least one primer capable of specifically binding said first primer binding site and at least one primer capable of specifically binding said second primer binding site, and e) determining whether amplified nucleic acid is present, thereby determining whether said at least one target nucleic acid sequence is present in said sample, wherein at least one third nucleic acid probe is complementary to a target nucleic acid region comprising a (pseudo)gene variation.

As used herein, the term "(pseudo)gene variation" encompasses a (pseudo)gene-specific nucleotide and/or a (pseudo)gene-specific sequence. In one embodiment, said (pseudo)gene variation comprises an additional polymorphism within a given (pseudo)gene. Said additional polymorphism preferably comprises an SNP.

Hence, the present invention uses probe sets, wherein at least one probe set, but preferably a plurality of probe sets, comprises three probes. The probes comprise sequences which are complementary to a region of a target nucleic acid of interest. As used herein, the term "complementary" means that said probe sequence comprises at least 70%, preferably at least 80%, more preferably at least 85%, more preferably at least 90%, most preferably at least 95% sequence identity to said region or to the complement of said region. The term "% sequence identity" is defined herein as the percentage of residues in a nucleotide sequence that is identical with the residues in a reference sequence after aligning the two sequences and introducing gaps, if necessary, to achieve the maximum percent identity. Methods and computer programs for the alignment are well known in the art. One computer program which may be used or adapted for purposes of determining whether a candidate sequence falls within this definition is Autoassembler 2.0 (ABI Prism, Perkin Elmer).

The first and second probes of each probe set also comprise a primer binding site, so that the resulting ligated probes can be amplified. Preferably, the primer binding sites of the first nucleic acid probes of each probe set is designed such that the same primer can bind. This allows the use of the same primer for binding the primer binding sites of the first probes in step d). Likewise, it is preferred that the primer binding sites of the second nucleic acid probes of each probe set is designed such that the same primer can bind. Most preferably, the probe sets are designed such that a first primer is capable of specifically binding the primer binding sites of the first nucleic acid probes of each probe set and a second primer is capable of specifically binding the primer binding sites of the second nucleic acid probes of each probe set. This embodiment allows the use of only one primer pair in step d). This is, however, not necessary: it is also possible to use different primers for different probe sets. The number of different primers is, however, kept as low as possible.

One preferred embodiment therefore provides a method according to the invention, wherein the first primer binding sites of the first nucleic acid probes of each probe set is capable of specifically binding the same primer and/or wherein the second primer binding sites of the second nucleic acid probes of each probe set is capable of specifically binding the same primer. Preferably, the first nucleic acid probes and/or the second nucleic acid probes of each probe set comprise essentially identical primer binding sequences. Further provided is therefore a method according to the invention, wherein the non-complementary nucleic acid sequences of said first nucleic acid probes comprise essentially identical first primer binding sites and/or wherein the non-complementary nucleic acid sequences of said second nucleic acid probes comprise essentially identical second primer binding sites. Using essentially identical primer binding sequences ensures that the same primer can bind different probes. The term "essentially identical primer binding sequences" is defined herein as primer binding sequences which comprise at least 80%, preferably at least 85%, more preferably at least 90%, most preferably at least 95% sequence identity to each other.

As already described, a method according to the invention is particularly suitable for investigating a nucleic acid sequence having various (pseudo)gene specific nucleotides and/or (pseudo)gene variants, such as complex loci. It is therefore preferred to use a plurality of third probes, so that many (pseudo)gene variant combinations are investigated. A method according to the invention is therefore preferably provided wherein at least two, preferably at least five, more preferably at least ten different third nucleic acid probes are used. As illustrated in the Examples, a plurality of probe sets comprising different third probes according to the invention allows for screening of complex gene loci such as the KIR locus. Not all third probes need to be specific for a genetic variation of a target nucleic acid. It is also possible to use a combination of variant-specific third probes and third probes which are not specific for a (pseudo)gene variation. Likewise, not all first probes need to be specific for a variant of a target nucleic acid. It is also possible to use a combination of variant-specific first probes and first probes which are not specific for a (pseudo)gene variation. Any of these combinations is for instance used to vary the length of the resulting ligated probes to a larger extent. In one preferred embodiment of the invention, therefore, at least 50%, preferably at least 70%, more preferably at least 80%, most preferably at least 90% of the third nucleic acid probes is complementary to a target nucleic acid region comprising a (pseudo)gene variation. In one embodiment, all third probes are complementary to a target nucleic acid region comprising a (pseudo)gene variant. Preferably, the second probes ("right probes") are not designed to contain (pseudo)gene variant-specific sequences, although the use of variant-specific right probes in a method according to the invention is not excluded.

Preferably, at least 50%, preferably at least 70%, more preferably at least 80%, most preferably at least 90% of the third nucleic acid probes that are complementary to a target nucleic acid region comprising a (pseudo)gene variation are combined with a first nucleic acid probe or a second nucleic acid probe that is complementary to another target nucleic acid region comprising a (pseudo)gene variation in order to be capable of screening for many variants with one MLPA assay or MLPA-like assay. In one embodiment, all third probes that are combined with a first nucleic acid probe or a second nucleic acid probe that is complementary to a target nucleic acid region comprising a (pseudo)gene variation are complementary to a target nucleic acid region comprising a (pseudo)gene variant. Of course, these probes are preferably specific for different variants.

In one preferred embodiment, a (pseudo)gene variant-specific sequence of a third probe is at least located within the last three nucleotides or the first three nucleotides of the third probe. This means that the last three nucleotides and/or the first three nucleotides comprise at least one nucleotide which is specific for a (pseudo)gene variation of a target nucleic acid. In this embodiment, said (pseudo)gene variation is present at a ligation site of the third probe, so that ligation is only possible when the sequence of the third probe is exactly complementary to said (pseudo)gene variation. This enhances the specificity of the MLPA method, as explained before. Preferably, the last three nucleotides and/or the first three nucleotides of said third probe comprise one nucleotide which is specific for a (pseudo)gene variant of a target nucleotide.

The probe sets according to the present invention preferably have a length between 90 and 300 nucleotides. Cloned probes can be as long as 500 nucleotides. Preferably, however, chemically synthesized probes are used because they are rapidly synthesized, easy to obtain and cost-effective. In order to be capable of synthetically producing the probes according to the present invention, a method according to the invention is preferably provided wherein third nucleic acid probes with a length of between 20 and 100 nucleotides are used. Most preferably, third nucleic acid probes with a length of between 19 and 110 nucleotides are used. Since at least one probe set of the invention, but preferably a plurality of probe sets according to the invention, is used which comprise three nucleic acid probes, sufficient variations in length and specificity of the resulting ligated probes is ensured so that many (pseudo)gene variations can be investigated simultaneously.

These length variations of the resulting ligated probes obviate the need of stuffer sequences, as explained before. It is therefore possible to design the probe sets such that the parts of the first and/or second probe which are not complementary to a target nucleic acid have about the same length. According to this embodiment, the length of the non-complementary sequences of all first probes is about the same in each probe set, and/or the length of the non-complementary sequences of all second probes is about the same in each probe set. These lengths are about the same when they do not differ from each other by more than 10 nucleotides. Preferably, they do not differ from each other by more than 6 nucleotides, most preferably they do not differ from each other by more than 4 nucleotides. This, too, facilitates synthetic production of the probes. Further provided is therefore a method according to the invention, wherein the difference in length of said non-complementary nucleic acid sequences of said first nucleic acid probes of said at least two different probe sets and/or the difference in length of said non-complementary nucleic acid sequences of said second nucleic acid probes of said at least two different probe sets is less than 6, preferably less than 4 nucleic acids.

Besides the analysis of (pseudo)gene-specific nucleotides and additional single nucleotide polymorphisms, an MLPA technique or MLPA-like technique is particularly suitable for relative (pseudo)gene copy number determination. If multiple copies of a (pseudo)gene of interest (or any other target nucleic acid of interest) are present in sample nucleic acid molecules, each copy will, in principle, be bound by the specific probes which is detectable. When the probes are amplified, more amplification product will be present when multiple copies were present in the original sample nucleic acid as compared to a situation wherein only one copy is present. Analysis of the amount of amplification product thus provides information about the copy number of a target nucleic acid of interest. This is often done by graphically representing amplified products by separate peaks. Each peak is the product of an amplified MLPA ligated probe and a relative difference in peak intensity (height or surface) between a control sample and a sample of interest indicates copy number variation. When a complex locus is investigated, multiple copies of a (pseudo)gene of interest can be present in highly polymorphic regions. In such case, when (pseudo) gene copy number is to be determined, many different combinations of (pseudo)gene variants need to be taken into account. This involves the use of a wide variety of different probe sets, to ensure that each combination of (pseudo)gene variants can be detected. In one embodiment according to the present invention, however, when the relative copy number of a nucleic acid of interest is to be estimated, an improved approach is provided. According to this embodiment, at least one probe is used with degenerate bases at one or more positions. This means that a mixture of probes is used wherein different nucleotides can be present at one or more positions. Hence a mixture of probes is used, which probes have the same sequence, except for the fact that some probes have a certain nucleotide at a given position X and some probes have another nucleotide at said position X. Such degenerate bases are commonly represented by the IUB nucleotide codes as depicted in FIG. 2. The use of probes with degenerate bases allows for an efficient estimation of copy number of a nucleic acid of interest, even in highly polymorphic regions. Further provided is therefore a method for determining the copy number of a nucleic acid of interest, wherein at least one probe set is used which comprises a probe with (a) degenerate base(s) at one or more positions. Preferably, at most 20 probe positions have such multiple alternatives, in order to retain specificity of the probes for a given target region of interest. A use of at least one probe set for determining the copy number of a nucleic acid of interest, wherein at least one probe set comprises a probe with (a) degenerate base(s) at one or more positions, is also provided herewith. In one preferred embodiment, at least one probe set comprising a probe with (a) degenerate base(s) is used in a MLPA method or MLPA-like method according to the present invention. Further provided is therefore a method according to the invention, wherein at least one probe set is used which comprises a probe with (a) degenerate base(s) at one or more positions.

Alternatively, or additionally, a probe set is used which comprises an alternative base which alternative base is capable of binding at least two bases selected from the group consisting of A, T, G, C and U. Preferably, said alternative base is capable of binding at least three, most preferably at least four, bases selected from the group consisting of A, T, G, C and U. Such alternative base is suitable as an alternative for degenerate bases. It is, of course, also possible to combine such alternative base with degenerate bases. In a particularly preferred embodiment said alternative base is deoxyinosine triphosphate (dITP) or a functional equivalent thereof, which is capable of binding A and T and G and C and U. Further provided is therefore a method for determining the copy number of a nucleic acid of interest, wherein at least one probe set is used which comprises an alternative base which is capable of binding at least two, preferably at least three, more preferably at least four bases selected from the group consisting of A, T, G, C and U. As said before, said alternative base preferably comprises deoxyinosine triphosphate (dITP) or a functional equivalent thereof. A use of at least one probe set for determining the copy number of a nucleic acid of interest, wherein at least one probe set comprises an alternative base which is capable of binding at least two, preferably at least three, more preferably at least four bases selected from the group consisting of A, T, G, C and U, is also provided herewith. In one preferred embodiment, at least one probe set comprising such alternative base(s) is used in a MLPA method or MLPA-like method according to the present invention. Further provided is therefore a method according to the invention, wherein at least one probe set is used which comprises an alternative base which is capable of binding at least two, preferably at least three, more preferably at least four bases selected from the group consisting of A, T, G, C and U. As said before, said alternative base preferably comprises deoxyinosine triphosphate (dITP) or a functional equivalent thereof.

The present invention provides alternative and improved methods for screening for the presence of at least one target nucleic acid sequence in a sample, wherein at least one third probe is used which is complementary to a target nucleic acid region comprising a (pseudo)gene variation. A use of a probe set comprising at least three nucleic acid probes, wherein at least one third probe is complementary to a target nucleic acid region comprising a gene variant and/or a pseudogene variant, for screening for the presence of at least one target nucleic acid sequence in a sample is therefore also provided.

Preferably, a plurality of probe sets according to the present invention is used.

Further provided is therefore a use of a plurality of probe sets for screening for the presence of at least one target nucleic acid sequence in a sample, wherein each of said probe sets comprises:
  a first nucleic acid probe, said first probe comprising
    a first nucleic acid sequence complementary to a first region of said target nucleic acid sequence and, located 5' thereof, a non-complementary nucleic acid sequence comprising a first primer binding site, and
  a second nucleic acid probe, said second probe comprising
    a second nucleic acid sequence complementary to a second region of said target nucleic acid sequence and, located 3' thereof, a non-complementary nucleic acid sequence comprising a second primer binding site,
  wherein at least one of said probe sets comprises a third nucleic acid probe, said third probe comprising a third nucleic acid sequence complementary to a third region of said target nucleic acid sequence, and
  wherein, if said third probe is present in said probe set, said first and said third region of said target nucleic acid are located essentially adjacent to each other and said third and said second region of said target nucleic acid are located essentially adjacent to each other, and wherein, if said third probe is not present in said probe set, said first and said second region of said target nucleic acid are located essentially adjacent to each other, and wherein at least one third nucleic acid probe is complementary to a target nucleic acid region comprising a gene-specific nucleotide and/or a pseudogene-specific nucleotide and/or a gene-specific sequence and/or a pseudogene-specific sequence and/or an additional polymorphism within a given gene or pseudogene, said polymorphism preferably comprising an SNP.

A method according to the present invention is particularly suitable for analysis of (pseudo)gene variation and (pseudo) gene copy number determination in complex loci such as the gene encoding complement factors (e.g. Factor H and FH-like genes, C4A and C4B within the HLA-class III region), chemokines and their receptor alleles (e.g. CCL3L1, CCL4L1, CCR5 or CCR5delta32), HLA-class I and II, SIRPs and LILRs.

In one preferred embodiment, a method according to the invention is used in order to investigate the killer cell immunoglobulin-like receptor (KIR) locus. KIRs are expressed by natural killer (NK) cells and a subset of T cells. NK cells are cells of the lymphoid lineage, but display no antigen-specific receptors. Their main function is to monitor host cells for the presence of MHC class I molecules and this is important for e.g. distinguishing healthy cells from virus-infected or tumors cells. Interaction between NK cells and MHC class I molecules is mediated by KIRs. The KIR locus in humans is polygenic and highly polymorphic, so that accurate and efficient characterization of an individual's KIR (pseudo)gene profile is cumbersome. In the determination of the KIR (pseudo)gene profile and their role in many diseases an efficient and reliable method for KIR genotyping is, however, important. Until now, KIR genotyping is based upon the polymerase chain reaction sequence-specific primer (PCR-SSP) (Sun et al, 2004), multiplex PCR (Vilches et al, 2007) and PCR-sequence specific oligonucleotide probes (PCR-SSOP) (Crum et al, 2000). For the PCR-SSP high-quality genomic DNA is required and multiple reactions are needed to generate a complete KIR profile of an individual. Multiple copies of KIR2DL4 and KIR3DL1/S1 in individuals have been reported with PCR-SSOP (Williams et al, 2003). Detection of the multiple gene copies was possible because the gene copies of these genes consisted of different alleles. However, multiple gene copies of highly homologous or identical sequences are not distinguishable with this molecular detection system or cloning methods when individuals are homozygous for a gene (Williams et al, 2003).

As shown in the Examples, a method according to the present invention is particularly suitable for investigating the KIR locus of individuals. Even though this locus is highly polymorphic, (pseudo)gene variants and copy number variations are efficiently detected with methods according to the present invention. One preferred embodiment therefore provides a method or use according to the invention, wherein said target nucleic acid sequence is present in a KIR locus. Preferably, copy number variation of at least one KIR gene and/or at least one KIR pseudogene is determined. FIGS. 3A and B provides KIR-specific probes which provide particularly good results. These probes are therefore preferred when a KIR locus is investigated. FIGS. 3C and D provides an extended list of KIR-specific probes which provide even better results than the probes listed in FIGS. 3A and B. Therefore, these probes are even more preferred when a KIR locus is investigated. Further provided is thus a method and/or a use according to the invention, wherein at least one probe depicted in FIG. 3A, 3B, 3C or 3D, preferably in FIG. 3C or 3D, is used. Preferably, at least two probes depicted in FIG. 3 are used. In another preferred embodiment at least four probes, more preferably at least six probes depicted in FIG. 3A, 3B, 3C or 3D are used.

In a particularly preferred embodiment, a probe set of FIG. 3 is used. Said probe set preferably comprises three probes. A probe set of FIG. 3 is formed by two or three individual probes depicted in FIG. 3 which have the same number, followed by the letter A, B, C, D, E, G, K, L, M or N. For instance, probe set 408 is formed by probes 408A, 408B and 408C. Optionally, four different probes with the same number are given for a probe set of FIG. 3. In that case, a left, a middle and a right probe is selected from said four probes. Further provided is therefore a method and/or a use according to the invention, wherein at least one probe set depicted in FIG. 3A selected from the group consisting of probe set 408, probe set 507, probe set 419, probe set 528, probe set 413, probe set 416, probe set 415 and probe set 418 is used. In a particularly preferred embodiment at least one probe set depicted in FIG. 3A selected from the group consisting of probe set 408, probe set 507, probe set 528, probe set 413, probe set 416 and probe set 415 is used. These probe sets contain a third probe which is specific for a (pseudo)gene variant of the KIR locus. Also provided is a method and/or a use according to the invention, wherein at least one probe set depicted in FIG. 3B selected from the group consisting of probe set 409, probe set 506, probe set 507, probe set 538, probe set 417 and probe set 517 is used. In a particularly preferred embodiment at least one probe set depicted in FIG. 3B selected from the group consisting of probe set 409, probe set 506, probe set 507, probe set 538, probe set 417 and probe set 517 is used. These probe sets also contain a third probe which is specific for a (pseudo) gene variant of the KIR locus. Also provided is a method and/or a use according to the invention, wherein at least one probe set depicted in FIG. 3C selected from the group consisting of probe set 415, probe set 703, probe set 413, probe set 419, probe set 702, probe set 711, probe set 408, probe set 507, probe set 710, probe set 528, probe set 418 and probe set 416 is used. In a particularly preferred embodiment at least one probe set depicted in FIG. 3C selected from the group consisting of probe set 415, probe set 703, probe set 413, probe set 419, probe set 702, probe set 711, probe set 408, probe set 507, probe set 710, probe set 528, probe set 418 and probe set 416 is used. These probe sets also contain a third probe which is specific for a (pseudo)gene variant of the KIR locus. Also provided is a method and/or a use according to the invention, wherein at least one probe set depicted in FIG. 3D selected from the group consisting of probe set 506, probe set 417, probe set 517, probe set 409, probe set 507, probe set 710, probe set 709, probeset 708, probe set 704 and probe set 538 is used. In a particularly preferred embodiment at least one probe set depicted in FIG. 3D selected from the group consisting of probe set 506, probe set 417, probe set 517, probe set 409, probe set 507, probe set 710, probe set 709, probeset 708, probe set 704 and probe set 538 is used. These probe sets also contain a third probe which is specific for a (pseudo)gene variant of the KIR locus.

It is preferred to use at least two probe sets selected from FIG. 3, so that various KIR (pseudo)gene variants are screened for with good results. More preferably, at least three probe sets selected from FIG. 3 are used. Even more preferably, at least four, more preferably at least five, most preferably at least six probe sets selected from FIG. 3 are used. Said at least two, three, four, five or six probe sets are preferably selected from the group consisting of probe set 408, probe set 507, probe set 528, probe set 413, probe set 416, probe set 415, probe set 418, probe set 419, probe set 409, probe set 506, probe set 538, probe set 417, probe set 517, probe set 703, probe set 702, probe set 711, probe set 710, probe set 709 and probe set 704 since these probe sets contain a third probe which is specific for a (pseudo)gene variant of the KIR locus. In one embodiment, all probe sets depicted in FIGS. 3A, and/or 3B, and/or 3C, and/or 3D are used. In a preferred embodiment all probe sets depicted in FIG. 3C and/or FIG. 3D are used.

It is of course also possible to modify a sequence of at least one probe depicted in FIG. 3 to some extent. This is for instance done for optimalization purposes. Further provided is therefore a method and/or a use according to the invention, wherein at least one probe is used which has at least 70%, preferably at least 80%, more preferably at least 85%, more preferably at least 90%, most preferably at least 95% sequence identity to a probe depicted in FIG. 3. Preferably, at least two, more preferably at least four, most preferably at least six probes are used which have at least 70%, preferably at least 80%, more preferably at least 85%, more preferably at least 90%, most preferably at least 95% sequence identity to a probe depicted in FIG. 3. In one embodiment, a method or use according to the invention is provided wherein at least 20 probes are used, said at least 20 probes having at least 70%, preferably at least 80%, more preferably at least 85%, more preferably at least 90%, most preferably at least 95% sequence identity to the probes depicted in FIG. 3. A minimum of two specific probes per (pseudo)gene is preferred to determine copy number variation (CNV).

Preferably, probe sets are used which are based on the probe sets depicted in FIG. 3A, 3B, 3C or 3D, preferably based on the probe sets depicted in FIGS. 3C and/or 3D. Said probe set preferably comprises three probes. One or more of the probes of such probe set may be modified to some extent, as described above. Further provided is therefore a method and/or a use according to the invention, wherein at least one probe set is used which has at least 70%, preferably at least 80%, more preferably at least 85%, more preferably at least 90%, most preferably at least 95% sequence identity to a probe set as depicted in FIG. 3. This means that the probes of said probe set have at least 70% sequence identity to the corresponding probes of at least one probe set of FIG. 3. Preferably, a probe set is used which has at least 70%, preferably at least 80%, more preferably at least 85%, more preferably at least 90%, most preferably at least 95% sequence identity to a probe set depicted in FIG. 3 selected from the group consisting of probe set 408, probe set 507, probe set 419, probe set 528, probe set 413, probe set 416, probe set 415, probe set 418, probe set 419, probe set 409, probe set 506, probe set 538, probe set 417, probe set 517, probe set 703, probe set 702, probe set 711, probe set 710, probe set 709 and probe set 704 since these probe sets contain a third probe specific for a KIR nucleic acid sequence. Preferably at least two, more preferably at least three, more preferably at least four, more preferably at least five, most preferably at least six of such probe sets are used, so that various KIR (pseudo)gene variants are screened for with good results.

Novel probes and probe sets which are particularly suitable for (pseudo)gene variant analysis and (pseudo)gene copy number determination of the KIR locus are also provided. These probes and probe sets are listed in FIGS. 3A, B, C and D, as described above. Further provided are therefore probes and probe sets as depicted in FIG. 3A, 3B, 3C or 3D, as well as probes and probe sets which have at least 70%, preferably at least 80%, more preferably at least 85%, more preferably at least 90%, most preferably at least 95% sequence identity to a probe or probe set depicted in FIG. 3A, 3B, 3C or 3D. A mixture of nucleic acids, wherein said nucleic acids comprise at least two probe sets according to the invention is also provided. Preferably, said mixture comprises at least four, more preferably at least six probe sets according to the invention. As said before, such probe sets have at least 70% sequence identity to a probe or probe set depicted in FIG. 3A, 3B, 3C or 3D. One embodiment provides a mixture of nucleic acids comprising at least two, preferably at least four, more preferably at least six probe sets as depicted in FIG. 3A, 3B, 3C or 3D.

Further provided is a kit for detecting the presence of at least one target nucleic acid sequence in a sample, comprising a probe set or a mixture of nucleic acids according to the invention. Said at least one target nucleic acid sequence preferably comprises a nucleic acid sequence present in a KIR locus. A kit according to the invention preferably further comprises a PCR primer set comprising at least 70%, preferably at least 80%, more preferably at least 85%, more preferably at least 90%, most preferably at least 95% sequence identity to nucleic acid sequences 5'-GGGTTC-CCTAAGGGTTGGA and TCTAGATTGGATCTTGCTG-GCAC-3', or the complements thereof. These primers are particularly suitable for amplifying probe sets depicted in FIG. 3.

KIR polymorphisms have been associated with disease. Association between KIR polymorphisms and subtypes of leukemia were investigated by Zhang et al. (Zhang et al. 2009). The presence of KIR2DS4 was demonstrated to be predisposing to chronic myelogenous leukemia (CML) and the absence of KIR2DS3 was predisposing to acute lymphoblastic leukemia (ALL). KIR2DS4 is present in haplotype A, whereas KIR2DS3 is present in haplotype B. Presence of KIR2DS4 and absence of KIR2DS3 are predisposing to leukemia subtypes. Thus, characteristics of haplotype A are predisposing to leukemia subtypes. The present invention provides probes that are particularly well suitable for detecting KIR genes, including KIR2DS4 and KIR2DS3. Thus, with probes according to the present invention selected from FIGS. 3A, 3B, 3C and/or 3D the presence and/or absence of KIR2DS4 and KIR2DS3 in a sample is particularly well determined. Preferably probesets 540A/540C, and/or 513B/513D and/or 504A/504B, and/or 708K/708L/708M/708N as depicted in FIGS. 3C and/or 3D are used to detect KIR2DS3 and/or KIR2DS4 polymorphisms. With probes selected from FIG. 3 predisposition to leukemia subtypes is thus particularly well determined.

Therefore, in one embodiment the invention provides a method for determining predisposition to leukemia of an individual comprising determining the presence or absence of KIR2DS4 and/or KIR2DS3 in a nucleic acid sample of said individual with at least one probeset listed in FIGS. 3A, 3B, 3C and/or 3D, wherein the presence of KIR2DS4 is indicative for a predisposition for chronic myelogenous leukemia and the absence of KIR2DS3 is indicative for a predisposition for acute lymphoblastic leukemia. In a preferred embodiment probe set 540A/540C, and/or 513B/513D and/or probe set 504A/504B, and/or 708K/708L/708M/708N as depicted in FIGS. 3C and/or 3D are used for determining the presence or absence of KIR polymorphisms. As used herein, the term "nucleic acid sample" means a sample comprising nucleic acid. Said sample may of course further comprise other components, such as for instance proteins. Preferably, nucleic acid is at least partly isolated from said sample before being subjected to a method according to the present invention.

Association between KIR polymorphisms and inflammatory bowel disease (IBD) and/or Crohn's disease have been established as well (Hollenbach et al 2009). The KIR2DL2/ KIR2DL3 heterozygous genotype predisposes or protects from Crohn's disease depending on the presence of their HLA-C ligands. KIR2DL2/KIR2DL3 heterozygosity in combination with C1 predisposes to Crohn's disease whereas KIR2DL2/KIR2DL3 heterozygosity in combination with C2 protects from IBD and/or Crohn's disease. KIR2DL2/ KIR2DL3 heterozygosity in combination with C1/C2 heterozygosity has an intermediate effect on predisposition (Hollenbach et al 2009). Non-limiting examples for determining the presence or absence of C1 and/or C2 are detecting nucleic acid sequence(s) encoding C1 and/or C2 protein using for instance a nucleic acid amplification reaction or detecting C1 and/or C2 protein using for instance Western blot analysis.

The present invention provides probes that are particularly suitable for detecting KIR genes, including KIR2DL2 and KIR2DL3. Thus, with probes according to the present invention selected from FIGS. 3A, 3B, 3C and/or 3D KIR2DL2/ KIR2DL3 heterozygosity in a sample is particularly well determined. Preferably probeset 415B/415C/415D and/or 417A/417B/417C and/or probeset 420A/420B, and/or 706A/ 706B as depicted in FIGS. 3C and/or 3D are used to detect KIR2DL3 and/or KIR2DL2 polymorphisms. With probes selected from FIG. 3 predisposition to Crohn's disease is thus particularly well determined.

Therefore, in one embodiment the invention provides a method for determining predisposition to IBD and/or Crohn's disease of an individual comprising determining the presence or absence of KIR2DL2 and/or KIR2DL3 in a nucleic acid sample of said individual with at least one probeset listed in FIGS. 3A, 3B, 3C and/or 3D, and determining the presence of absence of HLA C1 and/or C2 ligand in a sample of said individual, wherein KIR2DL2, KIR2DL3 heterozygosity in combination with C1 homozygosity is indicative for a predisposition for Crohn's disease, and KIR2DL2, KIR2DL3 heterozygosity in combination with C2 homozygosity is indicative for protection for Crohn's disease. In a preferred embodiment probe set 415B/415C/415D and/or 417A/417B/ 417C and/or probe set 420A/420B and/or 706A/706B as depicted in FIGS. 3C and/or 3D are used for determining the presence or absence of KIR polymorphisms.

Copy number variation of KIR2DL3, KIR3DL1 and KIR3DS1 is correlated to the course of disease in chronic infection, such as retroviral infection, herpes virus infection, and hepatitis virus infection, more in particular HIV, CMV, EBV, HSV, HBV and HCV (Martin et al 2007 and Khakoo et al 2004). A higher copy number of KIR3DL1 and/or KIR3DS1 in an individual is indicative for an improved course of the disease and/or response to treatment of chronic infection as compared with a low copy number of KIR3DL1 and/or KIR3DS1 in an individual and a low copy number of KIR2DL3 in an individual is indicative for an improved course of the disease and/or response to treatment of chronic infection as compared with a high copy number of KIR2DL3 in an individual. Thus, a higher copy number of KIR3DL1 and/or KIR3DS1 in an individual is indicative for an increased survival in chronic infection and a lower copy number of KIR2DL3 in an individual is indicative for increased survival in chronic infection.

The present invention provides probes that are particularly well suitable for determining copy number variation of KIR genes, including KIR3DL1 and KIR3DS1. Thus, with probes according to the present invention selected from FIGS. 3A, 3B, 3C and/or 3D the copy number of KIR3DL1 and KIR3DS1 and KIR2DL3 in a sample is particularly well determined. Preferably probe sets 409A/409B/409C, and/or 711A/711B/711C/711D and/or 418A/418B/418D, and/or 709C/709D/709E/709G and/or probe set 415B/415C/415D and/or 417A/417B/417C as depicted in FIGS. 3C and/or 3D are used to estimate the copy number of KIR3DL1 and/or KIR3DS1 and/or KIR 2DL3. With probes selected from FIG. 3 susceptibility of an individual to course of disease and/or response to treatment in chronic infection is thus particularly well determined.

Therefore the invention provides method for determining susceptibility of an individual to course of disease and/or response to treatment in chronic infection, preferably retroviral infection, herpes virus infection, and hepatitis virus infection, comprising determining the copy number of KIR2DL3, KIR3DL1 and/or KIR3DS1 in a nucleic acid sample of said individual with at least one probeset listed in FIG. 3A or 3B or 3C or 3D, wherein a high KIR3DL1 and/or KIR3DS1 copy number in an individual is indicative for an improved course of disease and/or response to treatment of chronic infection as compared with a low copy number of KIR3DL1 and/or KIR3DS1 in an individual and a low KIR2DL3 copy number in an individual is indicative for an improved course of disease and/or response to treatment of chronic infection as compared with a high copy number of KIR2DL3 in an individual. Preferably said chronic infection comprises HIV, CMV, EBV, HSV, HBV and HCV. In a preferred embodiment probeset 409A/409B/709D/409C, and/or 711A/711B/711C/711D and/or 418A/418B/418D, and/or 709C/709E/709G and/or probe set 415B/415C/415D and/or 417A/417B/417C as depicted in FIGS. 3C and/or 3D are used for determining the copy number of KIR genes.

The presence of KIR2DS4 in a donor is correlated to transplantation-related outcome measures, such as mortality, graft-versus-host, graft-versus-tumor and grafted organ survival in recipients after transplantation. The presence of KIR2DS4 in a donor is indicative for reduced mortality, reduced graft-versus-host, increased graft-versus-tumor and increased grafted organ survival in recipients after transplantation as compared to the absence of KIR2DS4 in a donor. The present invention provides probes that are particularly well suitable for determining copy number variation of KIR genes, including KIR3DL1 and KIR3DS1. Thus, with probes according to the present invention selected from FIGS. 3A, 3B, 3C and/or 3D the copy number of KIR2DS4 in a sample is particularly well determined. Preferably probe sets 504A/ 504B, and/or 708K/708L/708M/708N as depicted in FIGS. 3C and/or 3D are used to the presence or absence of KIR2DS4. With probes selected from FIG. 3 predisposition to transplantation-related outcome measures is thus particularly well determined Therefore the invention provides a method for determining predisposition to transplantation-related outcome measures, such as mortality, graft-versus-host, graft-versus-tumor and grafted organ survival of a recipient after transplantation, comprising determining the presence or absence of KIR2DS4 in a nucleic acid sample of a donor for said recipient with at least one probeset listed in FIG. 3A or 3B or 3C or 3D, wherein the presence of KIR2DS4 in said donor is indicative for a reduced mortality, a reduced graft-versus-host reaction, an increased graft-versus-tumor reaction and an increased grafted organ survival in said recipient as compared to the mortality, graft-versus-host reaction, graft-versus-tumor reaction and grafted organ survival of a recipient with a donor wherein KIR2DS4 is absent. In a preferred embodiment probeset 504A/504B, and/or 708K/708L/708M/708N as depicted in FIGS. 3C and/or 3D are used for determining the presence or absence of KIR polymorphisms.

A correlation has been established between the copy number of KIR2DL2 and KIR2DS2 and rheumatoid arthritis (RA) with extra-articular manifestations and rheumatoid vasculitis. A higher copy number of KIR2DL2 and/or KIR2DS2 in an individual was demonstrated to be predisposing for rheumatoid arthritis with extra-articular manifestations and rheumatoid vasculitis (Majorczyk et al 2007, Yen et al 2001). Additionally, rheumatoid arthritis patients positive for KIR2DL3 and negative for KIR2DS3 had earlier disease diagnosis (Majorczyk et al 2007).

The present invention provides probes that are particularly well suitable for determining the presence or absence and copy number variation of KIR genes, including KIR2DL2, KIR2DS2, KIR2DL3 and KIR2DS3. Thus, with probes according to the present invention selected from FIGS. 3A, 3B, 3C and/or 3D the presence or absence and copy number of KIR2DL2, KIR2DS2, KIR2DL3 and KIR2DS3 in a sample is particularly well determined. Preferably probe sets 420A/420B, and/or 706A/706B and/or probe set 703A/703B/703C, and/or 544A/544B as depicted in FIGS. 3C and/or 3D are used to estimate the copy number of KIR2DL2 and/or KIR2DS2. Preferably probe sets 415B/415C/415D and/or 417A/417B/417C and/or probe set 513B/513D and/or 540A/540C as depicted in FIGS. 3C and/or 3D are used to estimate the copynumber of KIR2DL3 and/or KIR2DS3. With probes selected from FIG. 3 susceptibility of an individual to rheumatoid arthritis (RA) with extra-articular manifestations and rheumatoid vasculitis is thus particularly well determined.

Therefore in one embodiment the invention provides a method for determining predisposition to rheumatoid arthritis with extra-articular manifestations and rheumatoid vasculitis of an individual comprising determining the copy number of KIR2DS2 and/or KIR2DL2 in a nucleic acid sample of said individual with at least one probeset listed in FIGS. 3A, 3B, 3C and/or 3D, wherein a high copy number of KIR2DS2 and/or KIRDL2 in said individual is indicative for a predisposition for rheumatoid arthritis with extra-articular manifestations and rheumatoid vasculitis as compared with a low copy number of KIR2DL2 and/or KIR2DS2 in an individual. In a preferred embodiment probeset 420A/420B, and/or 706A/706B and/or probe set 703A/703B/703C, and/or 544A/544B as depicted in FIGS. 3C and/or 3D are used for determining the copy number of KIR genes.

Finally, a correlation has been found between the presence or absence or copy number of KIR genes and predisposition to autoinflammation, such as HLA-B27-related enthesitis-related arthropathy and reactive arthritis, psoriasis, in individuals. For instance, KIR3DL2 is increased in spondylarthritides and juvenile enthesitis-related arthritis (Chan et al 2005, Brown 2009). The present invention provides probes that are particularly well suitable for determining the presence or absence and copy number variation of KIR genes. Thus with probes selected from FIG. 3 susceptibility of an individual to autoinflammation, such as HLA-B27-related enthesitis-related arthropathy and reactive arthritis, psoriasis is particularly well determined.

Therefore, in one embodiment the invention provides a method for determining predisposition to autoinflammation, preferably HLA-B27-related enthesitis-related arthropathy and reactive arthritis, psoriasis, in individuals comprising a) determining the presence or absence and/or copy number of a KIR gene indicative for said disorder in a nucleic acid sample of said individual with at least one probeset listed in FIG. 3A or 3B or 3C or 3D, and b) correlating the result obtained in step a) with presence or absence of said predisposition.

In another embodiment the invention provides a method for determining predisposition to spondylarthritides and/or juvenile enthesitis-related arthritis of an individual comprising determining the copy number of KIR3DL2 in a nucleic acid sample of said individual with at least one probeset listed in FIGS. 3A, 3B, 3C and/or 3D, wherein a high copy number of KIR3DL2 in said individual is indicative for a predisposition for spondylarthritides and/or juvenile enthesitis-related arthritis as compared with a low copy number of KIR3DL2 in an individual. In a preferred embodiment probeset 404A/404B, and/or 538A/538B/538D as depicted in FIGS. 3C and/or 3D are used for determining the copy number of KIR genes.

The invention is further explained in the following examples. These examples do not limit the scope of the invention, but merely serve to clarify the invention.

```
                                              (SEQ ID NO: 153)
1a gcctggttgg acagatcca;

(SEQ ID NO: 154)
1a ctctaaggac ccctcacgcc tcgttggaca gatcca;

(SEQ ID NO: 155)
1b gcctggttgg acgatcca;

(SEQ ID NO: 156)
1b ctctaaggac ccctcacgcc tcgttggacg atcca;

(SEQ ID NO: 157)
1  cccatgatgc ttgcccttgc agrg;

(SEQ ID NO: 158)
1  cccatgatgc ttgcccttgc agrgacctac agatgctacg gttc;

(SEQ ID NO: 163)
1  cccatgatgc ttgcccttgc agggacctac agatgctacg gttc;

(SEQ ID NO: 8)
2  cgcatgacac aagacctggc aggg;

(SEQ ID NO: 9)
3  cgcatgaggc aagacctggc aggg;

(SEQ ID NO: 10)
4  cccatgatgg aagacctggc aggg;

(SEQ ID NO: 11)
5  cgcatgacgc aagacctggc aggg;
```

-continued

```
6  cgcatgaagc aagacctggc aggg;                (SEQ ID NO: 12)

7  cccatgatgc ctgtccttgc agga;                (SEQ ID NO: 13)

8  tccatgatgc gtgcccttgc aggg;                (SEQ ID NO: 14)

9  cccatgatgc aagaccttgc aggg;                (SEQ ID NO: 15)

10 cgcatgacgc aagaccttgc aggg;                (SEQ ID NO: 16)

11 cccttgatgc ctgtccttgc agga;                (SEQ ID NO: 17)
and 12 cccatgacac ctgcccttgc aggg.                (SEQ ID NO: 18)
```

FIG. 2. IUB nucleotide codes of degenerate bases

FIG. 3 KIR-specific probe sets. A) KIR probe mix 1. Bold nucleotides represent probes that are part of a probe set consisting of three probes used for detection of two SNPs, B) KIR probe mix 2. Bold nucleotides represent probes that are part of a probeset consisting of three probes used for detection of two SNPs, C) extended KIR probe mix 1. Bold nucleotides represent primer binding sites. KIR genes in which two SNPs are detected using one probe set according to the invention, consisting of three probes are depicted in FIG. 13, D) extended KIR probe mix 2. Bold nucleotides represent primer binding sites. KIR genes in which two SNPs are detected using one probe set of this probe mix, consisting of three probes are depicted in FIG. 13, E) control probe mix.

Figure 4:
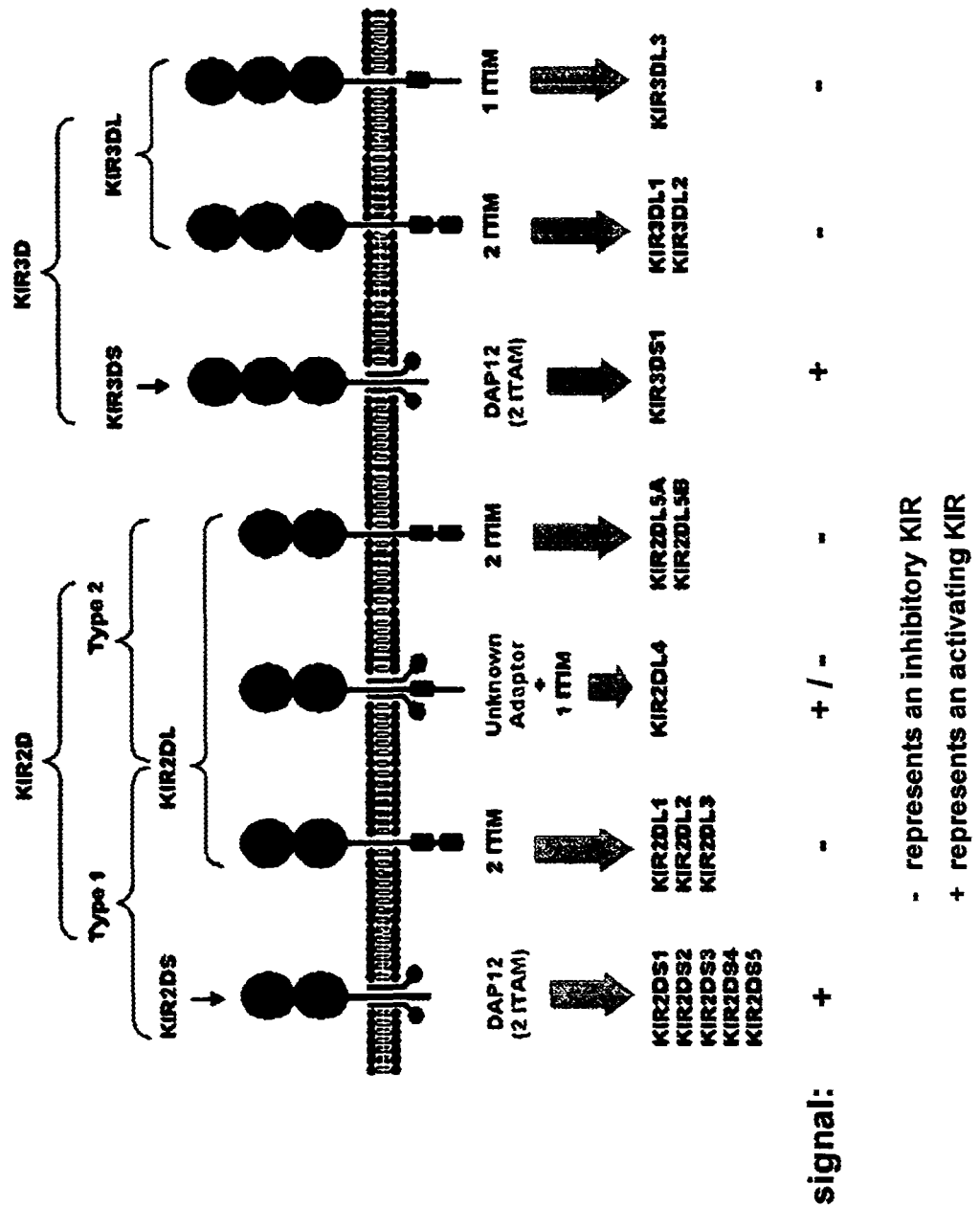

FIG. 4. The KIR protein structures. Depicted as large ovals are the extracellular Ig-like domains, as squares the ITIMs and as small light grey circles the charged residues on the cytoplasmic tail (IPD KIRdatabase). Inhibitory KIRs and activating KIRs are indicated by a "+" and "−", respectively.

Figure 5:
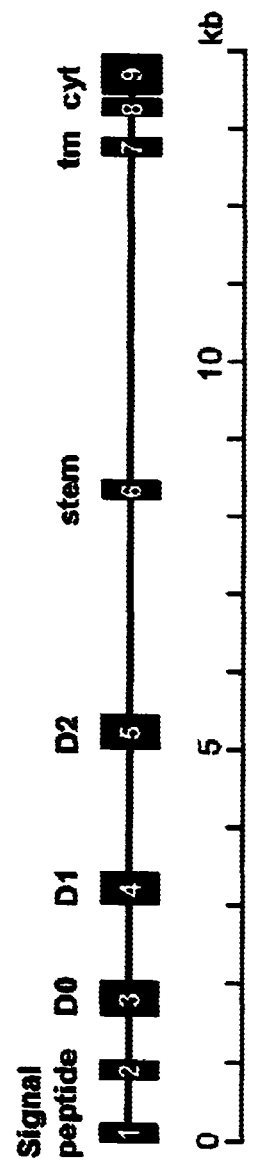

FIG. 5. Exon structure of KIR3DL1. Exons are depicted with black boxes and introns with lines and are draw approximately to scale (Vilches et al, 2002).

Figure 6:
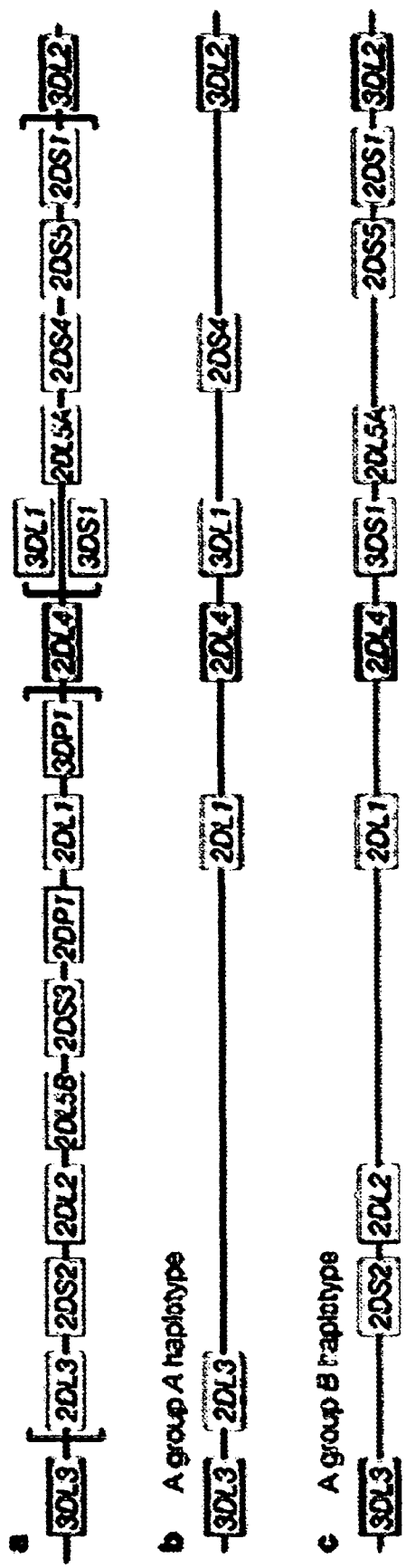

FIG. 6. The organization of KIR locus. a: Framework genes KIR3DL3, KIR2DL4 and KIR3DL2 are in black and are found at the beginning, near the middle and at the end of the locus. The pseudogenes KIR2DP1 and KIR3DP1 (which is also a framework gene) in white and black, respectively, and the regions between the framework genes are variable and these KIR genes are in grey, with activating KIRs with black letters and inhibitory KIRs in white. b: One example of haplotype A. c: An example of haplotype B (Parham et al, 2003).

Figure 7:
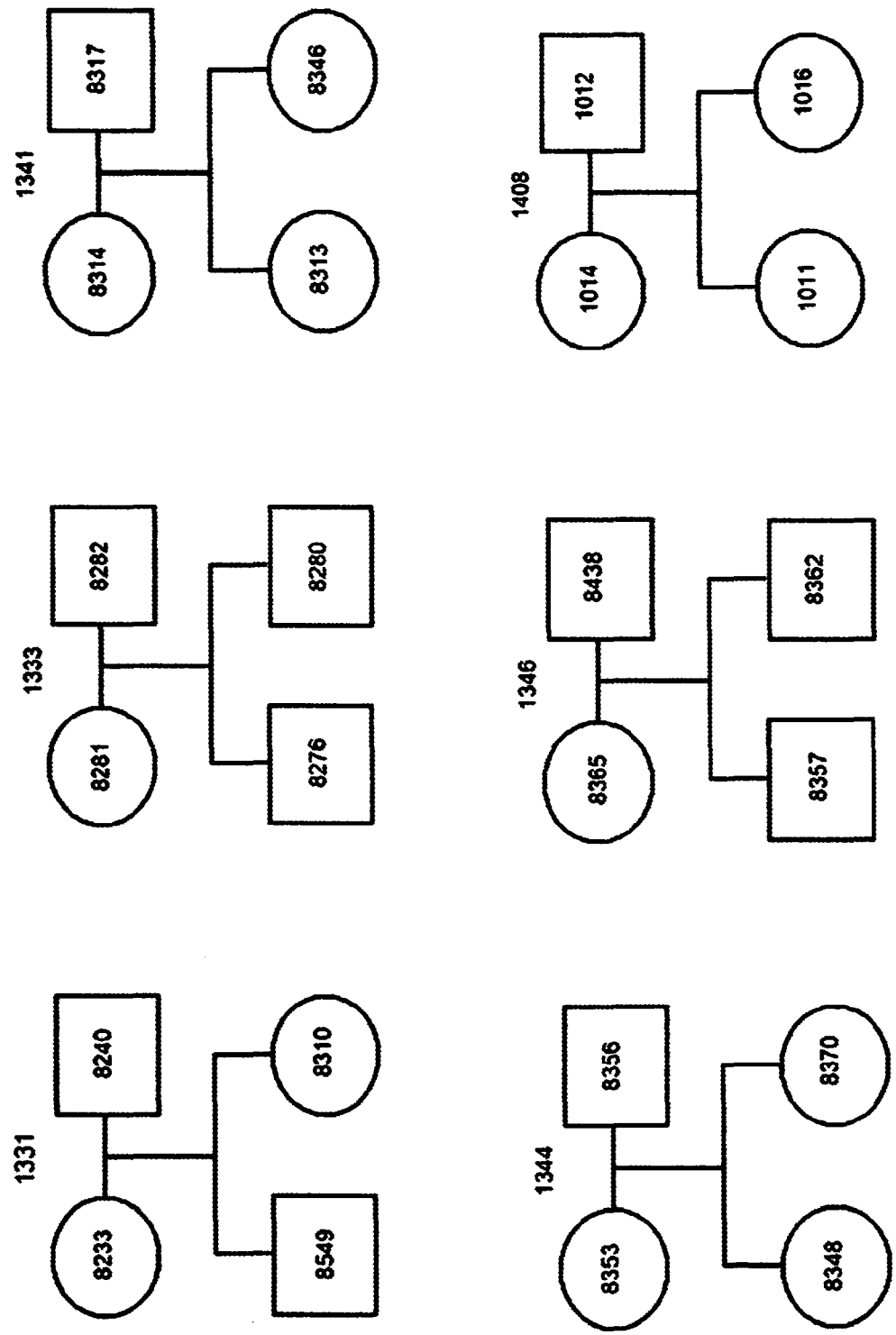

FIG. 7. The pedigrees of 12 families from the KIR reference panel I (the families 1347 and 1349 are depicted in FIGS. 11 and 12, respectively). The four numbers on top of the pedigree is the CEPH family number and the numbers in the shapes is the individual number, these numbers correspond with the numbers in table 4. The letters below the shape indicates the haplotypes and can be found in the legend next to the pedigree.

Figure 8:
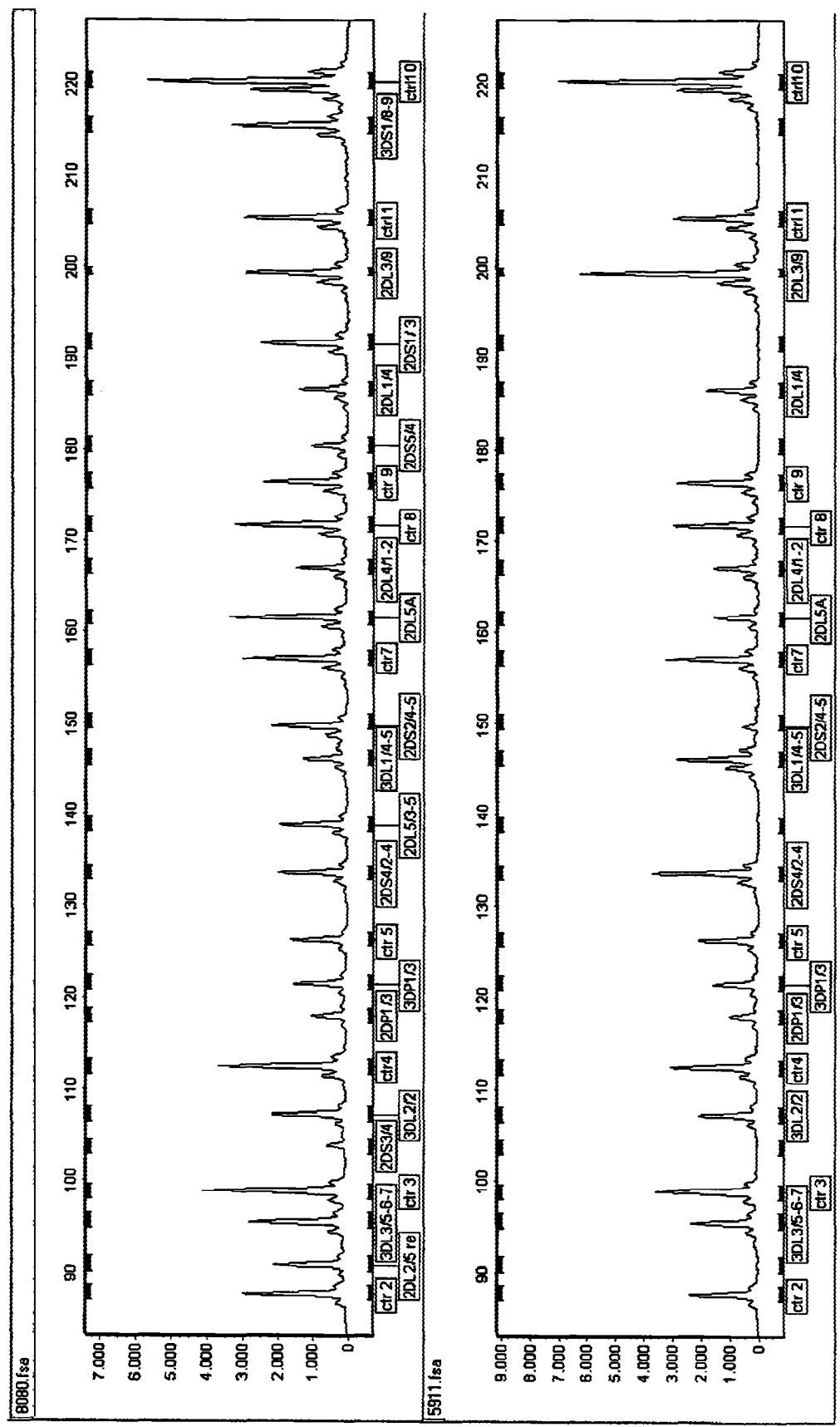

FIG. 8. Electropherogram of probe set 1. The peak patterns of the probes on two donors: 8080 (top) and 5911 (bottom). All 17 KIR probe peaks are present on donor 8080 and 10 KIR probe peaks on donor 5911. In all donors the nine control probes (Ctr2-10) and the probes on the four framework genes: KIR3DL3, KIR3DP1, KIR3DL2, and KIR2DL4 (indicated with the black arrows) generated a signal. Electropherogram of probes set 2 were similar for these two probe groups (data not shown).

Figure 9:
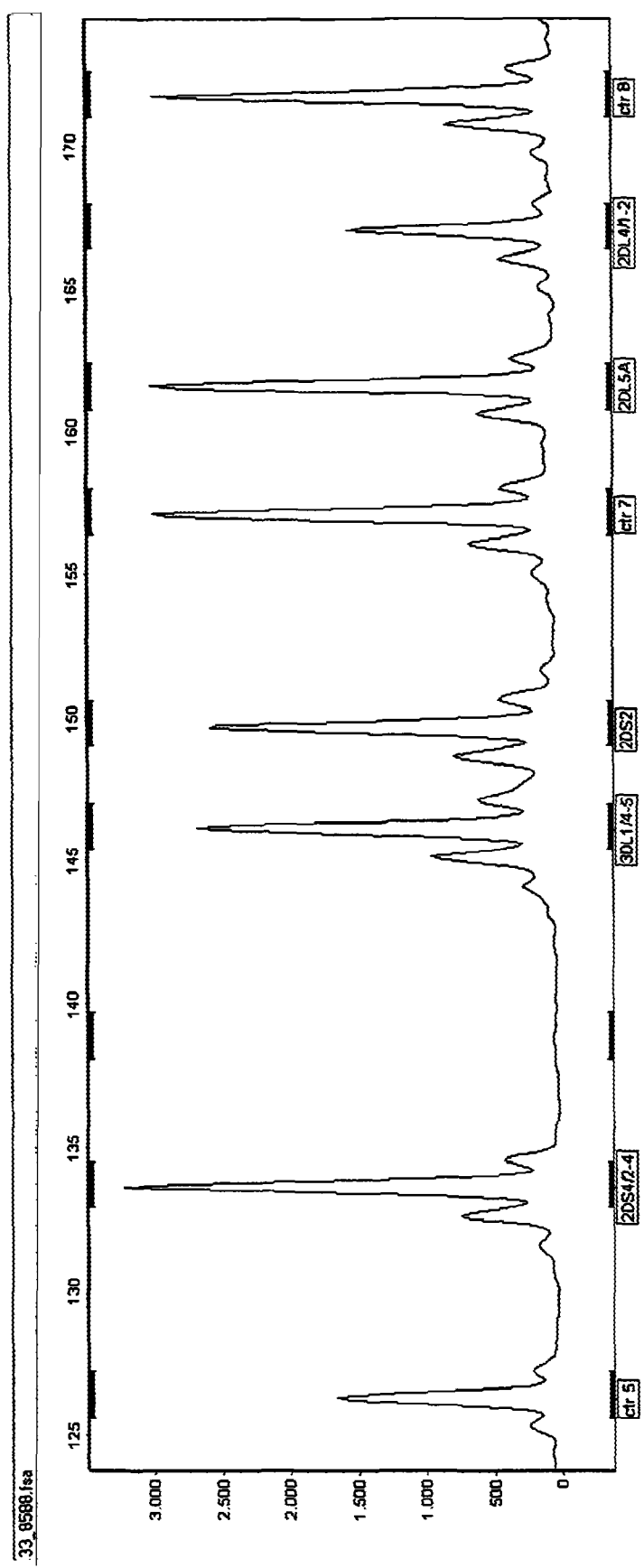

FIG. 9. Comparison of peak intensities of the probe 2DS2 (black arrows) between a true positive for KIR2DS2 (top) and a false positive (bottom).

Figure 10:
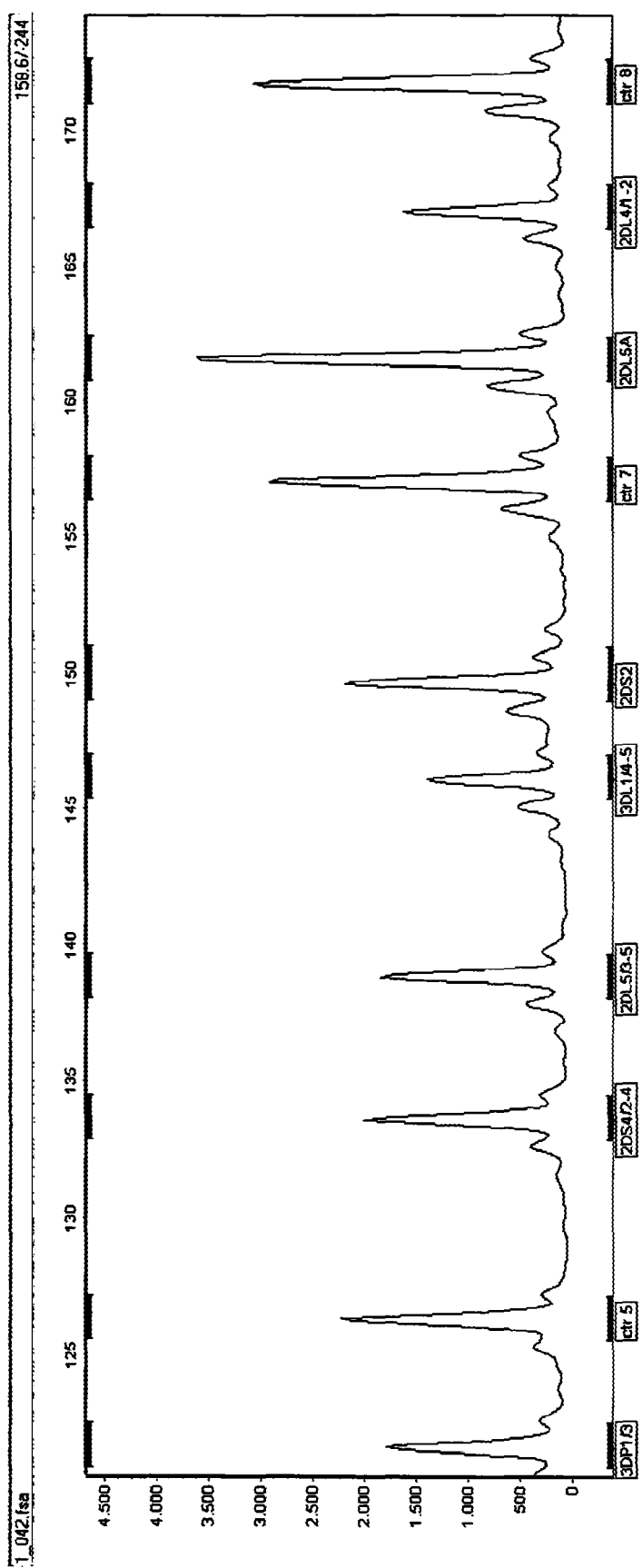

FIG. 10. The peak profiles of the probes 2DL5 (left arrows) and 2DL5A (right arrows). Top: a sample which is positive for KIR2DL5 indicated by the presence of the peak from probe 2DL5 and the peak from 2DL5A cannot be distinguished in the presence of KIR2DL5A or 3DP1*004. Bottom: this sample is negative for KIR2DL5 indicated by the absence of the probe 2DL5 and the peak of 2DL5A indicates the presence of KIR3DP1*004.

FIG. 11. The pedigree of family 1347.
A) Left: The numbers of the individuals in top left pedigree correspond with the numbers of the DNA samples in the table. At the bottom the haplotype is denoted in letters and the legend for the haplotype is displayed below. The CNV of some of the genes where quantified different by each of the two probe sets, the number before '/' is for probe set 1 and after for probe set 2.
B1) Interpretation based on SSP-PCR data from CEPH-IHWG and the conventional KIR haplotype model.
B2) Novel haplotype model based on SSP-PCR data obtained from CEPH-IHWG.
B3) Copy number variation of KIR genes, determined using SSP-PCR data obtained from CEPH-IHWG based on the conventional KIR haplotype model (table 1) and the novel KIR haplotype model (table 2) and copy number variation of KIR genes, determined by KIR-MLPA using the extended probe sets 1 and 2 and the novel KIR haplotype model (table 3).

FIG. 12. The pedigree of family 1349.
A) Left: The numbers of the individuals in top left pedigree correspond with the numbers of the DNA samples in the table. At the bottom the haplotype is denoted in letters and the legend for the haplotype is displayed below. The CNV of some of the genes where quantified different by each of the two probe sets, the number before '/' is for probe set 1 and after for probe set 2.
B1) Interpretation based on SSP-PCR data from CEPH-IHWG and the conventional KIR haplotype model.
B2) Novel haplotype model based on SSP-PCR data obtained from CEPH-IHWG.
B3) Copy number variation of KIR genes, determined using SSP-PCR data obtained from CEPH-IHWG based on the conventional KIR haplotype model (table 1) and the novel KIR haplotype model (table 2) and copy number variation of KIR genes, determined by KIR-MLPA using the extended probe sets 1 and 2 and the novel KIR haplotype model (table 3).

FIG. 13. Detection of KIR alleles and KIR copy number variation.

EXAMPLES

Example 1

This Example presents a new method for KIR genotyping.

KIRs are expressed by natural killer (NK) cells and a subset of T cells. NK cells are cells of the lymphoid lineage, but display no antigen-specific receptors. Their main function is to monitor host cells for the presence of MHC class I molecules and this is important for e.g. distinguishing healthy cells from virus-infected or tumors cells. A low expression of MHC class I molecules on host cells, which may for instance occur during viral infections as a result of virus-mediated down regulation to prevent presentation of viral peptides to CD8 T cells, stimulate NK cells to launch cytotoxic attack. This phenomenon is also known as the "missing self" theory.

NK cells express a variety of receptors that mediate interactions with MHC class I molecules, including members of the KIRs and CD94/NKG receptor multigene families. Interaction between MHC class I molecules and these receptors regulates NK cytotoxicity generally through the generation of inhibitory signals. The composition between KIR and CD94/NKG families of humans and mice differs considerably, with KIRs constituting the most in genetic and gene number variation in man.

KIRs were first discovered in their role in fighting virus infections by natural killer cells, but they are also expressed by a subset of T cells. The KIR gene cluster is located at chromosome 19q13.4 within the leukocyte receptor complex (LCR) and spans a region of about 150 kb. Up to 15 genes plus two pseudogenes have been identified to date. Characteristic of the KIR gene cluster is the variable gene content and an extensive degree of allelic gene variants. The gene content between unrelated individuals can differ considerably in the amount of KIR (pseudo)genes present, but also in the numbers of activating and inhibitory (pseudo)genes. Contractions and expansions by non-reciprocal recombination are the major mechanism behind KIR diversification. KIRs can be divided into two haplotypes, A and B in which haplotype B has a greater variety in gene content and contains more activating KIR genes. Studies of different ethnic populations show significant differences in the distribution of these two haplotypes. The selective pressures, such as exposure to different pathogens and rapidly evolving MHC class I molecules appear to be the forces behind such a gene diversification. A functional analog is the Ly49 gene family in mice, but KIRs and Ly49 are structurally distinct proteins. KIRs have been identified in different primate species, but they are species-specific and differ in gene content among various species. These findings provide evidence for a rapid evolution and expansion of this gene family.

Another level of relevant variation is the level of expression of KIRs by individual NK cells. Each NK cell expresses only a subset of its KIR gene repertoire and the presence of HLA ligands seems to influence the frequency of NK cells expressing the cognate ligand. A higher frequency of NK cells expressing inhibitory KIRs in individuals have been found, when their cognate HLA ligand is present. The ligands of some KIRs, in particular those with activating potential remain to be determined.

Some of these activating KIRs seem to have lower affinity for their cognate HLA class I ligands in comparison with their related inhibitory receptors.

KIRs have been associated with several diseases, but due to the genetic diversity between and in populations and the differences in KIR expression by NK cells, a clear understanding of their role has yet to be defined. KIRs have been reported to play a role in allogeneic hematopoietic stem cell transplantation (HSCT), which is used in the treatment of leukemia. It was suggested that an intentional mismatch between donor KIR and recipient HLA ligands would allow for a graft anti-tumor effect. KIR3DS1 and KIR3DL1 have been reported to be associated with slower progression to AIDS and several other virus infections, such as Hepatitis C virus (HCV), human cytomegalovirus (CMV). Also the protozoan infection with *Plasmodium falciparum* implicated roles for KIRs in malaria. In autoimmune and inflammatory conditions, certain KIRs and cognate ligand potentially results in higher susceptibility or protection of the host.

The KIR Gene Cluster

The KIR acronym originally stood for killer cell-inhibitory receptor, because the first KIR discovered had an inhibiting effect on NK cells. To date, KIR is an abbreviation for Killer-cell Immunoglobulin-like Receptor, as this family includes both inhibitory and activating receptors. The HUGO Genome Nomenclature Committee (HGNC) is responsible for the naming of KIR genes. Currently KIR gene family consists of 15 genes and 2 pseudogenes, listed in Table 1 (Marsh et al, 2002). KIR genes are named after the protein structure they encode. The "D" denotes "Domain" and the number 2 or 3 before it indicates the number of extracellular Ig-like domains. "L" indicates a "Long" cytoplasmic tail and "S" indicates a "Short" cytoplasmic tail and the "P" indicates a "pseudogene". The number behind the letter L or S denotes the gene encoding for this structure. Thus KIR2DL1 encodes for a structure with two Ig-like domains and a long cytoplamic tail. KIR2DL5A and KIR2DL5B are exceptions; they were initially identified as one gene KIR2DL5. However these two structurally similar variants are discovered to be located on different regions of the KIR gene cluster and can be inherited separately (Gomez-Lozano et al, 2002).

The KIRs that possess long cytoplasmic tails transduce inhibitory signals to the NK cell, owing to the two immunoreceptor tyrosine-based inhibitory motifs (ITIMs) (FIG. 4). Binding of these receptors with HLA class I molecules leads to phosporylation of the tyrosine residues within the ITIM. Tyrosine phosphatase (SHP-1) is then recruited and activated by the ITIM and prevents or inhibits phosporylation events which are associated with cellular activation. NK-cell mediated cytotoxicity and cytokine secretion inhibition are the main downstream effects. Short cytoplasmic tails lack the ITIM and possess a basic charged amino acid, such as lysine in the transmembrane domain. This positively charged amino acid residue allows association with an adaptor molecule, such as DAP12. DAP12 has one immunoreceptor tyrosine-based activation motif (ITAM). When the tyrosine residues in the ITAM are phosporylated a docking site for SH2 domain of ZAP70 and Syk tyrosine kinase is generated. The action of these kinases triggers a downstream transduction cascade that promotes NK-mediated cytolysis (Middleton et al, 2005). KIR2DL4 is unique among KIRs, as it possesses a long cytoplasmic tail with a charged amino acid arginine in the transmembrane region. KIR2DL4 might therefore be capable of eliciting both activating as well as inhibitory signals.

Exon and Intron Structure

The KIR3DL1 and KIR3DL2, with three extracellular Ig-like domains represent the prototypical KIR from which all the others can be derived. KIR genes are organized in nine exons, the order of these exons corresponding to the different functional regions of the protein (FIG. 5). The first two exons encode the signal peptide, exons 3, 4 and 5 encode the Ig-like domain, D0, D1 and D2, respectively. Exon 6 encodes the stem or linker that connects the D2 domain with the transmembrane region that is encoded by exon 7. Exons 8 and 9 encode the cytoplasmic tail. Type 1 KIRs have two Ig-like domains D1 and D2, KIR2DL1-3 and KIR2DS1-5. The protein products of type 1 lack the D0 domain because exon 3 is a pseudo-exon. This exon is spliced out of the RNA transcript, possibly due to a three-base-pair deletion. Type 2 KIRs have the D0 and D2 domains, KIR2DL4-5, exon 4 is absent in these KIR genes, resulting in a protein without D1 domain.

In KIR2DP1 exon 3 is a pseudoexon and exon 4 has an early stop codon. If KIR2DP1 would be transcribed this could result in a KIR protein with only a single Ig (D2) domain. In KIR3DP1 exon 2 is missing due to a deletion. The exons encoding for the stalk, TM and cytoplasmic regions are also absent. The three exons coding for the Ig-like domains are intact, however the leader sequence is missing. No transcripts have been found for KIR2DP1 (Trowsdale et al, 2001) and KIR3DP1, the latest one is normally silent, but a recombination of KIR2DL5A and KIR3DP1 have been found to be transcribed and is predicted to be secreted rather than anchored to the cell membrane (Gomez-Lozano, 2005).

Genotypes

Uhrberg et al. (Uhrberg et al, 1997) identified that the KIR locus in humans appeared to be polygenic and polymorphic. Individuals have a variable KIR gene content, achieved through differences in number of total KIR genes and differences in the amount of activating and inhibitory KIR genes. The mechanism behind the KIR diversification is non-reciprocal recombinations between non-allelic genes leading to expansion and contractions of the KIR locus. Also reciprocal crossing over events are postulated to contribute to the diversity. The KIR locus can be separated into two parts with KIR3DL3 on the centromeric end and the central KIR3DP1 on one half, and KIR2DL4 in the central and KIR3DL2 on the telomeric end on the other half. Inside these two parts of KIR locus, genes are located that are in much stronger linkage disequilibrium, supporting a homologous recombination event (Uhrberg 2005).

Studies worldwide using genomic DNA to determine the presence or absence of KIR genes in populations have contributed to an extensive amount of KIR-genotype profiling data. These studies show a difference in frequency of KIR genes in populations of different ethnic backgrounds. The methods used for KIR genotyping are polymerase chain reaction with sequence-specific primers (PCR-SSP), sequence-specific oligonucleotide probes, PCR (PCR-SSOP), multiplex PCR, automated sequencing and mass spectrometry.

Haplotypes

KIR genes can be divided in the haplotypes A and B (Carrington et al, 2003). Both haplotypes contain the framework genes KIR3DL3, KIR3DP1, KIR2DL4 and KIR3DL2. These genes are conserved and are virtually present in every individual. Haplotype A is uniform in terms of gene content and is composed of five inhibitory genes (KIR3DL3, KIR2DL3, KIR2DL1, KIR2DL4KIR3DL1 and KIR3DL2, and only one activating KIR2DS4, as shown in FIG. 6. However the central framework gene KIR2DL4 may have an activating function. On the other hand, there are haplotypes A that possess null variants of both KIR2DS4 and KIR2DL4 that are not expressed on the cell surface and technically these haplotypes contain virtually no functional activating KIR.

Haplotype B is more variable than haplotype A and is characterized by one or more of the following genes: KIR2DS2, KIR2DL2, KIR2DL5, KIR2DS3, KIR3DS1, KIR2DL5A, KIR2DS5 and KIR2DS1, conversely haplotype A is characterized by the absence of these genes. The frequency of both haplotypes is relatively even among populations of different ethnic background. It is possible that some haplotypes cannot be placed in these two categories, as the definition of haplotypes varies between authors and hybrids of haplotypes are possible (Vilches et al, 2002). Distinction between A and B haplotypes is useful in biological and medical settings, as haplotype B have more genes that encode for activating KIR than haplotype A. The haplotypes have been constructed by family segregation analysis, genomic sequencing and gene-order analysis (Shilling et al, 2002). FIG. 6 depicts the organization of a KIR locus.

Gene Variation

Adding another level of genetic diversity to the KIR family is the extensive degree of gene variations, which are exhibited by all KIR genes. Allelic diversity is generated by substitutions of nucleotides, recombination or gene conversion and point mutations. Activating KIRs and inhibitory KIRs share a high sequence homology. Activating KIRs are believed to be derived from inhibitory KIRs by alterations in sequence, creating a charged residue upstream of a stop codon and an elimination of ITIMs. Due to their younger evolution, allelic diversity of activating KIRs is quite limited when compared to inhibitory KIRs, but the variation of activating receptors across ethnic populations is more extensive.

Currently a total of 335 KIR alleles have been identified. KIR allele sequences are denoted by an asterisk after the gene name. Differences in the encoded protein sequences are distinguished by the first three digits, the next two digits are used to denote alleles that differ by synonymous differences within the coding sequence (i.e. not resulting in amino acid substitutions) and the last two digits are used for alleles that have differences in the noncoding region, such as introns and promoters. Thus, 3DL1 *009 and 3DL1 *010 are alleles that encode different protein products and 3DL1 *00101 and 3DL1 *00102 are alleles that encode the same protein product, but these alleles differ by a synonymous DNA substitution within the coding region (Marsh et al, 2002).

Expression and HLA

The ligands for inhibitory KIRs are MHC class I molecules, which are constitutively expressed by most healthy cells, but can be down-regulated in tumors and infected cells allowing killing by NK cells. Interaction of MHC with inhibitory receptors ensures tolerance of NK cells towards self. MHC class I molecules are encoded by human leukocyte antigen (HLA) genes that are located at chromosome 6p21.3 and are polymorphic and display significant variations. KIR genes and HLA genes segregate independently during meiosis, because they are located on different chromosomes. This can lead to interesting HLA and KIR combinations inherited by one individual, but to obtain a functional interaction between receptor and the cognate ligand, they need to be expressed together. This raises the question whether a correlation exists between the genes encoding KIR and HLA. The ligand specificity for activating KIRs is not well defined. The ligands of some activating KIRs have not been identified yet. The activating receptors of KIR2DS2 and KIR2DS1 were reported to have a lower affinity of binding to HLA-C than those of their closely related inhibitory receptors. It is also possible that non-HLA ligands exist for these activating KIRs. The KIRs with a defined cognate ligand are presented in table 3.

The KIR surface protein repertoire in an individual is mainly determined by the KIR genes. Hence, a lack of expression is more likely caused by the lack of that gene than by a down-regulation. KIR genes are expressed by NK cells in a clonal manner, each individual NK cell within a person possesses a different combination of KIRs, with a subset of the total KIR gene repertoire being expressed on each individual. KIR2DL4 is one notable exception; this gene is ubiquitously expressed on NK cells. The frequency of each expressed KIR may differ between individuals, but is stable over time. For example the gene KIR2DL1 may be expressed on 50% of the NK cell population of individual A, while in individual B the expression of KIR2DL1 is found to be 14% of its NK cell population. One explanation for this difference could be that particular alleles of a gene are expressed more frequently due to the presence of multiple copies of a gene.

This Example presents a new method for KIR genotyping with multiplex ligation dependent probe amplification (MLPA). With this method a rapid and convenient way of KIR genotyping is performed and also the relative number of copies of the KIR genes is quantified. Copy number variation (CNV) accounts for a substantial amount of genetic variation, resulting in significant phenotypic variations in e.g. transcript levels and therefore are of functional relevance.

We developed two synthetic MLPA probe sets for the typing of 16 out of the 17 KIR genes KIR2DL1-5, KIR2DS1-5, KIR3DL1-3, KIR3DS1, KIR3DP1 and KIR2DP1. The probes for the KIR genes were designed for different loci to detect most of the alleles. Probesets 1 and 2 are listed in FIGS. 3A and 3B. The specificity of the probes was validated by comparison of the samples for the KIR genotypes obtained with PCR-SSOP and PCR-SSP methods, and the ability of the probes to quantify relative gene copy numbers was examined with 12 families, each consisting of two parents and two offspring, which have been genotyped for most KIR alleles.

Materials & Methods

DNA Selection/Isolation

DNA from unrelated randomly selected Caucasian donors was obtained for this study to test the peak profile of the probes. For the validation of the probes five SSP-PCR KIR typed genomic DNA samples and 11 EBV transformed B cell lines from the 10th International Histocompatibility Workshop were used (Cook et al, 2003), JVM, T7507, OLGA, SAVC, JBUSH, BM16, LBUF, AMALA, BM90, TAB089 and KAS116. The KIR Reference Panel I from the IHWG containing 48 samples from 12 Centre de'Etude du Polymorphism Humain (CEPH) families □ including 2 parents and 2 children (table 4: KIR typing of the 48 samples and FIG. 7: the pedigrees) □ also served this purpose, but its main purpose was to determine the ability of copy number quantification of the probes. Genomic DNA and the DNA from the Cell lines were isolated with Qiagen (blood kit) according to the manufacturer's instructions.

Probe Design

Probes were designed according to general instructions. All the probes were manufactured by Invitrogen (Carsblad, Calif.). The sizes of the probes after ligation ("ligated probes") are spaced four to five nucleotides apart, to separate each amplification product on the sequence type gels, amplification product size ranged from 95 to 223 nucleotides. All MLPA probes contain a PCR primer sequence, which is recognized by a universal primer pair. PCR primer sequences were: forward 5'-GGGTTCCCTAAGGGTTGG-3' (SEQ ID No: 3) and reverse 5'-TCTAGATTGGATCTTGCTGGCAC-3' (SEQ ID No: 2).

The KIR probes were designed to identify and discriminate between the 17 KIR genes listed in table 1, with exception of KIR2DL5B. No specific probe could be designed for this gene. The probe for KIR2DL5 now, detects both KIR2DL5A and KIR2DL5B genes. In addition probes on alternative sequences and intron sequences were designed, using basic local alignment sequence tool searches and the IPD/KIR Database. The sizes of the KIR probes can be found in tables 5 and 6.

The targets of the nine control probes are on conserved genes in the human genome, FGF3, BCAS4, LMNA, PARK2, MSH6, GALT, SPG4, IL-4 and NF2. These target genes were tested to show no considerable variation between donors in a previous MLPA study at Sanquin. Control 1 and 10 were initially 88 by and 130 by respectively, but have been elongated to 180 bp and 223 bp to distribute the control probes more evenly among the KIR probes. Table 7 shows the list of the genes and the sizes of the control probes.

Competitor probes are designed where the signal of the probe was off-scale to be detected by the capillary electrophoresis apparatus and are listed in table 8.

MLPA Reaction

All DNA samples were diluted to 20 ng/μl with water and 5 μl was denatured at 98° C. for 5 minutes in 200 μl tubes in a Biometra T-1 Thermoblock with heated lid.

MLPA reagents (EK kit 5) were obtained from KIRC-Holland (Amsterdam, The Netherlands). SALSA MLPA buffer (2 μl) and 1-10 fmol of each MLPA probe in a probe mixture (1 μl) were added and incubated for 1 minute 95° C., followed by 16 hours at 60° C. in a total volume of 10 μl. Ligation of the hybridized probes was performed by reducing the temperature to 54° C., before adding 32 μl Ligase-65 mix (3 μl ligase buffer A, ligase buffer B, 1 μl Ligase-65 and 25 μl water) and incubated for 15 min. After inactivating the enzyme at 98° C. for 5 min, 10 μl of the ligase mix was diluted with 4 μl PCR Buffer and 26 μl water at 4° C. in 200 μl tubes. For the PCR reaction, 10 μl of polymerase mix (0.5 μl polymerase, 2 μl SALSA enzyme dilution buffer, 2 μl SALSA PCR-primers and 5.5 μl water) was added at 60° C. PCR amplification of the ligated MLPA probes was performed for 36 cycles (30 sec 95° C., 30 sec 60° C., 60 sec 72° C.) followed by an incubation for 20 min at 72° C.

Electrophoresis

1 μl PCR product is added in new tubes containing 0.4 μl Promega Rox size standard 60-400 bp+8.6 μl High Definition buffer. The products are separated by Applied Biostystems Genetic Analyzer 3130XL capillary electrophoresis according to its molecular weight and the resulting electropherogram show specific peaks that correspond to each probe.

Analysis

Data were visualized with Genemapper v3.6 and normalized with Soft genetics Genemarker v1.6, using internal control probe normalization. Finally these data was exported to an Excel file.

Results

Detection of Probe Signal

All the MLPA probes were initially tested on randomly chosen donors. We first examined if the probes would generate a signal and if these signals corresponded with the expected size of each probe. The control probe peaks and the probe peaks for the four framework genes, KIR2DL4, KIR2DL3, KIR3DL3 and KIR3DP1, occurred in all samples, as expected. KIR gene content variation between individuals was observed when different samples were compared, FIG. 8. The probe intensity is denoted by arbitrary units (AU) on the y-axis and the probe size is expressed on the x-axis in basepairs (bp). We used the peak height to quantify the data, while others may suggest probe area.

Secondly, the intensity of the probe signal was examined. The peak patterns were visualized with Genemapper, to observe the peak intensities before normalization. Genemarker is used to normalize the data and correct this for the decay of larger probes, but does not indicate where signals are off-scale. It is preferred to have a probe signal between 500-6000 AU in order to obtain a more reliable DQ value. Moreover fluorescent peaks with a signal less than 500 AU may not always be detected when more probes are added to the reaction. Fluorescent peaks above 6000 AU can be off-scale to be detected by the sequencer and decrease the signal of other probes relatively. Several suggestions are described to enhance or lower probe intensity, the nucleotide composition next to the PCR primer tag sites and/or the GC content of a probe are a few factors that can be of influence. In general competitors are used for reduction of probe signals and a higher probe concentration for an increase in signal. Competitors are oligonucleotides that are identical to a part of the MLPA probe without the forward or reverse primer sequence, depending whether the left or right part is chosen.

Competitors compete with the MLPA probe for the same target, however no amplification of these ligated probes will occur, since they lack a primer sequence. The result is that less probe amplification product will be detected and lower peak intensity is obtained.

Competitors were designed for control probes 2, 3, 4, 7 and 9 and in the first place also for the KIR probes 2DL4, 3DL3 (probe set 1) and 3DL2 (probe set 2) These probes had a length of 96 bp, 100 bp and 108 bp, respectively. However we observed a decrease in peak intensity, more or less corresponding with an increase in probe size. Longer synthetic probes are more likely to contain a higher proportion of incomplete oligonucleotides. Therefore it seemed to be an option to elongate the length of probes with high peak intensities and to shorten this for probes with low peak intensities. Probe 2DL4 was redesigned to 170 bp and 3DL3 to 154 bp and lower peak intensities were the result. The peak generated by probe 3DL3 (100 bp) was not affected by its competitor and was apparently a product of the probe 2DS3 (108 bp), because when this probe was removed from the probe set 1, the off-scale signal reduced to normal. Furthermore competitors with a length of 30 bp had less effect than those with a length of 50 bp, in which case a higher dosage was needed to reduce the probe signal (data not shown).

For probes that failed to generate a signal or for which the signal was insufficient, the followings have been performed; a three- to ten-fold concentration of these probes was used and probes that have a high overlap in sequence were not included in one probe set. Placing two cytosine nucleotides after the forward primer should increase the probes signal and a tyrosine base should decrease this, reported in the MLPA design protocol. However in our experiment, several probes were redesigned to contain two cytosines after the forward primer and this did not produce the same results. Probes that still failed to generate a signal after the aforementioned proceedings and testing on lager number of donors were replaced by probes on the reverse strand of the target gene or by probes that have a different target location on that gene.

The frequencies of each KIR gene probe peak on the tested samples were compared with the KIR gene frequencies in Caucasian population (table 9). Probes with observed frequencies that were contradicted by the population frequencies were assumed to give false negative or false positive results and were replaced by new designs. These were assumed to be caused by gene variation at the ligation sites of the probe.

The list of the alleles that can be detected by the KIR probes and the coverage of the total KIR alleles by the probes are shown in table 10.

Other Factors Interfering with Peak Intensities
Probe Quality

We experienced differences probe quality by probes that were manufactured at different companies. The nine control probes were initially ordered from Biolegio which had also supplied these for the C4 MLPA project previously done here. All the KIR MLPA probes were ordered at Invitrogen. The control probe set was separated in two mixes, control probes 1 (IL-4), 2 (FGF3), 3 (BCAS4), 4 (LMNA), 5 (PARK2) and 7 (MSH6) in one and the control probes 8 (GALT), 9 (SPG4) and Ctrl 10 (NF2) in the other. The concentration needed for each control probe varied and ranged from 0.5 fmol to 6 fmol and also different concentrations of competitors were needed.

The control probes used for the KIR MLPA were ordered from Invitrogen. Only 1 fmol is needed for each control, with the exception of control probe 5 (3 fmol) in order to obtain the same peak intensity as mention above and the probes do not need to be separated into two mixes. Due to the better probe quality, time is saved in producing the probe sets.

Template DNA Amount

A MLPA reaction with 50 ng of DNA was performed and compared with 100 ng that is used throughout this study. MLPA reactions using a DNA amount of 20 ng have been reported by Schouten et al. (Schouten et al, 2002). When the peak profiles were compared, no striking differences between these two reactions were observed. The DQ of the nine control probes were calculated for each sample and a sample with 100 ng DNA was taken as reference. Seven out of eight samples containing 50 ng of DNA showed a DQ value outside [0.8-1.2] for more than three control probes, ranging from [0.3-1.5] within one sample. While all the eight samples of 100 ng DNA had DQ within the acceptable range [0.8-1.2] for all the nine control probes, with exception of one sample that had two control probe DQ value outside this range. Here we conclude that MLPA reactions with different amounts of DNA cannot be compared with each other, because the DQ values of the same sample did not yield the same score with the different DNA amounts.

Next the samples of 50 ng of DNA were compared among, by taking a sample of 50 ng DNA as reference. The observation was that three of the eight samples had more than three control probes with a DQ value out of the range of [0.8-1.2]. When the nine control DQ values of one sample were analyzed, values between [0.5-1.7] were found. Therefore MLPA reactions carried out with 50 ng of DNA were considered to be unreliable, as the DQ values of the probes showed a great variation between the samples and within one sample, which was not observed with the samples that contained 100 ng of DNA. The requirement of higher amounts of DNA for this study could be explained by the fact that we are using a completely synthetic probe set in contrast with the probe sets used by Schouten et al (Schouten et al, 2002). Moreover most studies that were carried out with little amount of DNA often only analyzed chromosomal abnormalities, such as recombination or mutations and did not quantify copy numbers.

Reproducibility

Samples of different runs were not always comparable, when the DQ of the control probes were calculated. The explanation is that the experimental conditions may vary with each run, due to human acting or differences in probe signal reproducibility. Therefore, samples within the same run are preferably normalized and analyzed first before comparing the data with samples of a different run. Reference samples with a more or less established relative gene copy numbers, are preferably included in each experiment to act as reference.

Validation with KIR Typed DNA Samples

The specificity of the KIR probes was verified by testing 11 EBV-transformed cell lines, which were KIR-genotyped by the 10th International Histocompatiblity Workshop (IHW) (Cook et al, 2003). The cell lines were KIR-genotyped using PCR-SPP and PCR-SSOP and were carried out in three separated laboratories. The cell lines were not genotyped for the genes KIR2DL5A, KIR3DL3, KIR2DP1 and KIR3DP1 and also contained no negative controls for the genes KIR2DL1, KIR2DL4, KIR3DL1, KIR3DL2 and KIR2DS4.

In addition, DNA samples from 5 individuals were genotyped by PCR-SSP for further verification. These 5 samples were also genotyped for the genes KIR3DL3 and KIR3DP1 and found to contain true negative genotypic results for KIR2DL1 and KIR2DP1. The results of the verification of the two probe sets are shown in tables 11-14.

Probe Set 1

KIR genotyping with probe set 1 was found to be consistent with the 10$^{th}$ IHW on 10 of the cell lines for the probes 2DL1-5, 2DS1, 2DS3-5, 3DL1-2 and 3DS1.

All cell lines were typed positive for the genes KIR2DP1, KIR3DP1 and KIR3DL3, the first has a frequency between 94-100% (table 9) and the last two are framework genes that are always present. Typing of the 5 individuals yielded the same results as with the PCR-SSP, except for the probe 2DS2.

Probes for 2DL5A (Same Probe in Probe Set 2)

Most studies on KIR genotyping detect the presence of KIR2DL5 and do not differentiate this gene between the two genes KIR2DL5A and KIR2DL5B. These two genes show a nucleotide sequence difference of only 1%. We were unable to design a probe for KIR2DL5B, because a specific ligation site to discriminate KIR2DL5B from KIR2DL5A and the other KIR genes was not found. The probes that were designed for KIR2DL5A also detect the allele KIR3DP1*004 (table 10), because this allele contains no other difference in the sequence within the probe's range, thus the probe sets do not contain specific probes for the selective detection of KIR2DL5A. In fact, KIR3DP1*004 is non-expressed, and forms a hybrid of the promoter of KIR2DL5A and the coding region of KIR3DP1. When probe 2DL5A generates a signal in the MLPA, this could indicate the presence of both KIR2DL5A and KIR3DP1*004 or either 2KIRDL5A or KIR3DP1*004 alone. However, probe 2DL5 detects the same KIR2DL5A alleles as probe 2DL5A. When probe 2DL5 is not binding and probe 2DL5A is, the absence of KIR2DL5A and the presence of KIR3DP1*004 is demonstrated. This is clearly demonstrated by the cell lines JVM, SAVC, JBUSH, BM16, TAB089, KAS116 and the individuals 33_8025 and 33_8588 (FIG. 10).

Probe Set 2

Probe set 2 contains a smaller proportion of probes. A higher proportion of the probes had overlapping sequences and seven out of the ten KIR probes needed a 10-fold higher concentration than the others to obtain peak intensities above 500 AU.

Probe 2DS5 and 3DS1

Probes 2DS5 and 3DS1 bound to all samples including to those genotyped negative for KIR2DS5 and KIR3DS1, indicating unspecific ligation of the probes. Probes 2DL5 and 3DS1 were not based on primer sequences used before, the probe search tool on the HIR database and BLAST results showed no match with other HIR genes and these probes were considered to be specific for KIR2DS5 and KIR3DS1. No explanation could be found, why these probes gave false positive results. These probes were excluded from probe set 2.

Probe 2DS1

Three out of the six negative cell lines for KIR2DS1 were typed positive by this probe, while the two negatives from the PCR-SSP-typed individuals were correctly typed. Probe 2DS 1 target is on an intron and only little information about intron sequences is available. The fact that other KIR genes may possess the same sequence at this position, cannot be excluded and therefore this probe is not included in the probe set.

Probe 3DP1

The probe 3DP1 in probe set 2 detects a deletion of exon 2, this allele of KIR3DP1 is designated as KIR3DP1 *003 and has a frequency of 0.72 in the Caucasian population. Sample 33_8588 of the PCR-SSP typed individuals was typed negative for KIR3DP1 by the MLPA probe and positive by PCR-SSP (table 14). The conflicting typing results between these two methods can be explained by the presence of exon 2 in this sample.

Cell Line LBUF

Both probe sets have genotyped this cell line positive for KIR2DL3 and negative for KIR2DL5 and KIR2DS. In addition, probe set 1, typed LBUF negative for KIR2DS1, KIR2DS5 and KIR3DS1 (table 11 and 13). It is reasonable to assume that the cell line LBUF that was tested, was not the same as published before by the 10$^{th}$ IHW. LBUF had been KIR-genotyped by Hsu et al. 2002 (Hsu et al, 2002) and their typing was consistent with ours. Moreover, LBUF and the other cell lines was KIR-genotyped with the standard PCR-SSP method and these results confirmed our findings with MLPA, including the positive typing results of the genes KIR3DL3, KIR2DP1 and KIR3DP1 on all 11 cell lines.

Quantification of Gene Copy Numbers

For the verification of gene copy number quantification, samples with a well-defined number of copies of KIR genes were needed. Since these are not available, we used the KIR reference panel I for this purpose, comprising 12 families of two parents and two children each. These 48 reference samples have been KIR-genotyped by 15 different laboratory groups utilizing PCR-SSP and PCR-SSOP. The Centre de'Etude du Polymorphism Humain (CEPH), Foundation Jean Dausset, Paris, France, had prepared lymphoblastoid cell lines (LCLs) of these families. The International Histocompatibility Working Group (IHWG) Cell and DNA Bank has made this panel available for commercial use.

All the samples have been identified for the presence or absence of 16 of the KIR genes and for two variants of KIR3DP1, (KIR3DP1*003 and KIR3DP1v) and two variants of KIR2DS4 (KIR1D alias KIR2DS4*003 and KIR2DS4) (table 4). Whereas, KIR3DP1 of the KIR reference panel I is characterized by the absence of exon 2 and the KIR3DP1v indicates the remaining KIR3DP1 alleles. KIR1D contains a 22-bp deletion in Ig-like domain D2, causing a frame shift and early stop codon which lead to a truncated protein product (Hsu et al, 2002).

The haplotypes of these six families were also available as shown in FIG. 7. In addition this figure shows the pedigrees of the 12 families. Because of the information about the haplotypes, we could assume that some samples exhibit at least two copies of KIR genes. The inheritance patterns of these copy numbers was deduced from the pedigree information. The reference panel has at the same time been utilized as an extra verification step for the specificity of the probes.

Specificity in KIR Genotyping

With both probe sets difficulties were experienced with generating reliable data of the MLPA experiments with the KIR reference panel, presumably this is caused by the lower quality of the DNA samples, as this did not occur with the genomic DNA samples of the previous experiments. The DQ values of the control probes had a higher frequency outside the proposed normal range [0.8-1.2]. Therefore, data of a number of samples is missing and these samples should be tested in the future.

Probe Set 1

16 probes: 2DL1-5A, 2DS1, and 2DS3-5, 3DL1-3, 3DS1, 2DP1 and 3DP1 were tested and the majority of the probes genotyped the KIR reference panel accordingly to what has been reported, except there were some differences with probes 2DP1 and 2DL5. These samples were correctly typed by probe set 2.

Probe Set 2

The probes: 2DL1-5A, 2DS2, 2DS4, 3DL1-3, 3DS1, 2DP1 and 3DP1, in total 14 probes were tested on the reference panel. Probe 3DP1 was designed for KIR3P1*003 (denoted as 3DP1 in table 4) and its specificity for this allele was confirmed with the reference panel. Probe 2DL2 typed approximately 58% false positive and probe 2DL1 typed three of the four negative of the panel to be positive and, therefore, no further testing has been done with these two probes. Probe 2DS2 typed around 15% incorrectly as negative, although in a previous run which was rejected because of the DQ values of the controls, these two samples were typed positive. These samples need to be revised before a conclusion about probe 2DS2 can be drawn. Probe 2DS4 gave one false negative result (sample 1333-8281). Only 80% of the KIR2DS4 alleles can be detected by this probe because of a gene variant that is 4 bases away from the ligation site in 1 out of 9 alleles. The right part of this probe will be redesigned with an UIB code on this position.

Quantification of CNV

Probes that have been demonstrated to be accurate in KIR genotyping in both probe sets have been analyzed for their ability in copy number quantification. Relative quantification of CNV with one probe is simply not reliable because gene variations near the ligation site of the probe may influence the outcome in DQ value. This is especially true for KIR sequences, because they show a high level of gene variation, while demonstrating a homology up to 99%. Certain probes discriminate the different KIR genes only by one nucleotide difference at their ligation site. A gene variant near the ligation site of the target gene may lead to a lower probe signal. Alternatively, a gene variant at one of the other KIR genes might cause a probe to recognize this gene as its target, thus enhancing the probe signal. Therefore only the KIR genes of the families with the reported haplotype and the complete MLPA data of the two probes are analyzed for copy numbers.

The DQ values of the control probes of both probe sets on each sample were compared to check if the MLPA data are reliable. The nine control probes should generate the same DQ values as these control probes are the same in both probe sets and are tested on the same sample. Samples with less than seven comparable control probe DQ values between the two probe sets were excluded. Next, the DQ values of the KIR probes were evaluated. We interpreted the following; DQ values of 0.3< as 0 copies of that gene, DQ [0.4-0.7]=1 copy, DQ [0.8-1.2]=2 copies, DQ [1.3-1.7]=3 copies, DQ [1.8-2.2] =4 copies, DQ [2.3-2.7]=5 copies, etc. The borderline values, such as a DQ of 0.7 are questionable and when the second probe obviously quantified 1 copy of this gene, 0.7 was considered as 1 copy, the same approach is applied with other borderline values.

Figure 11A:
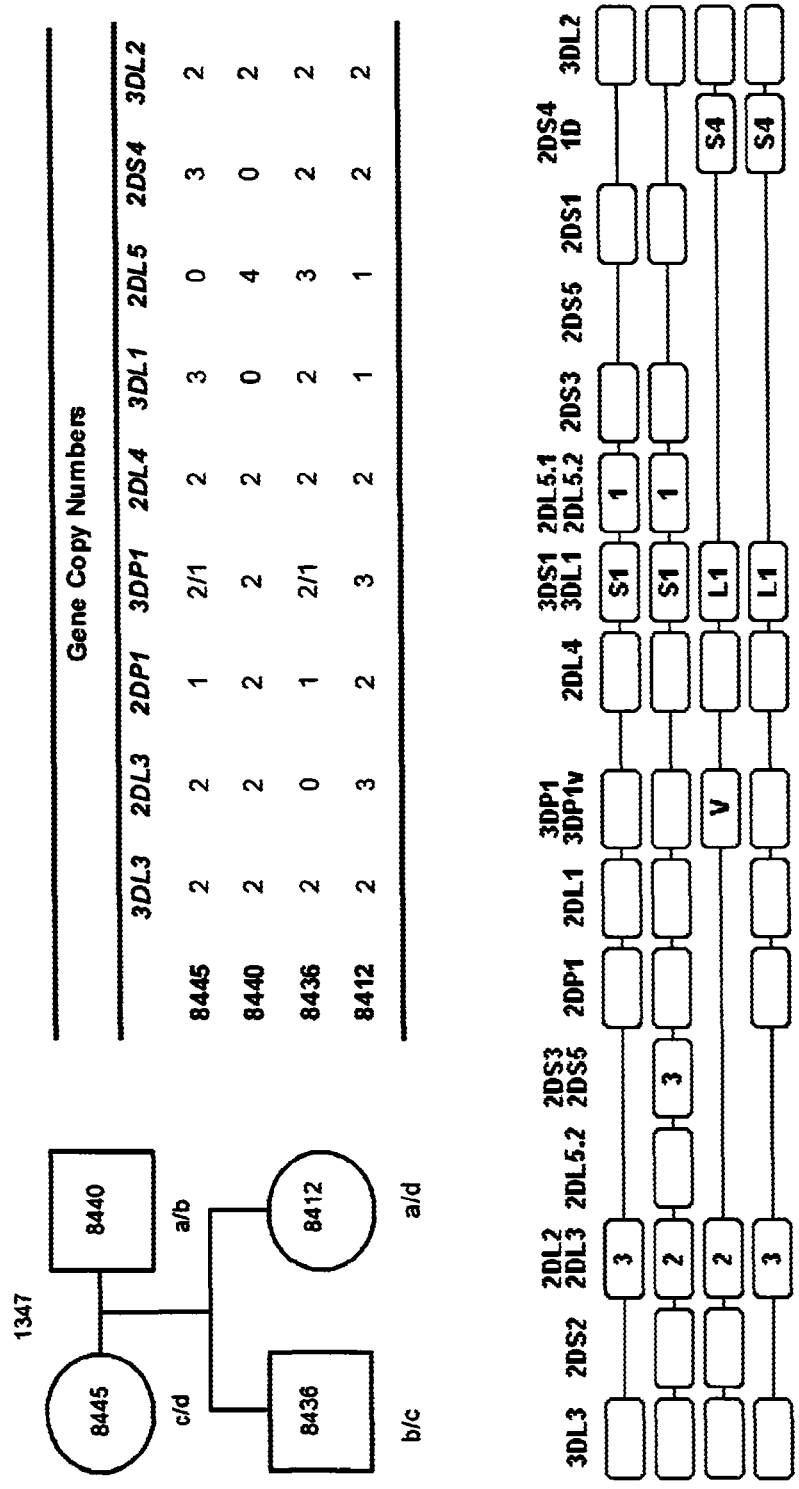
Figure 12A:
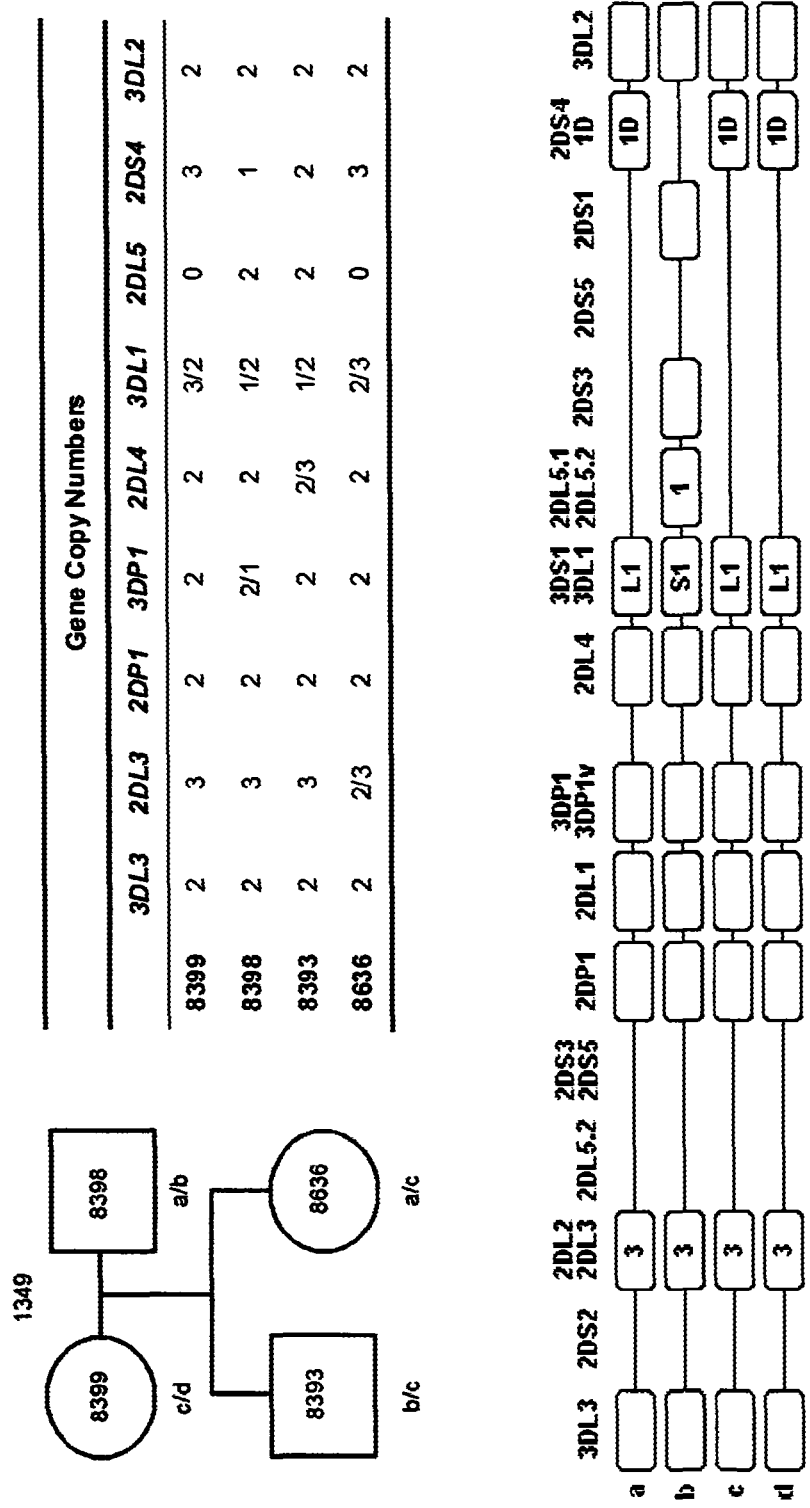

FIGS. 11A and 12A show the pedigrees of the families 1347 and 1349, respectively and the legends for the haplotype are displayed below. The copy numbers of the KIR genes are listed in the FIGS. 11A and 12A next to the pedigrees.

A difference in the quantification of the exact copy numbers was observed with the probes for KIR3DP1 in samples: 1347-8445, 1347-8436 and 1349-8398.

Probe set 1 seems to detect more copies of this gene than probe set 2, which is in agreement with their design. Probe 3DP1 (1) detects all the KIR3DP1(v) alleles and probe 3DP1 (2) detects only KIR3DP1*003 denoted in the legend as 3DP1, which exhibit the exon 2 deletion. The probes 2DL3 and 2DL4 in probe set 1 detected fewer copies numbers than their counterparts in probe set 2. Probe 2DL3 and probe 2DL4 might have problems with the presence of gene variants at their target sequence, whereas these probes in probe set 2 have no gene variants in the probe target sequence and give a coverage of 100% (table 10). The probes for KIR3DL1 quantified the members of family 1349 differently. The probe in probe set 1 covers different alleles than the probe in probe set 2, the coverage rate are 78% and 41% respectively due to gene variants present at their target sequence more then 10 bases away from the ligation site, that might influence the binding efficiency and thereby the peakhights. Also here adding IUB codes in the probe sequence will overcome the problem of misinterpretation of copy number differences between individuals.

Despite the differences in copy number quantification of a number of probes, the overall inheritance pattern of the gene copies was in agreement with the inheritance of the haplotypes. For example the four framework genes KIR3DL3, KIR3DP1, KIR2DL4 and KIR3DL2 were present in all samples and at least 2 copies of each of these genes have been found. This indicates that these genes are present in at least one copy at each allele and are inherited from both parents. Examination of family 1347 revealed that the father, haplotype a/b (sample 8440) has three copies of gene KIR2DL5 on one allele, haplotype b and one on the other, haplotype a and has past haplotype b, with the three copies to the child (sample 8436) and the allele haplotype a, with one copy to the other child (sample 8412). For the family 1349, one copy of KIR2DS4 is believed to reside on one allele, haplotype c and two on the other, haplotype d of the mother (sample 8399). Because both children, haplotype b/c and haplotype a/c (sample 8393 and 8636), respectively, inherited the allele with two copies from their mother as they have both the haplotype c and one child (sample 8636) inherited one copy of this gene from its father, haplotype a. Also when the inheritance patterns of the remaining copy numbers of genes were analyzed, no inconsistency with the inheritance patterns of the haplotypes could be found. The rest of the families with fully reported haplotypes should be tested again to obtain complete data of all the members within one family, before the inheritance patterns and copy numbers can be analyzed.

Discussion

Before the present invention, the main problem in designing synthetic MLPA probes for KIR genotyping was to design probes specific enough for the target gene, but still sensitive enough to detect most of the alleles present in the population. KIR genes have very high level of homology (85-99%) in the sequences of both exons and introns and show an extensive degree of gene variation.

The MLPA is a good method, because it can discriminate target sequences that only differ one nucleotide at the ligation site. The present inventors designed synthetic MLPA probes consisting of three probe parts which added a second ligation site, so that an extra discrimination point was provided. In addition these three-part probes made it possible to elongate the ligated probe size, the longest probe tested in this study was 223 bp (Ctr 10). Due to the better quality of the probes and three-part probes, the number of probes in a synthetic MLPA probe set according to the invention is less restricted by the size of the ligated probes.

This study has demonstrated that the MLPA with two synthetic probe sets is reliable in KIR genotyping, as these two probe sets have been well validated by three independent approaches. The two probes sets complement each other in the detection and coverage of the KIR alleles, which yielded in no false negatives any more in all the samples used for verification. Even after exclusion of the probes that may have generated false positives from the probe sets, all 16 KIR genes can still be consistently detected for their presence or absence. This makes the MLPA methods used in this Example in a qualitative sense comparable to the PCR-SSP and PCR-SSOP methods. However time and work is saved with the performed Example, as only two reactions are needed to generate a complete KIR-genotype profile.

In summary, probe set 1 contains the probes 2DL1-5, 2DS1, and 2DS3-5, 3DL1-3, 3DS1, 2DP1 and 3DP1, in total 15 probes. Probe set 2 contains the probes 2DL3-5, 2DS2-4, 3DL1-3, 2DP1 and 3DP1, in total 11 probes. Together these two probe sets are accurate for the typing of 16 KIR genes and for quantifying relative copy numbers of at least 9 KIR genes.

Example 2

This Example presents additional probes for KIR genotyping and copy number variation analysis with multiplex ligation dependent probe amplification (MLPA). Here, probes are presented for all 17 KIR genes KIR2DL1-5, KIR2DS1-5, KIR3DL1-3, KIR3DS1, KIR3DP1 and KIR2DP1, including KIR2DL5a and KIR2DL5b, KIR3DP1v and several null alleles. The extended probesets 1 and 2 are listed in FIGS. 3C and 3D, respectively. As in example 1, the specificity of the probes was validated by comparison of the samples for the KIR genotypes obtained with PCR-SSOP and PCR-SSP methods, and the ability of the probes to quantify relative gene copy numbers was examined with 12 families, each consisting of two parents and two offspring, which have been genotyped for most KIR alleles.

Materials & Methods

For DNA selection/isolation, probe design, MLPA reaction, electrophoresis and analysis according to materials & methods of example 1 with the exception that no competitors were used and data were normalized with Soft genetics Genemarker v1.85, using internal control probe normalization and synthetic references.

Results

Extended Probesets

With the extended probesets 1 and 2 all KIR genes and several KIR gene variants were detected.

Figure 3C:
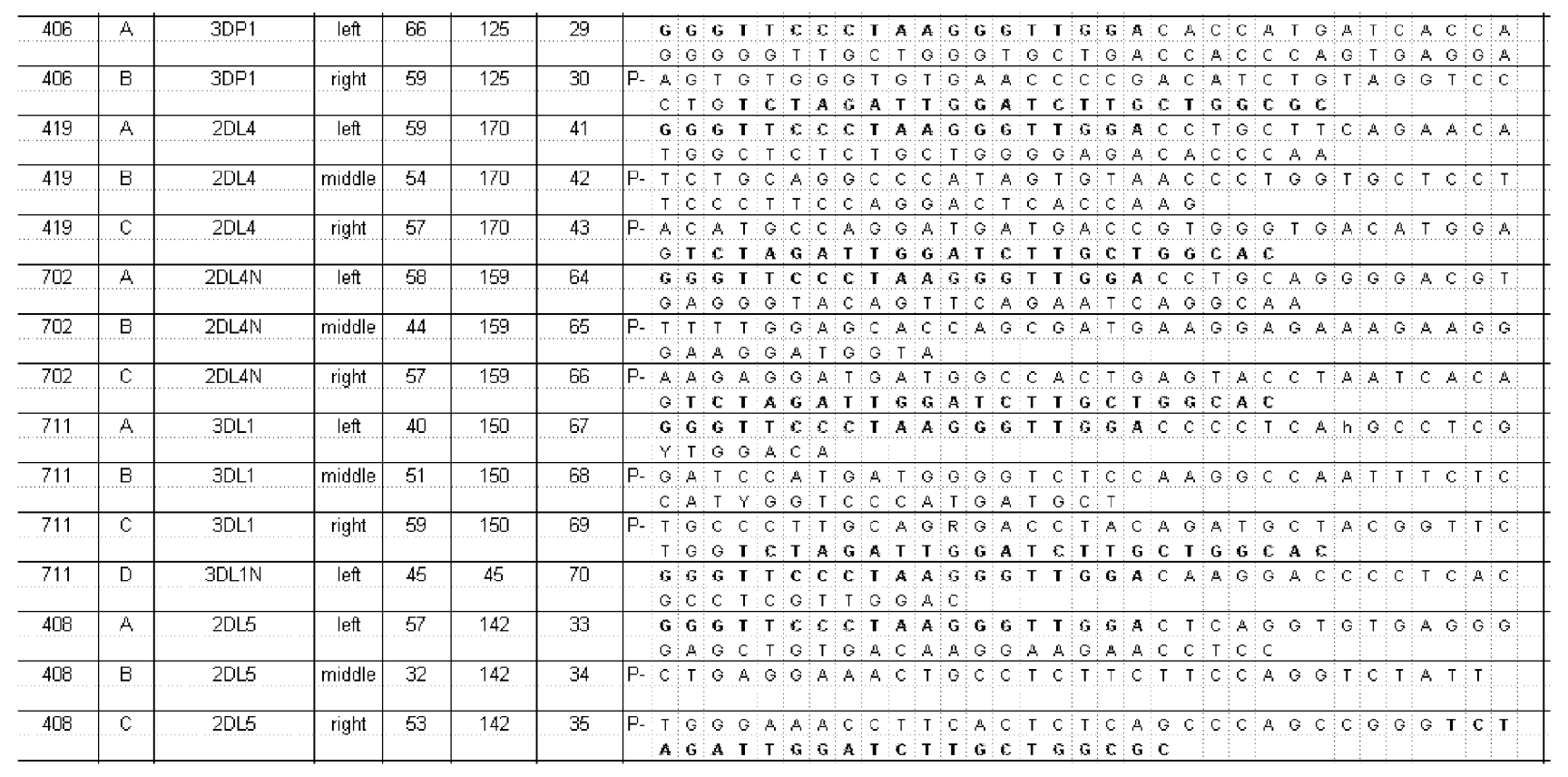
Figure 3C:
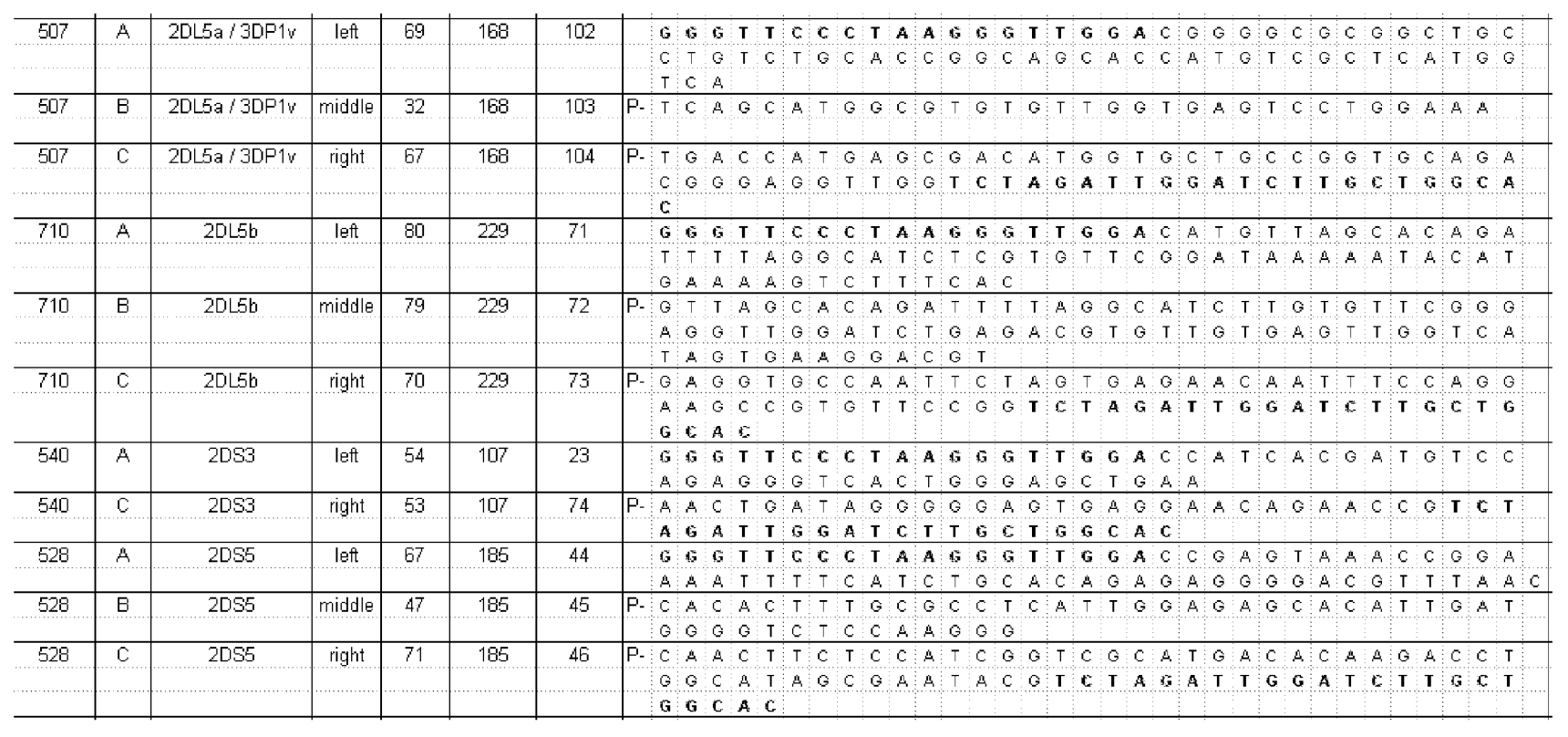
Figure 3C:
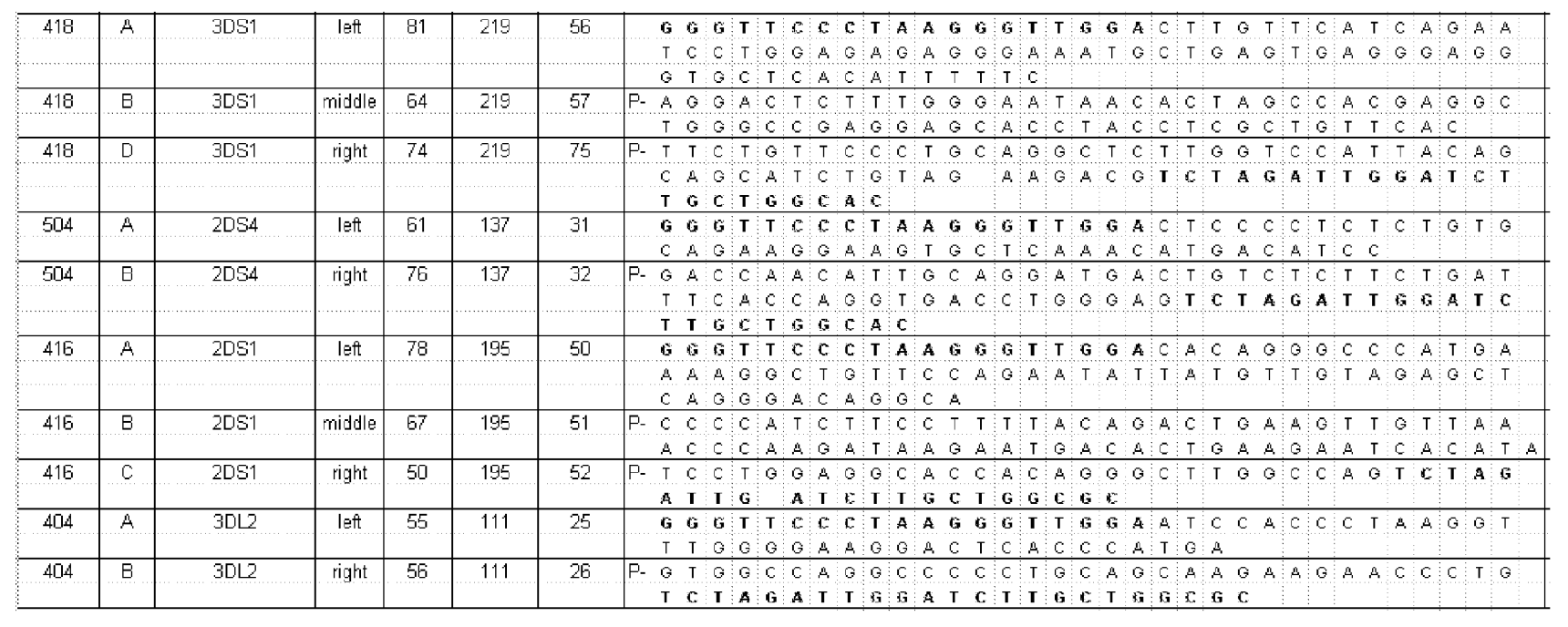

The extended probe set 1 depicted in FIG. 3C detects the same genes as probe set 1 of example 1 but additional probes are added and therefore additional KIR gene variants are now detected. Additional probes that are added are 2DL5B, 2DL4N (2DL4*007,008,009,011), 3DL1*024N.

Figure 3D:
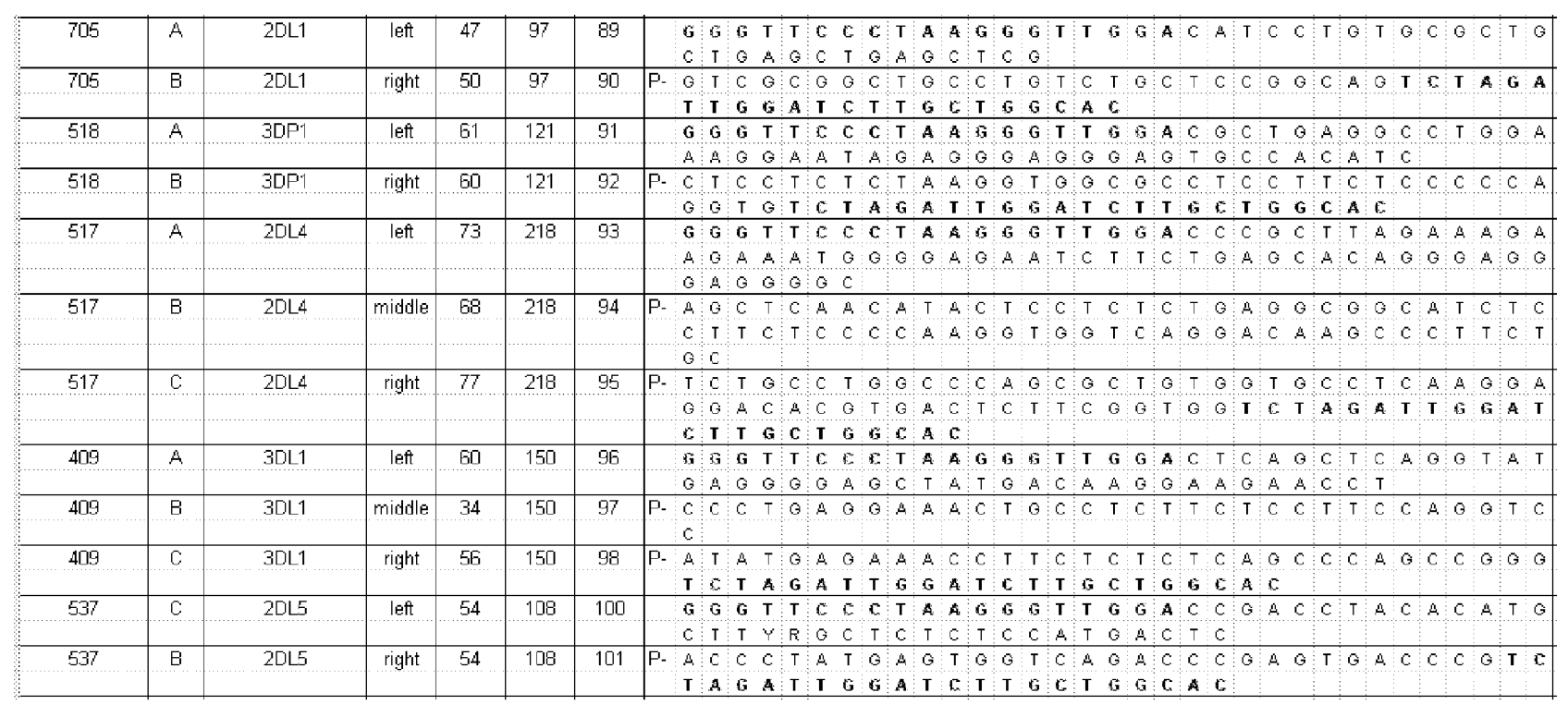
Figure 3D:
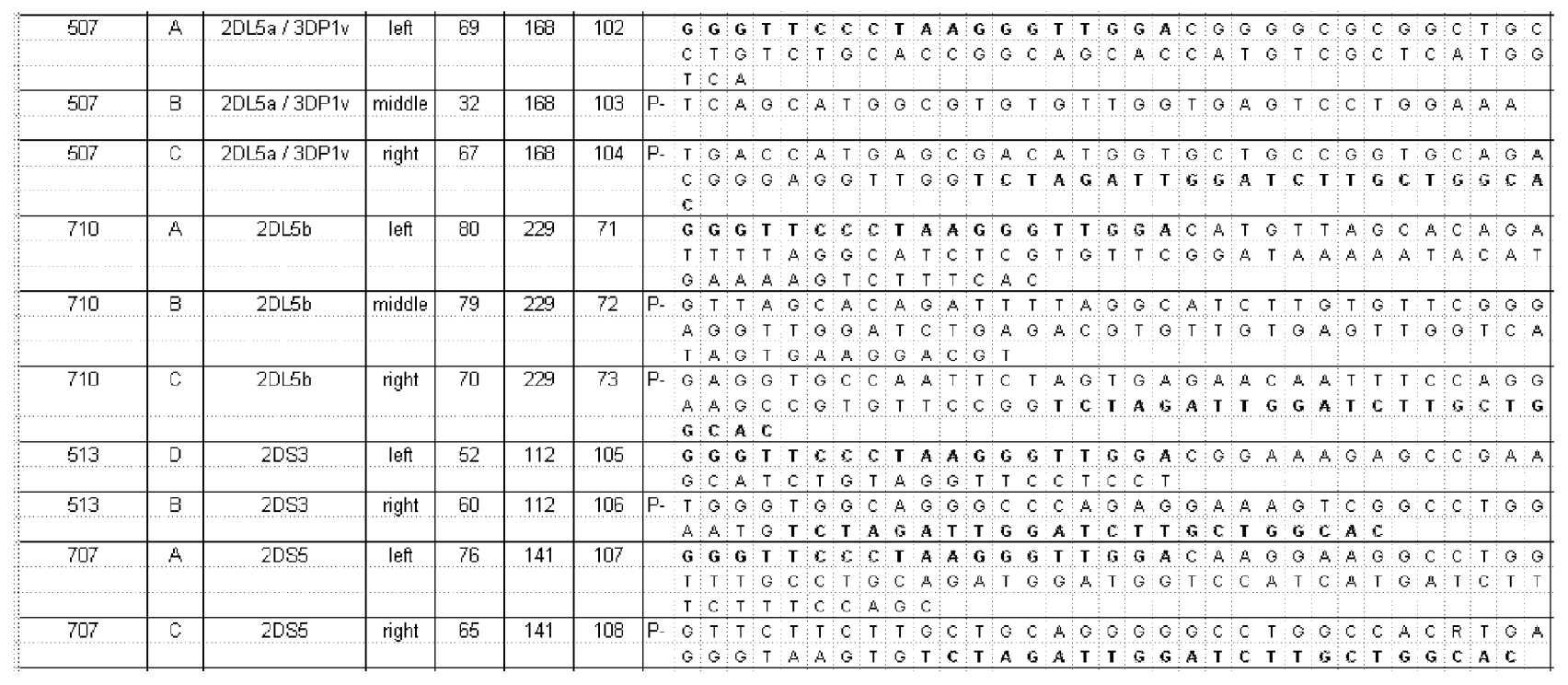
Figure 3D:
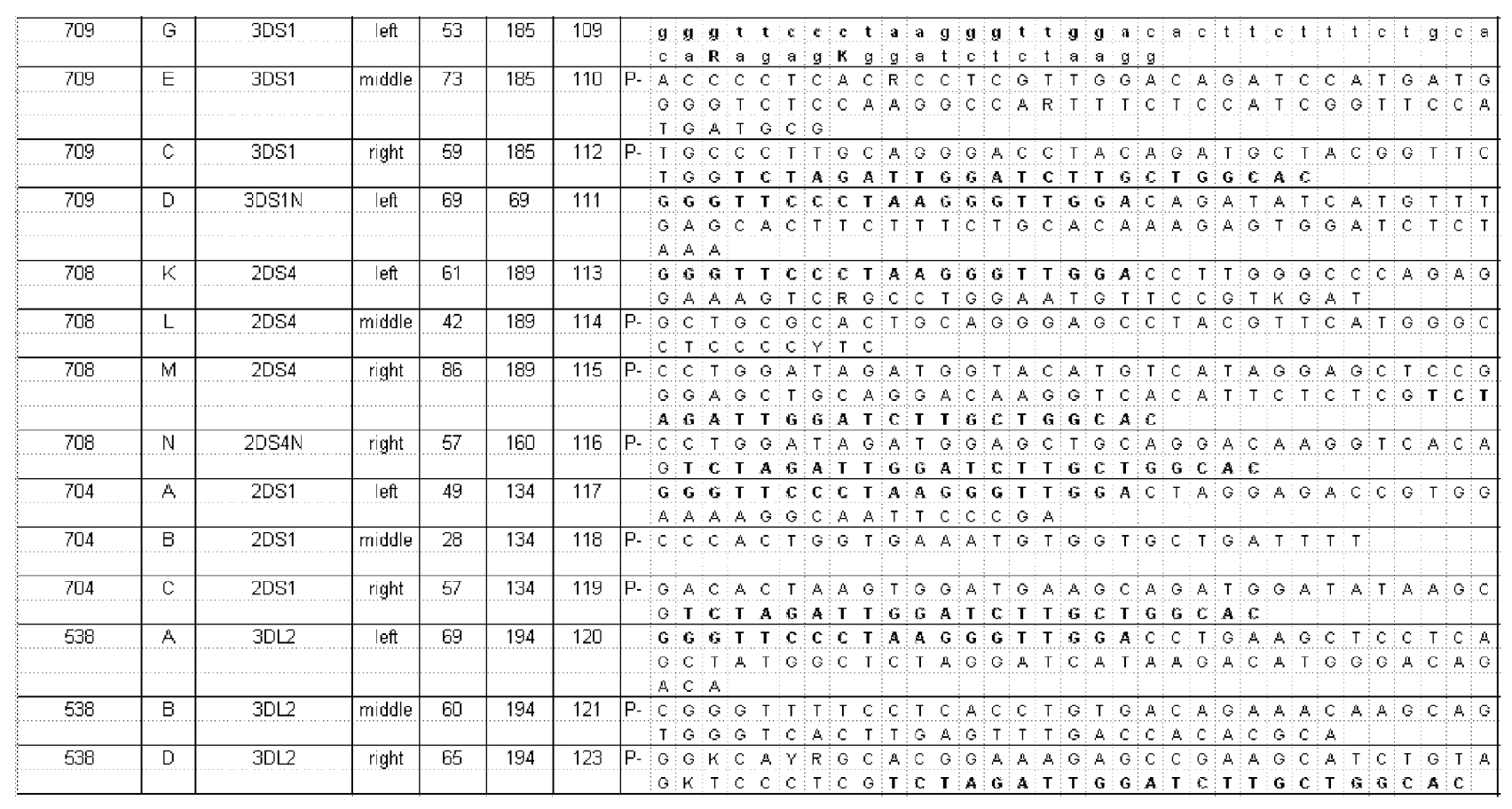

The extended probe set 2 as depicted in FIG. 3D detects the same genes as probe set 2 of example 1 but additional probes are added and therefore additional KIR gene variants are now detected. Additional probes that are added are 2DL5B, 3DS1*049N and 2DS4N (2DS4*004, *006, *007,*008 and *009). KIR2DS4N is also called KIR1D.

Probe 3DP1

The probe 3DP1 in extended probe set 2 detects a deletion of exon 2, this allele of KIR3DP1 is designated as KIR3DP1*003, KIR3DP1*005 or KIR3DP1*006.

Probes for 2DL5A and 2DL5B

With the extended probesets 1 and 2 KIR2DL5A and 2DL5B are now also detected. The probes that were designed for KIR2DL5A and KIR2DL5B also detect the alleles KIR3DP1 variants (table 10, KIR3DP1v). When probe 2DL5A or 2DL5B generates a signal in the MLPA, this could indicate the presence of both KIR2DL5A and KIR3DP1v or KIR2DL5B and KIR3DP1v respectively. Alternatively, when probe 2DL5A or 2DL5B generate a signal in the MLPA the presence of either KIRDL5A or KIR3DP1v alone (with probe 2DL5A) or KIR2DL5B or KIR3DP1v alone (with probe 2DL5B) is indicated. Thus with these probes 2DL5A and 2DL5B more than one KIR gene is detected. Therefore, these probes are not suitable to determine copy number variation (see FIG. 13).

Copy Number Variation (CNV)

For all KIR alleles except KIR3DP1 variants (KIR3DP1v), KIR2DL5A and 2DL5B copy number variation is determined with extended probesets 1 and 2 (FIG. 13).

Quantification of CNV

A difference in the quantification of the exact copy numbers as compared to example 1 was elaborated by studies with the extended probesets. Optimization of the probe set initially used in FIG. 11A, has now resulted in a 100%-perfect match with the validated KIR data in the in example 1 genotyped pedigrees. None of the MLPA probes gave a false-positive or false-negative signal in the $10^{th}$ ICW families tested as exemplified by the analysis of families 1347 and 1349 (FIGS. 11B & 12B). Thus, both probe set 1 and/or 2 and extended probe sets 1 and/or 2 are suitable for detection of KIR genes and for determination of relative copy number variation, but extended probe sets 1 and/or 2, as depicted in FIGS. 3C and 3D, are preferred.

Specificity and Quantification for KIR Haplotyping

From the MLPA data within pedigrees haplotyping can be inferred. First of all, the framework genes KIR3DL3 and KIR3DP1 for the first block in both haplotypes A and B (FIG. 6) and KIR2DL4 and KIR3DL2 are present in a fixed copy number of 2 genes. However, KIR3DP1 may be present as so-called KIR3DP1v variant (see also FIG. 7, grey boxes represent the framework KIR genes in both haplotypes A and B). In case of haplotype B the presence of KIR genes may vary widely (FIG. 6), making this haplotype an important contribution to the variation within the KIR gene cluster.

In family 1347, we have deduced, using the extended probesets, from the pedigree a correct and complete KIR haplotype analysis (FIG. 11B).

At the single gene level the MLPA results offers insight into the patterns of inheritance. The sibs inherited from their parents different KIR haplotypes, which □ for instance □ resulted in the variation in KIR2DL5 gene content. Thus, both sibs have 2 of these genes, containing 2 KIR2DL5 genes from the father (who carries 4 KIR2DL5 genes in total) and one null-haplotype from the mother. From the present data from the literature or the current MLPA data, it cannot yet be distinguished whether the two KIR2DL5 genes that both sibs have inherited, are the same alleles, or whether the KIR2DL5 are located in the first or second block of the so-called B haplotype (see also FIG. 6).

At the haplotype level, patterns of inheritance are deduced for the remaining non-framework KIR genes in this pedigree, e.g. KIR2DL3, KIR2DS2, KIR2DL2, KIR2DP1, and KIR2DL1 genes in the first block of haplotype B, generally located in between the framework genes KIR3DL3 and KIR3DP1 genes (see also FIG. 6).

In case of the first block of haplotype B, the results are explained by the inheritance of a KIR2DL3-KIR2DP1-KIR2DL1 haplotype from the father and the KIR2DS2-KIR2DL2-KIR2DP1-KIR2DL1 haplotypic block from the mother. In case of the second block of haplotype B, it is clear that the KIR3DS1-KIR2DS3-KIR2DS1 haplotype has been inherited from the father and the KIR3DL1-KIR2DS4 from the mother. Yet, one sib (8436) must have lost a KIR3DL1 gene according to our MLPA analysis. Sib 8436 has the normal 3DL1 present in our MLPA, though sib 8412 has inherited a 3DL1N variant gene in stead of the normal 3DL1 gene. This is just by normal inheritance so not an exception.

SSP-PCR can not discriminate between 3DL1 variants (also not between 3DS1 variant genes nor 2DL4 variant genes).

At the haplotype level, patterns of inheritance are similarly deduced for the pedigree of family 1349 (FIG. 12B). Apart from the framework KIR genes in this pedigree, the non-framework genes form the haplotype B that are inherited "en bloc".

In case of these two sibs, 1349-8393 and -8636, the KIR variation can be well explained by inheriting different KIR haplotypes from both parents.

With respect to the first block of haplotype B, the results are explained by the inheritance of one of his two similar KIR2DL3-KIR2DP1-KIR2DL1 alleles from the father and one from the mother (while this female also carried a smaller KIR2DL3-KIR2DP1 haplotypic block).

In case of the second block of haplotype B, it is clear that the father carries a KIR3DL1-KIR2DS4 combination on one allele and a separate KIR2DS3-KIR2DS4-KIR2DS1 haplo-typic on the other allele that were differently inherited by the two sibs, whereas the mother carries two identical KIR3DL1-KIR2DS4 alleles.

In FIGS. 11 and 12 the standard SSP PCR results are compared with our MLPA data with the extended probe sets 1 & 2 for the pedigrees in the CEPH families 1347 and 1349.

Two KIR haplotype models have been described (see for instance: H. Li, PLoS Genetics, 2008, 4, 11:e1000254; M. Uhrberg, Eur. J. Imm. Highlights, 2005, 35:10-15; M. Carington, The KIR Gene Cluster, 2003; K. Hsu, Imm. Reviews, 2002, 190:40-52). The conventional KIR haplotype model assumes that there are two haplotypes A and B. Both haplotypes A and B contain the framework genes 3DL3, 3DP1, 2DL4, and 3DL2. Then there are the KIR genes 2DP1, 2DL1 and 2DS4 that are common for both haplotypes, but only the haplotype A contains 2DL3, 3DL1 and 2DS4. Haplotype B is more variable and can contain the KIR genes 2DS1, 2DS2, 2DS3, 2DS4, 2DS5, 3DS1, 2DL2 and 2DL5 (apart form the aforementioned framework genes). In more than 96% of the worldwide global population the A haplotype at KIR gene cluster contains the KIR genes 3DL3, 2DL3, 2DP1, 2DL1, 3DP1, 2DL4, 3DL1, 2DS4 and 3DL2.

The novel KIR haplotype model assumes that haplotype A and B are present on the two different chromosomes. Therefore any individual can represent an AA, AB or BB genotype. Based on the genes that are present in the DNA sample of that individual, one can conclude which haplotypes are present and the positive genes from the assay can be divided over both haplotypes according to the rules that certain KIR genes are present only in one of the haplotypes A or B, essentially as was mentioned above.

Figure 1A:
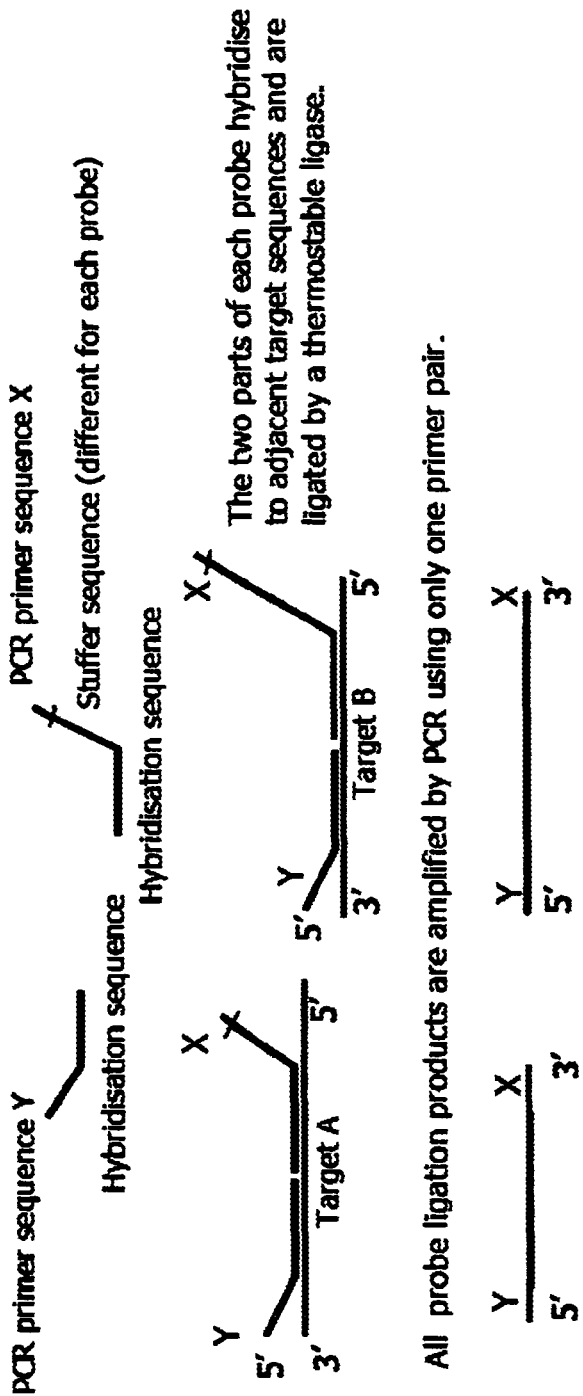
FIG. 1. A) Schematic outline of a conventional MLPA reaction. The figure is adapted from www.mpla.com.
FIG. 1B) illustrates the use of two ligation sites in one probe set, to detect two SNP's at the same time with one probe set (a Tri-Lig probe) on a specific target sequence. If the correct SNP's are present at both ligation sites, the three probe parts will become ligated together to result in one PCR product, as shown at the bottom left. If an incorrect SNP is present on one or both ligation sites, no PCR product will be formed, as shown at the bottom right.
FIG. 1C) illustrates the use of two ligation sites in one Tri-Lig probe, to detect one particular gene, KIR3DL1*024N, in the background of all other KIR3DL1 WT alleles at the first ligation site, and all other KIR genes at the second ligation site. The 1a probe detects all WT KIR3DL1 alleles (1a) whereas the 1b probe only detects the KIR3DL1*024N allele (1b), due to a different SNP at the first ligation site. The partial KIR gene sequences 2 to 12 (SEQ ID NOs 8-18) are not detected by the 1a and 1b probes, because these probes are only specific for KIR3DL1 genes at the second ligation site due to a different SNP at the second ligation site.
Figure 1B:
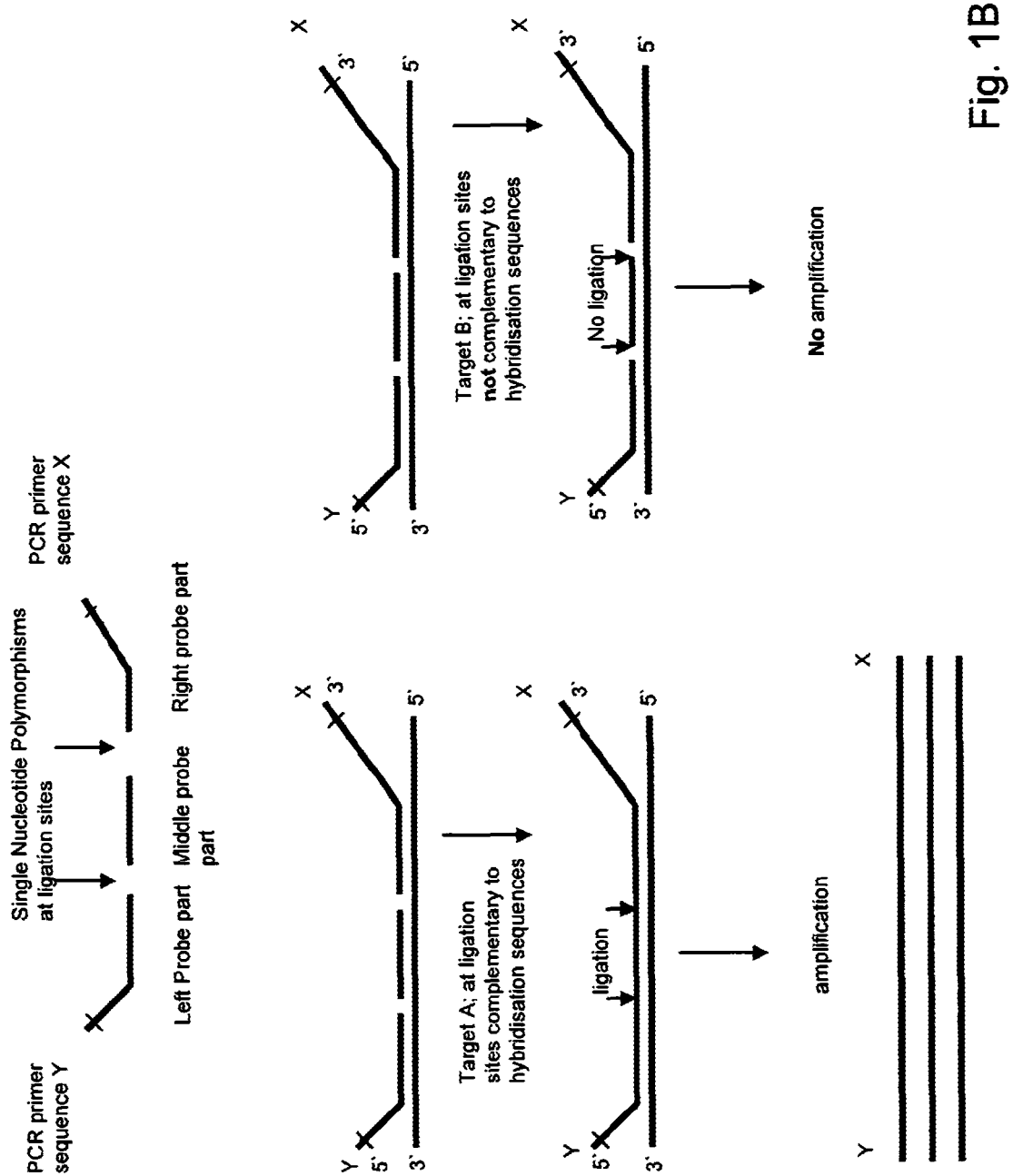

For the SSP PCR data the two haplotype models are shown to interpret possible CNV results, resp. the conventional KIR haplotype model in FIGS. 11B1 and 12B1 and the novel KIR haplotype model in FIGS. 11B2 and 12B2. FIGS. 11B3 and 12B3 show the results of our MLPA data with the extended probe sets 1 & 2 compared with both the SSP PCR data according to the conventional KIR haplotype model and with the novel KIR haplotype model.

In conventional KIR haplotype model in FIGS. 11B1 and 12B1 the KIR gene region is described by framework genes (3DL3, 3DP1, 2DL4 and 3DL2), genes that can be present in both A and B haplotypes (2DP1, 2DL1 and 2DS4) and haplotype-specific genes. The KIR genes 2DL3, 3DL1 and 2DS4 are specific for haplotype A. while the KIR genes 2DL5, 2DS1, 2DS2, 2DS3, 2DS5, 3DS1 and 2DL2 are specific for haplotype B. The haplotype A is constant to a high degree. In more than 96% of the global population haplotype A consists of 3DL3, 2DL3, 2DP1, 2DL1, 3DP1, 2DL4, 3DL1, 2DS4 and 3DL2. Haplotype B is more variable and carries more activating KIR genes.

FIGS. 11B2 and 12B2 show the interpretation for the respective families based on the novel KIR haplotype model and SSP-PCR data from CEPH-IHWG.

FIGS. 11B3 and 12B3 show the copy number variation for the respective families. In table 3 Copy number variation of KIR genes by MLPA is determined by 2 probes for each gene, except for the N-variant genes (single probe detection by definition), including those genes marked by an asterisk.

For the 3DP1v gene variant a combination of 3 probes has been designed. CNV can be deduced from a comparison between the results for the probes for 2DL5, 2DL5a and 2DL5b.

The 2DS4N KIR probe is designed to detect the KIR-2DS4 deletion-variant genes *003 to *009, while SSP-PCR only detects 2DS4 variant *003 (designated 1D).

In FIG. 12B3 KIR3DP1 variants are detected using MLPA (table 3), whereas KIR3DP1 variants are not detected when SSP-PCR is used. SSP-PCR of KIR3DP1v results in a band of 1672 bp that is obtained from the 3DP1 gene. Because this is a large fragment which are known to be difficult to detect. Therefore, a DNA sample can be positive for KIR3DP1v when MLPA is used but appear to be negative for KIR3DP1v when SSP-PCR is used.

CONCLUSION

Extended probe set 1 contains the probes 2DL1-5, 2DS1-5, 3DL1-3, 3DS1, 2DP1 and 3DP1, in total 20 probes. Extended probe set 2 contains the probes 2DL1-5, 2DS1-5, 3DL1-3, 3DS1, 2DP1 and 3DP1, in total 20 probes. Together these two probe sets are accurate for the typing of all 17 KIR genes, and 7 variant KIR gene variants (i.e. 2DL5a, 2DL5b, 3DP1v, and the null-variants 2DL4N, 3DL1N, 3DS1N, and 2DS4N), and for quantifying relative copy numbers of at least all 17 different KIR genes, and 4 null-variant (2DL4N, 3DL1N, 3DS1N, and 2DS4N) (see FIG. 13).

Example 3

The advantage of probe sets comprising three probe parts according to the present invention is that at least two different SNPs can be detected with one probe set. For instance, in a probeset consisting of three probe parts two sites for ligation are preferably present. A left probe part and middle probe part are ligated and additionally a middle probe part and right probe part are ligated. At each ligation site a SNP can be detected. With conventional MLPA probe sets, consisting of two half probes, only one SNP can be detected per probe set, because only one site for ligation is present.

Figure 1C:
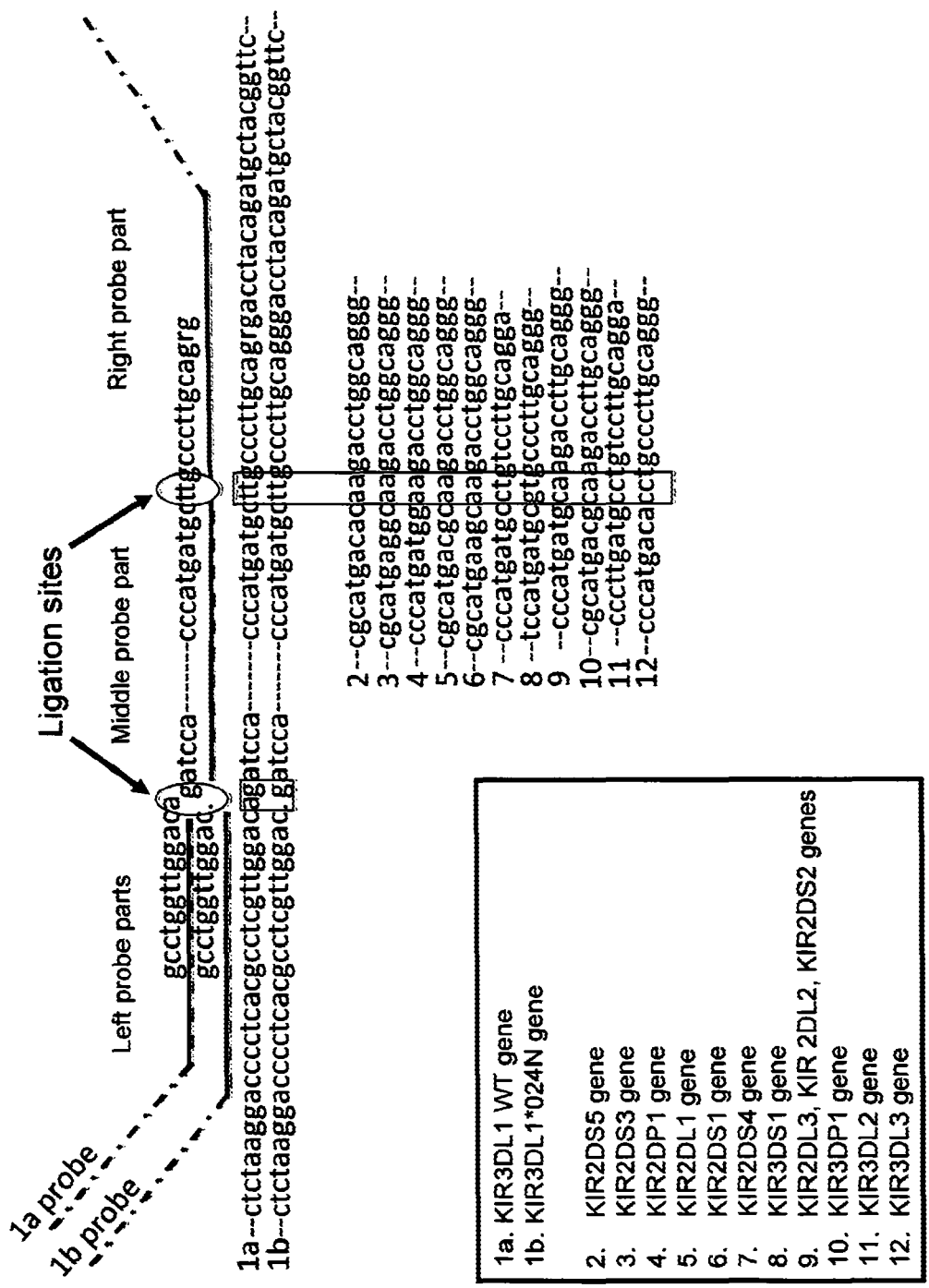

In this Example detection of the Null allele of KIR3DL1 with a probeset consisting of three probes (one left probe part, one middle probe part and one right probe part) is described. This example is illustrated in FIG. 1C.

Materials & Methods

The null allele, called KIR3DL1*024N, is discriminated from KIR3DL1 using three probes of the invention. Partial probes (probe numbers as depicted in FIG. 3C) used in this example are:

711A-KIR3DL1 WT Left probe part:
(SEQ ID No: 4)
5'-PO4 GGTTCCCTAAGGGTTGGACCCCTCACGCCTCGTTGGAC<u>A</u>-3'

711D-KIR3DL1*024N Left probe part:
(SEQ ID No: 5)
5'-PO4-GGGTTCCCTAAGGGTTGGACAAGGACCCCTCACGCCTCGTTG

GAC-3'

711B-KIR3DL1 Middle probe part:
(SEQ ID No: 6)
5'-PO4-GATCCATGATGGGGTCTCCAAGGCCAATTTCTCCATCGGTCC CATGATGC<u>T</u>-3'

711C-KIR3DL1 Right probe part:
(SEQ ID No: 7)
5'-PO4-GCCCTTGCAGGGACCTACAGATGCTACGGTTCTGGTCTAGAT

TGGATCTTGCTGGCAC-3'

For DNA selection/isolation, probe design, MLPA reaction, electrophoresis and analysis see materials & methods of example 1.

With these partial probes 2 probe sets can be formed. Those two probe sets consist of different left probe parts, but share the middle and right probe parts.

Results and Discussion

The final base of middle probe part 711B is a thymine. This thymine is specific for KIR3DL1 genes while all other KIR genes have a different base at this position. Therefore, with probe part 711B KIR3DL1 is discriminated from other KIR genes. Ligation between the middle probe part (711B) and right probe part (711C) will only occur when KIR3DL1 genes are present.

The final base of left probe part 711A is an adenine. This base is present in wildtype KIR3DL1 gene but deleted in the KIR3DL1 null allele, KIR3DL1*024N. Thus, probe part 711A containing an adenine at the final base position is specific for the wildtype KIR3DL1 gene and ligation between the 711A left probe part and the middle probe part (711B) will only occur if the KIR3DL1 wildtype gene is present. In left probe part 711D the final adenine is removed. Thus, probe part 711D is specific for null allele KIR3DL1*024N and ligation between the 711D left probe part and the middle probe part (711B) will only occur if KIR3DL1*024N is present.

Thus these two probe sets each detect 2 SNPs, namely those SNPs that are specific for KIR3DL1 wildtype gene and null allele KIR3DL1*024N because both the left probe part and the middle probe part are SNP-specific.

TABLE 1

KIR genes and proteins names, adapted from KIR Nomenclature report 2002 (Marsh et al, 2002).

| Gene symbol | Protein symbol | Aliases |
|---|---|---|
| KIR2DL1 | KIR2DL1 | cl-42, nkat1, 47.11, p58.1, CD158a |
| KIR2DL2 | KIR2DL2 | cl-43, nkat6, CD158b1 |
| KIR2DL3 | KIR2DL3 | cl-6, nkat2, nkat2a, nkat2b, p58, CD158b2 |
| KIR2DL4 | KIR2DL4 | 103AS, 15.212, CD158d |
| KIR2DL5A | KIR2DL5A | KIR2DL5.1, CD158f |
| KIR2DL5B | KIR2DL5B | KIR2DL5.2, KIR2DL5.3, KIR2DL5.4 |
| KIR2DS1 | KIR2DS1 | EB6ActI, EB6ActII, CD158h |
| KIR2DS2 | KIR2DS2 | cl-49, nkat5, 183ActI, CD158j |
| KIR2DS3 | KIR2DS3 | nkat7 |
| KIR2DS4 | KIR2DS4 | cl-39, KKA3, nkat8, CD158i |
| KIR2DS5 | KIR2DS5 | nkat9, CD158g |
| KIR2DP1 | KIR2DP1 | KIRZ, KIRY, KIR15, KIR2DL6 |
| KIR3DL1 | KIR3DL1 | cl-2, NKB1, cl-11, nkat3, NKB1B, AMB11, KIR, CD158e1 |
| KIR3DL2 | KIR3DL2 | cl-5, nkat4, nkat4a, nkat4b, CD158k |
| KIR3DL3 | KIR3DL3 | KIRC1, KIR3DL7, KIR44, CD158z |
| KIR3DS1 | KIR3DS1 | nkat10, CD158e2 |
| KIR3DP1 | KIR3DP1 | KIRX, KIR48, KIR2DS6, KIR3DS2P, CD158c |

TABLE 2

Number of currently known alleles for each KIR gene and the different protein products they encode (IPD KIR database).

| Gene | 2DL1 | 2DL2 | 2DL3 | 2DL4 | 2DL5 | 2DS1 | 2DS2 | 2DS3 |
|---|---|---|---|---|---|---|---|---|
| Alleles | 25 | 11 | 9 | 25 | 21 | 12 | 12 | 9 |
| Proteins | 28 | 7 | 8 | 12 | 11 | 8 | 6 | 3 |

| Gene | 2DS4 | 2DS5 | 3DL1 | 3DS1 | 3DL2 | 3DL3 | 2DP1 | 3DP1 |
|---|---|---|---|---|---|---|---|---|
| Alleles | 20 | 12 | 52 | 14 | 45 | 55 | 5 | 8 |
| Proteins | 13 | 9 | 46 | 12 | 40 | 31 | 0 | 0 |

TABLE 3

KIRs and their cognate ligands (Carrington et al, 2003; Middleton et al, 2005; Du et al, 2007). The ligands of the other KIRs are unknown or uncertain.

| Inhibitory KIRs | Ligands | Activating KIRs | Ligands |
|---|---|---|---|
| 2DL1 | HLA-C group 2, allotypes Cw 1, 4, 5, 6, 17, 18 | 2DS1 | HLA-C group 2 allotypes Cw 1, 4, 5, 6, 17, 18 |

TABLE 3-continued

KIRs and their cognate ligands (Carrington et al, 2003; Middleton et al, 2005; Du et al, 2007). The ligands of the other KIRs are unknown or uncertain.

| Inhibitory KIRs | Ligands | Activating KIRs | Ligands |
|---|---|---|---|
| 2DL2 and 2DL3 | HLA-C group 1, allotypes Cw 1, 3, 7, 8, 13, 14 | 2DS2 | HLA group 1, allotypes Cw 1, 3, 7, 8, 13, 14 |
| 2DL4 | HLA-G | 2DS4 | HLA-C |
| 3DL1 | HLA-B, Bw4 | 3DS1 | HLA-B, Bw4 |
| 3DL2 | HLA-A3 and A11 allotypes | | |

TABLE 4

The KIR Reference Panel I from the IHWG

| | IHW # | Family # | 3DL3 | 2DS2 | 2DL2 | 2DL3 | 2DP1 | 2DL1 | 3DP1 | 3DP1v | 2DL4 | 3DL1 | 3DS1 | 2DL5 | 2DS3 | 2DS5 | 2DS1 | 2DS4 | 1D | 3DL2 |
|---|---|---|---|---|---|---|---|---|---|---|---|---|---|---|---|---|---|---|---|---|
| 1 | IHW01003 | 1331-8233 | 1 | 0 | 0 | 1 | 1 | 1 | 1 | 0 | 1 | 1 | 0 | 0 | 0 | 0 | 0 | 0 | 1 | 1 |
| 2 | IHW01010 | 1331-8240 | 1 | 0 | 0 | 1 | 1 | 1 | 1 | 0 | 1 | 1 | 0 | 0 | 0 | 0 | 0 | 1 | 1 | 1 |
| 3 | IHW01016 | 1331-8240 | 1 | 0 | 0 | 1 | 1 | 1 | 1 | 0 | 1 | 1 | 0 | 0 | 0 | 0 | 0 | 0 | 1 | 1 |
| 4 | IHW01017 | 1331-8549 | 1 | 0 | 0 | 1 | 1 | 1 | 1 | 0 | 1 | 1 | 0 | 0 | 0 | 0 | 0 | 1 | 1 | 1 |
| 5 | IHW01018 | 1332-1133 | 1 | 0 | 0 | 1 | 1 | 1 | 1 | 0 | 1 | 1 | 0 | 0 | 0 | 0 | 0 | 1 | 1 | 1 |
| 6 | IHW01021 | 1332-8252 | 1 | 0 | 0 | 1 | 1 | 1 | 1 | 0 | 1 | 1 | 1 | 1 | 0 | 1 | 1 | 0 | 1 | 1 |
| 7 | IHW01029 | 1332-8260 | 1 | 0 | 0 | 1 | 1 | 1 | 1 | 0 | 1 | 1 | 0 | 0 | 0 | 0 | 0 | 1 | 1 | 1 |
| 8 | IHW01031 | 1332-8262 | 1 | 0 | 0 | 1 | 1 | 1 | 1 | 0 | 1 | 1 | 1 | 1 | 0 | 1 | 1 | 0 | 1 | 1 |
| 9 | IHW01040 | 1333-8276 | 1 | 1 | 1 | 0 | 1 | 1 | 1 | 1 | 1 | 1 | 0 | 1 | 1 | 0 | 0 | 0 | 1 | 1 |
| 10 | IHW01044 | 1333-8280 | 1 | 1 | 1 | 1 | 1 | 1 | 1 | 0 | 1 | 1 | 0 | 1 | 1 | 0 | 0 | 0 | 1 | 1 |
| 11 | IHW01045 | 1333-8281 | 1 | 1 | 1 | 1 | 1 | 1 | 1 | 0 | 1 | 1 | 1 | 1 | 0 | 1 | 0 | 0 | 1 | 1 |
| 12 | IHW01046 | 1333-8282 | 1 | 1 | 1 | 1 | 1 | 1 | 1 | 1 | 1 | 1 | 0 | 0 | 0 | 0 | 0 | 0 | 1 | 1 |
| 13 | IHW01052 | 1341-8313 | 1 | 1 | 1 | 0 | 0 | 0 | 0 | 1 | 1 | 1 | 0 | 0 | 0 | 0 | 0 | 1 | 1 | 1 |
| 14 | IHW01053 | 1341-8314 | 1 | 1 | 1 | 0 | 0 | 0 | 0 | 1 | 1 | 1 | 0 | 0 | 0 | 0 | 0 | 0 | 1 | 1 |
| 15 | IHW01056 | 1341-8317 | 1 | 1 | 1 | 1 | 1 | 1 | 1 | 1 | 1 | 1 | 0 | 0 | 0 | 0 | 0 | 1 | 1 | 1 |
| 16 | IHW01060 | 1341-8346 | 1 | 1 | 1 | 0 | 0 | 0 | 0 | 1 | 1 | 1 | 0 | 0 | 0 | 0 | 0 | 1 | 1 | 1 |
| 17 | IHW01069 | 1344-8348 | 1 | 0 | 0 | 1 | 1 | 1 | 1 | 0 | 1 | 1 | 0 | 0 | 0 | 0 | 0 | 0 | 1 | 1 |
| 18 | IHW01074 | 1344-8353 | 1 | 0 | 0 | 1 | 1 | 1 | 1 | 0 | 1 | 1 | 0 | 0 | 0 | 0 | 0 | 0 | 1 | 1 |
| 19 | IHW01077 | 1344-8356 | 1 | 0 | 0 | 1 | 1 | 1 | 1 | 0 | 1 | 1 | 0 | 0 | 0 | 0 | 0 | 0 | 1 | 1 |
| 20 | IHW01078 | 1344-8370 | 1 | 0 | 0 | 1 | 1 | 1 | 1 | 0 | 1 | 1 | 0 | 0 | 0 | 0 | 0 | 0 | 1 | 1 |
| 21 | IHW01080 | 1346-8357 | 1 | 1 | 1 | 1 | 1 | 1 | 1 | 1 | 1 | 1 | 0 | 0 | 0 | 0 | 0 | 1 | 1 | 1 |
| 22 | IHW01085 | 1346-8362 | 1 | 1 | 1 | 1 | 1 | 1 | 1 | 1 | 1 | 1 | 0 | 0 | 0 | 0 | 0 | 1 | 0 | 1 |
| 23 | IHW01088 | 1346-8365 | 1 | 0 | 0 | 1 | 1 | 1 | 1 | 0 | 1 | 1 | 0 | 0 | 0 | 0 | 0 | 1 | 1 | 1 |
| 24 | IHW01091 | 1346-8438 | 1 | 1 | 1 | 1 | 1 | 1 | 1 | 1 | 1 | 1 | 0 | 0 | 0 | 0 | 0 | 1 | 1 | 1 |
| 25 | IHW01096 | 1347-8412 | 1 | 0 | 0 | 1 | 1 | 1 | 1 | 0 | 1 | 1 | 1 | 1 | 1 | 0 | 1 | 1 | 0 | 1 |
| 26 | IHW01101 | 1347-8436 | 1 | 1 | 1 | 0 | 1 | 1 | 1 | 1 | 1 | 1 | 1 | 1 | 0 | 1 | 1 | 0 | 1 | 1 |
| 27 | IHW01103 | 1347-8440 | 1 | 1 | 1 | 1 | 1 | 1 | 1 | 0 | 1 | 0 | 1 | 1 | 1 | 0 | 1 | 0 | 0 | 1 |
| 28 | IHW01108 | 1347-8445 | 1 | 1 | 1 | 1 | 1 | 1 | 1 | 1 | 1 | 1 | 0 | 0 | 0 | 0 | 0 | 1 | 0 | 1 |
| 29 | IHW01111 | 1349-8393 | 1 | 0 | 0 | 1 | 1 | 1 | 1 | 0 | 1 | 1 | 1 | 1 | 1 | 0 | 1 | 0 | 1 | 1 |
| 30 | IHW01116 | 1349-8398 | 1 | 0 | 0 | 1 | 1 | 1 | 1 | 0 | 1 | 1 | 1 | 1 | 1 | 0 | 1 | 0 | 1 | 1 |
| 31 | IHW01117 | 1349-8399 | 1 | 0 | 0 | 1 | 1 | 1 | 1 | 0 | 1 | 1 | 0 | 0 | 0 | 0 | 0 | 0 | 1 | 1 |
| 32 | IHW01122 | 1349-8636 | 1 | 0 | 0 | 1 | 1 | 1 | 1 | 0 | 1 | 1 | 0 | 0 | 0 | 0 | 0 | 0 | 1 | 1 |
| 33 | IHW01124 | 1362-8563 | 1 | 1 | 1 | 1 | 1 | 1 | 1 | 1 | 1 | 1 | 0 | 0 | 0 | 0 | 0 | 0 | 1 | 1 |
| 34 | IHW01130 | 1362-8569 | 1 | 1 | 1 | 1 | 1 | 1 | 1 | 1 | 1 | 1 | 0 | 0 | 0 | 0 | 0 | 0 | 1 | 1 |
| 35 | IHW01131 | 1362-8570 | 1 | 0 | 0 | 1 | 1 | 1 | 1 | 0 | 1 | 1 | 0 | 0 | 0 | 0 | 0 | 0 | 1 | 1 |
| 36 | IHW01135 | 1362-8574 | 1 | 0 | 0 | 1 | 1 | 1 | 1 | 0 | 1 | 1 | 1 | 0 | 1 | 1 | 0 | 1 | 1 | 1 |
| 37 | IHW01140 | 1408-1011 | 1 | 1 | 1 | 1 | 1 | 1 | 1 | 1 | 1 | 1 | 1 | 1 | 0 | 1 | 1 | 0 | 1 | 1 |
| 38 | IHW01141 | 1408-1012 | 1 | 0 | 0 | 1 | 1 | 1 | 1 | 0 | 1 | 1 | 1 | 1 | 0 | 1 | 1 | 0 | 1 | 1 |
| 39 | IHW01143 | 1408-1014 | 1 | 1 | 1 | 1 | 1 | 1 | 1 | 1 | 1 | 1 | 1 | 1 | 0 | 1 | 1 | 0 | 1 | 1 |
| 40 | IHW01145 | 1408-1016 | 1 | 1 | 1 | 1 | 1 | 1 | 1 | 1 | 1 | 1 | 1 | 1 | 0 | 1 | 1 | 0 | 1 | 1 |
| 41 | IHW01160 | 1413-1083 | 1 | 1 | 1 | 1 | 1 | 1 | 1 | 1 | 1 | 1 | 0 | 0 | 0 | 0 | 0 | 0 | 1 | 1 |
| 42 | IHW01161 | 1413-1084 | 1 | 1 | 1 | 0 | 1 | 0 | 0 | 1 | 1 | 1 | 0 | 0 | 0 | 0 | 0 | 0 | 1 | 1 |
| 43 | IHW01162 | 1413-1085 | 1 | 0 | 0 | 1 | 1 | 1 | 1 | 0 | 1 | 1 | 0 | 0 | 0 | 0 | 0 | 1 | 1 | 1 |
| 44 | IHW01166 | 1413-1089 | 1 | 1 | 1 | 1 | 1 | 1 | 1 | 0 | 1 | 1 | 1 | 1 | 1 | 0 | 0 | 0 | 1 | 1 |
| 45 | IHW01175 | 1416-1188 | 1 | 1 | 1 | 1 | 1 | 1 | 1 | 1 | 1 | 1 | 1 | 1 | 1 | 0 | 0 | 0 | 1 | 1 |
| 46 | IHW01181 | 1416-1194 | 1 | 0 | 0 | 1 | 1 | 1 | 1 | 0 | 1 | 1 | 0 | 0 | 0 | 0 | 0 | 0 | 1 | 1 |
| 47 | IHW01182 | 1416-1195 | 1 | 0 | 0 | 1 | 1 | 1 | 1 | 0 | 1 | 1 | 1 | 1 | 0 | 1 | 0 | 1 | 1 | 1 |
| 48 | IHW01184 | 1416-1197 | 1 | 1 | 1 | 1 | 1 | 1 | 1 | 1 | 1 | 1 | 1 | 1 | 0 | 0 | 0 | 1 | 1 | 1 |

2DS4 indicates all alleles except KIR2DS4*003 and 1D indicates only KIR2DS4*003.

3DP1 indicates KIR3DP1*003 (deletion of exon 2) only and 3DP1v indicates all alleles except KIR3DP1*003

Note:

"1" = presence of KIR gene

"0" = absence of KIR gene shaded cells (N = 16) represent four informative families selected for the Phase II reference panel

TABLE 5

The 17 KIR probes that have been designed and tested for probe set 1. The size of the complete MLPA probe and the size of the separate probe parts and the concentration used are listed in this table.

| Code | Probe | Size [bp] | Probe Part | Size [bp] | Concentration (fmol) |
|---|---|---|---|---|---|
| 420A | 2DL2 | 96 | Left | 48 | 1 |
| 420B | | | Right | 48 | |
| 512A | 3DL3 | 100 | Left | 50 | 1 |
| 512B | | | Right | 50 | |
| 540A | 2DS3 | 108 | Left | 54 | 10 |
| 540B | | | Right | 54 | |
| 404A | 3DL2 | 112 | Left | 56 | 1 |
| 404B | | | Right | 56 | |
| 405A | 2DP1 | 121 | Left | 65 | 1 |
| 405B | | | Right | 56 | |
| 406A | 3DP1 | 125 | Left | 66 | 1 |
| 406B | | | Right | 59 | |
| 504A | 2DS4 | 137 | Left | 61 | 1 |
| 504B | | | Right | 76 | |
| 408A | 2DL5 | 142 | Left | 57 | 1 |
| 408B | | | Middle | 32 | |
| 408C | | | Right | 53 | |
| 514A | 3DL1 | 149 | Left | 74 | 1 |
| 514B | | | Right | 75 | |
| 526A | 2DS2 | 154 | Left | 57 | 1 |
| 526B | | | Middle | 34 | |
| 526C | | | Right | 63 | |
| 507A | 2DL5A | 165 | Left | 66 | 1 |
| 507B | | | Middle | 32 | |
| 507C | | | Right | 67 | |
| 419A | 2DL4 | 170 | Left | 59 | 1 |
| 419B | | | Middle | 54 | |
| 419C | | | Right | 57 | |
| 528A | 2DS5 | 185 | Left | 67 | 1 |
| 528B | | | Middle | 47 | |
| 528C | | | Right | 71 | |
| 413A | 2DL1 | 189 | Left | 72 | 1 |
| 413B | | | Middle | 64 | |
| 413C | | | Right | 53 | |
| 416A | 2DS1 | 195 | Left | 78 | 10 |
| 416B | | | Middle | 67 | |
| 416C | | | Right | 50 | |
| 415A | 2DL3 | 213 | Left | 75 | 10 |
| 415B | | | Middle | 69 | |
| 415C | | | Right | 69 | |
| 418A | 3DS1 | 218 | Left | 81 | 10 |
| 418B | | | Middle | 64 | |
| 418C | | | Right | 73 | |

TABLE 6

The 17 KIR probes that have been designed and tested for probe set 2. The size of the complete MLPA probe and the size of the separate probe parts and the concentration used are listed in this table.

| Code | Probe | Size [bp] | Probe Part | Size [bp] | Concentration (fmol) |
|---|---|---|---|---|---|
| 543A | 2DS1 | 96 | Left | 48 | 10 |
| 543B | | | Right | 48 | |
| 544A | 2DS2 | 100 | Left | 50 | 1 |
| 544B | | | Right | 50 | |
| 537A | 2DL5 | 108 | Left | 54 | 1 |
| 537B | | | Right | 54 | |
| 513D | 2DS3 | 112 | Left | 52 | 10 |
| 513B | | | Right | 60 | |
| 518A | 3DP1 | 121 | Left | 61 | 1 |
| 518B | | | Right | 60 | |
| 542A | 2DP1 | 125 | Left | 60 | 1 |
| 542B | | | Right | 65 | |
| 541A | 3DS1 | 134 | Left | 67 | 10 |
| 541B | | | Right | 67 | |
| 524A | 2DS4 | 137 | Left | 66 | 10 |
| 524B | | | Right | 71 | |
| 545A | 2DS5 | 144 | Left | 68 | 10 |
| 545B | | | Right | 76 | |
| 409A | 3DL1 | 149 | Left | 60 | 10 |
| 409B | | | Middle | 34 | |
| 409C | | | Right | 55 | |
| 506A | 3DL3 | 154 | Left | 54 | 10 |
| 506B | | | Middle | 48 | |
| 506C | | | Right | 52 | |
| 507A | 2DL5A | 165 | Left | 66 | 1 |
| 507B | | | Middle | 32 | |
| 507C | | | Right | 67 | |
| 539A | 2DL2 | 170 | Left | 60 | 1 |
| 539B | | | Middle | 46 | |
| 539C | | | Right | 64 | |
| 525A | 2DL1 | 190 | Left | 64 | 10 |
| 525B | | | Middle | 62 | |
| 525C | | | Right | 64 | |
| 538A | 3DL2 r | 195 | Left | 70 | 1 |
| 538B | | | Middle | 60 | |
| 538C | | | Right | 65 | |
| 417A | 2DL3 | 213 | Left | 75 | 10 |
| 417B | | | Middle | 69 | |
| 417C | | | Right | 69 | |
| 517A | 2DL4 | 218 | Left | 73 | 10 |
| 517B | | | Middle | 68 | |
| 517C | | | Right | 77 | |

TABLE 7

The control probes used in the two probes sets. The size of the complete MLPA probe and the size of the separate probe parts and the concentration used for the probe sets are listed in this table.

| Code | Probe (Gene) | Size [bp] | Probe part | Size [bp] | Concentration (fmol) |
|---|---|---|---|---|---|
| 201 | Ctrl 2 (FGF3) | 92 | Left | 45 | 1 |
| | | | Right | 47 | |
| 202 | Ctrl 3 (BCAS4) | 104 | Left | 52 | 1 |
| | | | Right | 52 | |
| 203 | Ctrl 4 (LMNA) | 116 | Left | 58 | 1 |
| | | | Right | 58 | |
| 204 | Ctrl 5 (PARK2) | 130 | Left | 44 | 3 |
| | | | Middle | 41 | |
| | | | Right | 45 | |
| 205 | Ctrl 7 (MSH6) | 160 | Left | 59 | 1 |
| | | | Middle | 42 | |
| | | | Right | 59 | |
| 206 | Ctrl 8 (GALT) | 175 | Left | 58 | 1 |
| | | | Middle | 59 | |
| | | | Right | 58 | |
| 207 | Ctrl 9 (SPG4) | 180 | Left | 60 | 1 |
| | | | Middle | 60 | |
| | | | Right | 60 | |
| 210 | Ctrl 1 (IL-4) | 208 | Left | 73 | 1 |
| | | | Middle | 69 | |
| | | | Right | 66 | |
| 209 | Ctrl 10 (NF2) | 223 | Left | 78 | 1 |
| | | | Middle | 69 | |
| | | | Right | 76 | |

TABLE 8

The competitors of the control probes. The size of the competitor, the part of the control probes used and concentration used for the probe sets are listed in this table.

| code | gene | length [bp] | probe part | Concentration (fmol) |
|---|---|---|---|---|
| 201X | Ctrl 2 (FGF3) | 30 | Left | 10 |
| 202X | Ctrl 3 (BCAS4) | 30 | Left | 10 |
| 203X | Ctrl 4 (LMNA) | 30 | Left | 3 |

TABLE 8-continued

The competitors of the control probes. The size of the competitor, the part of the control probes used and concentration used for the probe sets are listed in this table.

| code | gene | length [bp] | probe part | Concentration (fmol) |
|---|---|---|---|---|
| 205X | Ctrl 7 (MSH6) | 50 | Left | 0 |
| 207X | Ctrl 9 (SPG4) | 50 | Left | 1 |

TABLE 9

KIR gene frequencies in the Caucasian population.

| KIR2DL1 | KIR2DL2 | KIR2DL3 | K1R2DL4 | KIR2DL5 | KIR2DS1 | KIR2DS2 | KIR2DS3 |
|---|---|---|---|---|---|---|---|
| 88-100% | 39-63% | 57-94% | 100% | 36-61% | 27-49% | 25-63% | 19-42% |

| KIR2DS4 | KIR2DS5 | KIR3DL1 | KIR3DL2 | KIR3DL3 | KIR3DS1 | KIR2DP1 | KIR3DP1 |
|---|---|---|---|---|---|---|---|
| 87-98% | 21-46% | 76-98% | 99-100% | 99-100% | 26-50% | 94-100% | 97-100% |

The frequencies are derived from several studies performed worldwide in the Caucasian population.

TABLE 10

KIR alleles detected by the probes and the coverage of the total KIR alleles, except for 3DP1v, by probe sets 1 and 2, as depicted in FIG. 3A and 3B.

| | Probe set 1 | | | Probe set 2 | | | Probe set 1 + 2 |
|---|---|---|---|---|---|---|---|
| PROBE | ALLELES | | COVERAGE | PROBE | ALLELES | | COVERAGE | COVERAGE |
| 2DL1 | 2DL1*001 2DL1*002 2DL1*00301 2DL1*0030201 2DL1*0030202 2DL1*00303 2DL1*0040101 2DL1*0040102 | 2DL1*00402 2DL1*005 2DL1*006 2DL1*007 2DL1*008 2DL1*009 2DL1*010 | 100% | 2DL1 | 2DL1*001 2DL1*002 2DL1*00301 2DL1*0030201 2DL1*0030202 2DL1*00303 2DL1*0040101 2DL1*0040102 | 2DL1*00402 2DL1*005 2DL1*006 2DL1*007 2DL1*008 2DL1*009 2DL1*010 | 100% | 100% |
| 2DL2 | 2DL2*001 2DL2*002 2DL2*003 | 2DL2*004 2DL2*005 | 100% | 2DL2 | 2DL2*001 2DL2*002 | 2DL2*003 2DL2*005 | 80% | 100% |
| 2DL3 | 2DL3*001 2DL3*002 2DL3*003 | 2DL3*004 2DL3*005 2DL3*006 | 86% | 2DL3 | 2DL3*001 2DL3*002 2DL3*003 2DL3*004 | 2DL3*005 2DL3*006 2DL3*007 | 100% | 100% |
| 2DL4 | 2DL4*00101 2DL4*00102 2DL4*00105 2DL4*00201 2DL4*00202 2DL4*003 2DL4*004 | 2DL4*00501 2DL4*00601 2DL4*00602 2DL4*007 2DL4*0080101 2DL4*0080201 2DL4*011 | 54% | 2DL4 | 2DL4*00101 2DL4*00102 2DL4*0010301 2DL4*0010302 2DL4*00104 2DL4*00105 2DL4*00201 2DL4*00202 2DL4*00203 2DL4*003 2DL4*004 2DL4*00501 2DL4*00502 | 2DL4*00601 2DL4*00602 2DL4*007 2DL4*0080101 2DL4*0080102 2DL4*0080103 2DL4*0080104 2DL4*0080201 2DL4*0080202 2DL4*009 2DL4*010 2DL4*011 2DL4*012 | 100% | 100% |
| 2DL5 | 2DL5A*0010101 2DL5A*0010102 2DL5A*0050101 2DL5A*0050102 2DL5B*0020101 2DL5B*0020102 2DL5B*0020103 | 2DL5B*003 2DL5B*004 2DL5B*00601 2DL5B*007 2DL5B*00801 2DL5B*009 | 100% | 2DL5 | 2DL5A*0010101 2DL5A*0010102 2DL5B*003 2DL5B*004 | 2DL5B*00601 2DL5B*007 2DL5B*00801 | 54% | 100% |
| 2DL5A | 2DL5A*0010101 2DL5A*0010W2 3DP1*004 3DP1v | 2DL5A*0050101 2DL5A*0050102 | 100% 14% | 2DL5A | Same probe as in probe set 1. | | 100% | 100% |
| 2DS1 | No match found in the KIR database. BLAST result in match with KIR2DS1v alias KIR2DS1*002 | | | 2DS1 | No match found in the KIR database. Probe designed on intron 6. | | | |

TABLE 10-continued

KIR alleles detected by the probes and the coverage of the total KIR alleles,
except for 3DP1v, by probe sets 1 and 2, as depicted in FIG. 3A and 3B.

| | Probe set 1 | | | | Probe set 2 | | | Probe set 1 + 2 |
|---|---|---|---|---|---|---|---|---|
| PROBE | ALLELES | | COVERAGE | PROBE | ALLELES | | COVERAGE | COVERAGE |
| 2DS2 | 2DS2*0010101<br>2DS2*0010102<br>2DS2*0010103<br>2DS2*00102<br>2DS2*00103 | 2DS2*002<br>2DS2*003<br>2DS2*004<br>2DS2*005 | 90% | 2DS2 | No match found in the KIR database. Probe designed on intron 2 and 3. | | | 90% |
| 2DS3 | 2DS3*00101<br>2DS3*00102<br>2DS3*00103 | 2DS3*002<br>2DS3*003N<br>2DS3*004 | 100% | 2DS3 | 2DS3*00101<br>2DS3*00102<br>2DS3*00103 | 2DS3*002<br>2DS3*003N<br>2DS3*004 | 100% | 100% |
| 2DS4 | 2DS4*0010101<br>2DS4*0010102<br>2DS4*0010103<br>2DS4*00102<br>2DS4*00103 | 2DS4*003<br>2DS4*004<br>2DS4*006<br>2DS4*007<br>2DS4*009 | 100% | 2DS4 | 2DS4*0010101<br>2DS4*0010102<br>2DS4*0010103<br>2DS4*00102 | 2DS4*003<br>2DS4*006<br>2DS4*007<br>2DS4*009 | 80% | 100% |
| 2DS5 | 2DS5*001<br>2DS5*0020101<br>2DS5*0020102<br>2DS5*0020103<br>2035*003 | 2DS5*004<br>2DS5*005<br>2DS5*006<br>2DS5*007<br>2DS5*008 | 100% | 2DS5 | 2DS5*001<br>2DS5*0020101<br>2DS5*0020102<br>2DS5*0020103<br>2DS5*003 | 2DS5*004<br>2DS5*005<br>2DS5*006<br>2DS5*007<br>2DS5*008 | 100% | 100% |
| 3DL1 | 3DL1*00101<br>3DL1*00102<br>3DL1*002<br>3DL1*00401<br>3DL1*00402<br>3DL1*00501<br>3DL1*00502<br>3DL1*007<br>3DL1*008<br>3DL1*009<br>3DL1*01501<br>3DL1*01502<br>3DL1*016<br>3DL1*01701<br>3DL1*01702<br>3DL1*018<br>3DL1*024N<br>3DL1*025<br>3DL1*026 | 3DL1*027<br>3DL1*028<br>3DL1*029<br>3DL1*030<br>3DL1*031<br>3DL1*032<br>3DL1*033<br>3DL1*034<br>3DL1*035<br>3DL1*036<br>3DL1*037<br>3DL1*038<br>3DL1*039<br>3DL1*040<br>3DL1*041<br>3DL1*042<br>3DL1*043<br>3DL1*044<br>3DL1*057 | 78% | 3DL1 | 3DL1*00101<br>3DL1*002<br>3DL1*00401<br>3DL1*00402<br>3DL1*00501<br>3DL1*00502<br>3DL1*006<br>3DL1*007<br>3DL1*008<br>3DL1*009 | 3DL1*021<br>3DL1*022<br>3DL1*023<br>3DL1*024N<br>3DL1*025<br>3DL1*026<br>3DL1*027<br>3DL1*028<br>3DL1*029<br>3DL1*030 | 41% | 88% |
| 3DL2 | 3DL2*00101<br>3DL2*002<br>3DL2*00301<br>3DL2*004<br>3DL2*005<br>3DL2*0070101<br>3DL2*0070102<br>3DL2*008<br>3DL2*00901 | 3DL2*00902<br>3DL2*013<br>3DL2*014<br>3DL2*016<br>3DL2*017<br>3DL2*018<br>3DL2*019<br>3DL2*020<br>3DL2*021 | 47% | 3DL2 | 3DL2*00101<br>3DL2*002<br>3DL2*00301<br>3DL2*004<br>3DL2*005<br>3DL2*006<br>3DL2*0070101<br>3DL2*0070102<br>3DL2*008 | 3DL2*010<br>3DL2*011<br>3DL2*012<br>3DL2*013<br>3DL2*015<br>3DL2*016<br>3DL2*020<br>3DL2*021 | 45% | 61% |
| 3DL3 | 3DL3*00101<br>3DL3*00102<br>3DL3*00103<br>3DL3*00201<br>3DL3*00203<br>3DL3*00204<br>3DL3*00205<br>3DL3*00207<br>3DL3*0030101<br>3DL3*0030102<br>3DL3*00401<br>3DL3*00402<br>3DL3*005<br>3DL3*00601<br>3DL3*00602<br>3DL3*00801<br>3DL3*00802<br>3DL3*00901<br>3DL3*00902<br>3DL3*010<br>3DL3*01101 | 3DL3*01102<br>3DL3*012<br>3DL3*01301<br>3DL3*01303<br>3DL3*01304<br>3DL3*01401<br>3DL3*01403<br>3DL3*01405<br>3DL3*015<br>3DL3*016<br>3DL3*017<br>3DL3*018<br>3DL3*020<br>3DL3*021<br>3DL3*022<br>3DL3*023<br>3DL3*024<br>3DL3*025<br>3DL3*026<br>3DL3*028 | 75% | 3DL3 | 3DL3*00101<br>3DL3*00102<br>3DL3*00103<br>3DL3*00201<br>3DL3*00202<br>3DL3*00203<br>3DL3*00204<br>3DL3*00205<br>3DL3*00206<br>3DL3*00207<br>3DL3*0030101<br>3DL3*0030102<br>3DL3*00401<br>3DL3*00402<br>3DL3*005<br>3DL3*00601<br>3DL3*00602<br>3DL3*007<br>3DL3*00801<br>3DL3*00802<br>3DL3*00901<br>3DL3*00902<br>3DL3*010<br>3DL3*01101<br>3DL3*01102<br>3DL3*012 | 3DL3*01303<br>3DL3*01304<br>3DL3*01305<br>3DL3*01306<br>3DL3*01307<br>3DL3*01401<br>3DL3*01402<br>3DL3*01403<br>3DL3*01404<br>3DL3*01405<br>3DL3*015<br>3DL3*016<br>3DL3*017<br>3DL3*018<br>3DL3*019<br>3DL3*020<br>3DL3*021<br>3DL3*022<br>3DL3*023<br>3DL3*024<br>3DL3*025<br>3DL3*026<br>3DL3*027<br>3DL3*028<br>3DL3*029<br>3DL3*030 | 100% | 100% |

TABLE 10-continued

KIR alleles detected by the probes and the coverage of the total KIR alleles, except for 3DP1v, by probe sets 1 and 2, as depicted in FIG. 3A and 3B.

| | Probe set 1 | | | | Probe set 2 | | | Probe set 1 + 2 |
|---|---|---|---|---|---|---|---|---|
| PROBE | ALLELES | | COVERAGE | PROBE | ALLELES | | COVERAGE | COVERAGE |
| | | | | | 3DL3*01301 | 3DL3*031 | | |
| | | | | | 3DL3*01302 | | | |
| 3DS1 | 3DS1*010 | 3DS1*046 | 71% | 3DS1 | 3DS1*010 | 3DS1*045 | 71% | 86% |
| | 3DS1*01301 | 3DS1*047 | | | 3DS1*011 | 3DS1*046 | | |
| | 3DS1*01302 | 3DS1*048 | | | 3DS1*012 | 3DS1*047 | | |
| | 3DS1*014 | 3DS1*049N | | | 3DS1*01301 | 3DS1*048 | | |
| | 3DS1*045 | 3DS1*055 | | | 3DS1*01302 | 3DS1*049N | | |
| 2DP1 | 2DP1*00101 | 2DP1*0020102 | 100% | 2DP1 | 2DP1*00101 | 2DP1*0020102 | 100% | 100% |
| | 2DP1*00102 | 2DP1*003 | | | 2DP1*00102 | 2DP1*003 | | |
| | 2DP1*0020101 | | | | 2DP1*0020101 | | | |
| 3DP1 | 3DP1*001 | 3DP1*004 | 100% | 3DP1 | No match found on the KIR database. Detects deletion of exon 2. | | | 100% |
| | 3DP1*002 | 3DP1*005 | | | | | | |
| | 3DP1*00301 | 3DP1*006 | | | | | | |
| | 3DP1*00302 | | | | | | | |

All KIR alleles including 3DP1v are also detected by extended probe sets 1 and 2, as depicted in FIG. 3C and 3D Coverage lower then 100% are caused by gene variants that are present in the target sequence to which the probes bind. The alleles shown here that can be detected by the probes are generated with the primer or probe blast tool on the IPD KIR database. The percentage of the total KIR alleles that can be covered by the probes is calculated by dividing the number of alleles for each probe by the number of total alleles that is reported on the website. Certain alleles are underlined where the coverage of both probe sets is not 100% due to gene variants present in the target sequence.

TABLE 11

Verification of KIR MLPA probe set 1 on 11 cell lines KIR-genotyped by the $10^{th}$ IHW.

| CODE | NAME | 2DL1 | 2DL2 | 2DL3 | 2DL4 | 2DL5 | 2DL5A | 2DS1 | 2DS2 | 2DS3 | 2DS4 | 2DS5 | 3DL1 | 3DL2 | 3DL3 | 3DS1 | 2DP1 | 3DP1 |
|---|---|---|---|---|---|---|---|---|---|---|---|---|---|---|---|---|---|---|
| 231 | JVM | 1 | 1 | 1 | 1 | 0 | 4 | 0 | 1 | 0 | 1 | 0 | 1 | 1 | 4 | 0 | 4 | 4 |
| 240 | T7507 | 1 | 1 | 1 | 1 | 1 | 4 | 1 | 1 | 1 | 1 | 0 | 1 | 1 | 4 | 1 | 4 | 4 |
| 343 | OLGA | 1 | 0 | 1 | 1 | 1 | 4 | 1 | 2 | 0 | 1 | 1 | 1 | 1 | 4 | 1 | 4 | 4 |
| 423 | SAVC | 1 | 0 | 1 | 1 | 0 | 4 | 0 | 2 | 0 | 1 | 0 | 1 | 1 | 4 | 0 | 4 | 4 |
| 712 | JBUSH | 1 | 0 | 1 | 1 | 0 | 4 | 0 | 2 | 0 | 1 | 0 | 1 | 1 | 4 | 0 | 4 | 4 |
| 723 | BM16 | 1 | 0 | 1 | 1 | 0 | 4 | 0 | 2 | 0 | 1 | 0 | 1 | 1 | 4 | 0 | 4 | 4 |
| 773 | LBUF | 1 | 1 | 2 | 1 | 3 | 4 | 3 | 1 | 3 | 1 | 3 | 1 | 1 | 4 | 3 | 4 | 4 |
| 931 | AMALA | 1 | 1 | 1 | 1 | 1 | 4 | 1 | 1 | 0 | 1 | 1 | 1 | 1 | 4 | 1 | 4 | 4 |
| 1042 | BM90 | 1 | 1 | 1 | 1 | 1 | 4 | 1 | 1 | 1 | 1 | 1 | 1 | 1 | 4 | 1 | 4 | 4 |
| 1102 | TAB089 | 1 | 0 | 1 | 1 | 0 | 4 | 0 | 2 | 0 | 1 | 0 | 1 | 1 | 4 | 0 | 4 | 4 |
| 122 | KAS116 | 1 | 0 | 1 | 1 | 0 | 4 | 0 | 2 | 0 | 1 | 0 | 1 | 1 | 4 | 0 | 4 | 4 |

KIR genotyped Cell lines by the $10^{th}$ IHW. results of probes set1.
0 = negative by MLPA and 10th IHW
1 = positive by MPLA and 10th IHW
2 = positive by MLPA and negative by 10th IHW
3 = negative by MLPA and positive by 10th IHW
4 = not typed by 10th IHW but positve by MLPA ▒ negative by two laboratories and positive typed by one

TABLE 12

Verification of KIR MLPA probe set 1 on 5 PCR-SSP KIR typed samples.

| sample | 2DL1 | 2DL2 | 2DL3 | 2DL4 | 2DL5 | 2DL5A | 2DS1 | 2DS2 | 2DS3 | 2DS4 | 2DS5 | 3DL1 | 3DL2 | 3DL3 | 3DS1 | 2DP1 | 3DP1 |
|---|---|---|---|---|---|---|---|---|---|---|---|---|---|---|---|---|---|
| 33_7536 | 1 | 0 | 1 | 1 | 1 | 3 | 1 | 2 | 1 | 1 | 1 | 1 | 1 | 1 | 1 | 1 | 1 |
| 33_8025 | 1 | 1 | 1 | 1 | 0 | 3 | 0 | 2 | 0 | 1 | 0 | 1 | 1 | 1 | 0 | 1 | 1 |
| 33_8037 | 1 | 0 | 1 | 1 | 1 | 3 | 1 | 2 | 0 | 1 | 1 | 1 | 1 | 1 | 1 | 1 | 1 |
| 33_8588 | 0 | 1 | 0 | 1 | 0 | 3 | 0 | 1 | 0 | 1 | 0 | 1 | 1 | 1 | 0 | 0 | 1 |
| 33_9097 | 1 | 1 | 0 | 1 | 1 | 3 | 1 | 1 | 1 | 0 | 1 | 0 | 1 | 1 | 1 | 1 | 1 |

PCR-SSP KIR typed DMA. results of probe set 1.
0 = negative by MLPA and SSP
1 = positive by MPLA and SSP
2 = positvie by MLPA and negative by SSP
3 = positive by MLPA not typed by SSP

TABLE 13

Verification of KIR MLPA probe set 2 on 11 cell lines KIR-genotyped by the 10th IHW.

| CODE | NAME | 2DL1 | 2DL2 | 2DL3 | 2DL4 | 2DL5 | 2DL5A | 2DS1 | 2DS2 | 2DS3 | 2DS4 | 2DS5 | 3DL1 | 3DL2 | 3DL3 | 3DS1 | 2DP1 | 3DP1 |
|---|---|---|---|---|---|---|---|---|---|---|---|---|---|---|---|---|---|---|
| 231 | JVM | 1 | 1 | 1 | 1 | 0 | 4 | 0 | 1 | 0 | 1 | 2 | 1 | 1 | 4 | 2 | 4 | 4 |
| 240 | T7507 | 1 | 1 | 1 | 1 | 1 | 4 | 1 | 1 | 1 | 1 | 2 | 1 | 1 | 4 | 1 | 4 | 4 |
| 343 | OLGA | 1 | 0 | 1 | 1 | 1 | 4 | 1 | 0 | 0 | 1 | 2 | 1 | 1 | 4 | 1 | 4 | 4 |
| 423 | SAVC | 1 | 0 | 1 | 1 | 0 | 4 | 0 | 0 | 0 | 1 | 2 | 1 | 1 | 4 | 2 | 4 | 4 |
| 712 | JBUSH | 1 | 0 | 1 | 1 | 0 | 4 | 0 | 0 | 0 | 1 | 2 | 1 | 1 | 4 | 2 | 4 | 4 |
| 723 | BM16 | 1 | 0 | 1 | 1 | 0 | 4 | 2 | 0 | 0 | 1 | 2 | 1 | 1 | 4 | 2 | 4 | 4 |
| 773 | LBUF | 1 | 1 | 2 | 1 | 3 | 4 | 1 | 1 | 3 | 1 | 1 | 1 | 1 | 4 | 1 | 4 | 4 |
| 931 | AMALA | 1 | 1 | 1 | 1 | 1 | 4 | 1 | 1 | 0 | 1 | 1 | 1 | 1 | 4 | 1 | 4 | 4 |
| 1042 | BM90 | 1 | 1 | 1 | 1 | 1 | 4 | 1 | 1 | 1 | 1 | 1 | 1 | 1 | 4 | 1 | 4 | 4 |
| 1102 | TAB089 | 1 | 0 | 1 | 1 | 0 | 4 | 2 | 0 | 0 | 1 | 2 | 1 | 1 | 4 | 2 | 4 | 4 |
| 122 | KAS116 | 1 | 0 | 1 | 1 | 0 | 4 | 2 | 0 | 0 | 1 | 2 | 1 | 1 | 4 | 2 | 4 | 4 |

KIR genotyped Cell lines by the 10th IHW. results of probe set2.
0 = negative by MLPA and 10th IHW
1 = positive by MPLA and 10th IHW
2 = positive by MLPA and negative by 10th IHW
3 = negative by MLPA and positive by 10th IHW
4 = not typed by 10th IHW but positve by MLPA
▒ negative by two laboratories and positive typed by one

TABLE 14

Verification of KIR MLPA probe set 21 on 5 PCR-SSP KIR typed samples.

| sample | 2DL1 | 2DL2 | 2DL3 | 2DL4 | 2DL5 | 2DL5A | 2DS1 | 2DS2 | 2DS3 | 2DS4 | 2DS5 | 3DL1 | 3DL2 | 3DL3 | 3DS1 | 2DP1 | 3DP1 |
|---|---|---|---|---|---|---|---|---|---|---|---|---|---|---|---|---|---|
| 33_7536 | 1 | 0 | 1 | 1 | 1 | 4 | 1 | 0 | 1 | 1 | 1 | 1 | 1 | 1 | 1 | 1 | 1 |
| 33_8025 | 1 | 0 | 1 | 1 | 0 | 4 | 0 | 0 | 0 | 1 | 2 | 1 | 1 | 1 | 2 | 1 | 1 |
| 33_8037 | 1 | 0 | 1 | 1 | 1 | 4 | 1 | 0 | 0 | 1 | 1 | 1 | 1 | 1 | 1 | 1 | 1 |
| 33_8588 | 2 | 1 | 0 | 1 | 0 | 4 | 0 | 1 | 0 | 1 | 2 | 1 | 1 | 1 | 2 | 0 | 3 |
| 33_9097 | 1 | 1 | 0 | 1 | 1 | 4 | 1 | 1 | 1 | 0 | 1 | 2 | 1 | 1 | 1 | 1 | 1 |

PCR-SSP KIR typed patients, results of probe set 2.
0 = negative by MLPA and SSP
1 = positive by MPLA and SSP
2 = positive by MLPA and negative by SSP
3 = negative by MLPA and positive by SSP
4 = positive by MLPA not typed by SSP

REFERENCES

Brown M A. Genetics and the pathogenesis of ankylosing spondylitis. *Curr Opin Rheumatol.* 2009; 21:318-23.

Carrignton M, Noramn P. "The KIR gene cluster" National Center for Biotechnology Information (US); Bookself ID: NBK10135; May 28, 2003.

Chan A T, Kollnberger S D, Wedderburn L R, Bowness P. Expansion and enhanced survival of natural killer cells expressing the killer immunoglobulin-like receptor KIR3DL2 in spondylarthritis. *Arthritis Rheum.* 2005; 52:3586-95.

Cook M A, Norman P J, Curran M D, Maxwell L D, Briggs D C, Middleton D, Vaughan R W. A multi-laboratory characterization of the KIR genotypes of the 10th International Histocompatibility Workshop cell lines. *Human Immunology* 2003: 64, 567-571

Crum K A, Logue S. E, Curran M D, Middleton D. Development of a PCR-SSOP approach capable of defining the natural killer cell inhibitory receptor (KIR) gene sequence repertoire. *Tissue Antigens* 2000: 56: 313-326.

Du Z, Gjertson D W, Reed E F, Rajalingam R. Receptor-ligand analyses define minimal killer cell Ig-like receptor (KIR) in humans. *Immunogenetics* 2007:59:1-15

Gomez-Lozano N, Gardiner C M, Parham P, Vilches C. Some human KIR haplotypes contain two KIR2DL5 genes: KIR2DL5A and KIR2DL5B. *Immunogenetics* 2002: 54 (5): 314-9

Gómez-Lozano N, Estefania E, Williams F, Halfpenny I, Middleton D, Solís R, Vilches C. The silent KIR3DP1 gene (CD158c) is transcribed and might encode a secreted receptor in a minority of humans, in whom the KIR3DP1, KIR2DL4 and KIR3DL1/KIR3DS1 genes are duplicated. *European Journal Immunology* 2005: 35(1):16-24

Hollenbach J A, Ladner M B, Saeteurn K, Taylor K D, Mei L, Haritunians T, McGovern D P B, Erlich H A, Rotter J I, Trachtenberg E A. Susceptibility to Crohn's disease is mediated by KIR2DL2/KIR2DL3 heterozygosity and the HLA-C ligand. *Immunogenetics* 2009: 61(10): 663-671

Hsu K C, Liu X R, Selvakumar A, Mickelson E, O'Reilly R J, Dupont B. Killer Ig-like receptor haplotype analysis by gene content: evidence for genomic diversity with a minimum of six basic framework haplotypes, each with multiple subsets. *Journal of Immunology* 2002: 1; 169(9):5118-29

Hsu K C, Chida S, Geraghty D E, Dupont B. The killer cell immunoglobulin-like receptor (KIR) genomic region: gene-order, haplotypes and allelic polymorphism. *Immunol Rev.* 2002 December; 190:40-52.

Khakoo S I, Thio C L, Martin M P, Brooks C R, Gao X, Astemborski J, et al. HLA and NK cell inhibitory receptor genes in resolving hepatitis C virus infection. *Science* 2004; 305: 872-4.

Li H, Pascal V, Martin M P, Carrington M, Anderson S K. Genetic control of variegated KIR gene expression: polymorphisms of the bi-directional KIR3DL1 promoter are associated with distinct frequencies of gene expression. *PLoS Genet.* 2008 November; 4(11):e1000254.

Majorczyk E, Pawlik A, □uszczek W, Nowak I, Wi□niewski A, Jasek M, Ku□nierczyk P. Associations of killer cell immunoglobulin-like receptor genes with complications of rheumatoid arthritis. *Genes Immun.* 2007; 8:678-83.

Marsh S, Parham P, Dupont B, Geraghty D, Trowsdale J, Middelton D, Vilches C, Carrington M, Witt C, Guethlein L, Shilling H, Garcia C, Hsu K, Wain H. Killer-cell Immunoglobulin-like Receptor (KIR) Nomenclature Report. *Human Immunology* 2002: 64, 648-654.

Martin M P, Qi Y, Gao X, Yamada E, Martin J N, Pereyra F, et al. Innate partnership of HLA-B and KIR3DL1 subtypes against HIV-1. *Nat Genet* 2007; 39:733-40.

Middleton D, Williams F, Halfpenny I A. KIR genes. *Transplant Immunology* 2005: 14(3-4):135-42

Parham P, McQueen K L. Alloreactive killer cells: hindrance and help for haematopoietic transplants. *Nature reviews Immunology* 3 2003: doi: 10.1038/nri999

Shilling H G, Guethlein L A, Cheng N W, Gardiner C M, Rodriguez R, Tyan D, Parham P. Allelic polymorphism synergizes with variable gene content to individualize human KIR genotype. *Journal of Immunology* 2002: 1:168(5):2307-15

Schouten J P, McElgunn C J, Waaijer R, Zwijnenburg D, Diepvens F, Pals G. Relative quantification of 40 nucleic acid sequences by multiplex ligation-dependent probe amplification. *Nucleic Acid Research.* 2002: 15:30(12):e57

Sun J Y, Gaidulis L, Miller M M, Goto R M, Rodriguez R, Forman S J, Senitzer D. Development of a multiplex PCR-SSP method for Killer-cell immunoglobulin-like receptor genotyping. *Tissue Antigens* 2004: 64: 462-468.

Trowsdale J, Barten R, Haude A, Stewart C A, Beck S, Wilson M J. The genomic context of natural killer receptor extended gene families. 2001. *Immunological Reviews* volume 181: 20-38

Urhberg M, Valiante N M, Shum B P, Shilling H G, Lienert-Weidenbach K, Corliss B, Tyan D, Lanier L L, Parham P. *Immunity* volume 1997: 7, 753-763

Uhrberg M. The KIR gene family: life in the fast lane of evolution. *European Journal of Immunology* 2005: 35:10-15

Vilches C, Parham P. KIR: diverse, rapidly evolving receptors of innate and adaptive immunity. *Annual Reviews Immunology* 2002: 20:217-51

Vilches C, Castano J, Gomez-Lozano N, Estefania E. facilitation of KIR genotyping by a PCR-SSP method that amplifies short DNA fragments. 2007. *Tissue Antigens* 70, 415-422.

Williams F, Maxwell L D, Halfpenny I A, Meenagh A, Sleator C, Curran M D, Middleton D. Multiple copies of KIR 3DL/S1 and KIR 2DL4 genes identified in a number of individuals. *Human Immunology* 2003: 64, 729-732.

Yen J H, Moore B E, Nakajima T, Scholl D, Schaid D J, Weyand C M, Goronzy J J. Major histocompatibility complex class I-recognizing receptors are disease risk genes in rheumatoid arthritis. *J Exp Med.* 2001; 193:1159-67.

Zhang Y, Wang B, Shihui Y, Liu S, Liu M, Shen C, Teng Y, Qi J. Killer cell immunoglobulin-like receptor gene polymorphisms in patients with leukemia: Possible association with susceptibility to the disease. Leuk Res, 34(1):55-8, 2010, doi10.1016/j.leukres.2009.04.022 (Epub. Date, May 18, 2009).

The invention claimed is:

1. A method for determining whether at least one target nucleic acid sequence is present in a sample, wherein said at least one target nucleic acid sequence comprises a first region, a second region and a third region, comprising the steps of:
   a) adding to said sample different probe sets and forming a mixture, each probe set of said different probe sets comprising:
      a first nucleic acid probe, said first probe comprising
         a first nucleic acid sequence which is complementary to said first region of its target nucleic acid sequence of said at least one target nucleic acid sequence and a non-complementary nucleic acid sequence located 5' of the first nucleic acid sequence comprises a first primer binding site, and
      a second nucleic acid probe, said second probe comprising
         a second nucleic acid sequence which is complementary to said second region of its target nucleic acid sequence of said at least one target nucleic acid sequence and a non-complementary nucleic acid sequence located 3' of the second nucleic acid sequence comprises a second primer binding site,
   wherein at least one probe set of said different probe sets comprises a third nucleic acid probe, said third probe comprising a third nucleic acid sequence complementary to said third region of said its target nucleic acid sequence of said at least one target nucleic acid sequence, and
   wherein said first region and said third region of said at least one target nucleic acid sequence are located essentially adjacent to each other and said third region and said second region of said at least one target nucleic acid sequence are located essentially adjacent to each other,
b) allowing hybridization of said different probe sets to their complementary nucleic acids of said sample,
c) after step b), subjecting nucleic acids of said different probe sets to a ligation reaction,
d) after step c), subjecting said mixture to a nucleic acid amplification reaction, using at least one primer capable of specifically binding said first primer binding site and at least one primer capable of specifically binding said second primer binding site, and
e) determining whether an amplified nucleic acid is present after step d), thereby determining whether said at least one target nucleic acid sequence is present in said sample,
wherein said third region comprises a gene variant-specific nucleotide and/or a pseudogene variant-specific nucleotide and/or a gene variant-specific sequence and/or a pseudogene variant-specific sequence and/or a polymorphism within a given gene or pseudogene, and either said first region or said second region located essentially adjacent to said third region comprises a gene variant-specific nucleotide and/or a pseudogene variant-specific nucleotide and/or a gene variant-specific sequence and/or a pseudogene variant-specific sequence and/or a polymorphism within said given gene or pseudogene.

2. The method according to claim 1, wherein said different probe sets comprise at least two, or at least five, or at least ten of said different probe sets, each of said different probe sets comprises said third nucleic acid probe.

3. The method according to claim 2, wherein at least 50%, or at least 70%, or at least 80%, or at least 90% of said third nucleic acid probe is complementary to said third region of said its target nucleic acid sequence of said at least one target nucleic acid sequence.

4. The method according to claim 3, wherein at least 50%, or at least 70%, or at least 80%, or at least 90% of said third nucleic acid probe is combined with the first nucleic acid probe or the second nucleic acid probe that is complementary to said first or said second region of said its target nucleic acid sequence of said at least one target nucleic acid sequence comprising at least one gene variant or pseudogene variant.

5. The method according to claim 1, wherein the difference in length of said non-complementary nucleic acid sequences of said first nucleic acid probe of each of said different probe sets and/or the difference in length of said non-complementary nucleic acid sequences of said second nucleic acid probe of each of said different probe sets is less than 6 nucleotides.

6. The method according to claim 5, wherein said less than 6 nucleotides is less than 4 nucleotides.

7. The method according to claim 1, wherein said at least one target nucleic acid sequence is present in a killer immunoglobulin-like receptor (KIR) locus, said KIR locus comprising multiple KIR genes and/or KIR pseudogenes.

8. The method according to claim 7, wherein relative copy number variation of at least one KIR gene of said multiple KIR genes and/or copy number variation of at least one KIR pseudogene of said multiple KIR pseudogenes is determined by analyzing the amount of said amplified nucleic acid.

9. The method according to claim 1, wherein at least one probe of said different probe sets has at least 70% sequence identity to a probe of FIG. 3A, 3B, 3C or 3D.

10. The method according to claim 9, wherein said at least one probe, which has at least 70% sequence identity to a probe of FIG. 3C or 3D, is used in the method.

11. The method according to claim 1, wherein said different probe sets have at least 70% sequence identity to at least two probe sets of FIG. 3A, 3B, 3C or 3D.

12. The method according to claim 11, wherein said at least two probe sets are at least two probe sets of FIG. 3C or 3D.

13. The method according to claim 1, wherein said polymorphism comprises a single nucleotide polymorphism (SNP).

* * * * *

UNITED STATES PATENT AND TRADEMARK OFFICE
CERTIFICATE OF CORRECTION

| | | |
|---|---|---|
| PATENT NO. | : 9,017,971 B2 | Page 1 of 1 |
| APPLICATION NO. | : 12/998595 | |
| DATED | : April 28, 2015 | |
| INVENTOR(S) | : Taco Willem Kuijpers et al. | |

It is certified that error appears in the above-identified patent and that said Letters Patent is hereby corrected as shown below:

On the title page, item (30) should read

-- (30)     Foreign Application Priority Data

Nov. 5, 2008 (NL)          PCT/NL2008/050698 --

Signed and Sealed this
Twentieth Day of October, 2015

Michelle K. Lee
*Director of the United States Patent and Trademark Office*

```
                        SEQUENCE LISTING

<160> NUMBER OF SEQ ID NOS: 163

<210> SEQ ID NO 1
<211> LENGTH: 19
<212> TYPE: DNA
<213> ORGANISM: Artificial
<220> FEATURE:
<223> OTHER INFORMATION: primer

<400> SEQUENCE: 1 gggttccta agggttgga                                                  19

<210> SEQ ID NO 2
<211> LENGTH: 23
<212> TYPE: DNA
<213> ORGANISM: Artificial
<220> FEATURE:
<223> OTHER INFORMATION: primer

<400> SEQUENCE: 2
tctagattgg atcttgctgg cac                                            23

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3 gggttccta agggttgg                                                   18
```

<210> SEQ ID NO 4
<211> LENGTH: 39
<212> TYPE: DNA
<213> ORGANISM: Artificial
<220> FEATURE:
<223> OTHER INFORMATION: KIR3DL1 WT Left probe part

<400> SEQUENCE: 4
ggttccctaa gggttggacc cctcacgcct cgttggaca                   39

<210> SEQ ID NO 5
<211> LENGTH: 45
<212> TYPE: DNA
<213> ORGANISM: Artificial
<220> FEATURE:
<223> OTHER INFORMATION: KIR3DL1*024N Left probe part

<400> SEQUENCE: 5
gggttcccta agggttggac aaggacccct cacgcctcgt tggac            45

<210> SEQ ID NO 6
<211> LENGTH: 51
<212> TYPE: DNA
<213> ORGANISM: Artificial
<220> FEATURE:
<223> OTHER INFORMATION: KIR3DL1 Middle probe part

<400> SEQUENCE: 6
gatccatgat ggggtctcca aggccaattt ctccatcggt cccatgatgc t      51

<210> SEQ ID NO 7
<211> LENGTH: 58
<212> TYPE: DNA
<213> ORGANISM: Artificial
<220> FEATURE:
<223> OTHER INFORMATION: KIR3DL1 Right probe part

<400> SEQUENCE: 7
gcccttgcag ggacctacag atgctacggt tctggtctag attggatctt gctggcac  58

<210> SEQ ID NO 8
<211> LENGTH: 24
<212> TYPE: DNA
<213> ORGANISM: Artificial
<220> FEATURE:
<223> OTHER INFORMATION: probe KIR2DS5

<400> SEQUENCE: 8
cgcatgacac aagacctggc aggg                                   24

<210> SEQ ID NO 9
<211> LENGTH: 24
<212> TYPE: DNA
<213> ORGANISM: Artificial
<220> FEATURE:
<223> OTHER INFORMATION: probe KIR2DS3

<400> SEQUENCE: 9
cgcatgaggc aagacctggc aggg                                   24

<210> SEQ ID NO 10
<211> LENGTH: 24
<212> TYPE: DNA
<213> ORGANISM: Artificial
<220> FEATURE:
<223> OTHER INFORMATION: probe KIR2DP1

-continued

```
<400> SEQUENCE: 10
cccatgatgg aagacctggc aggg                                          24

<210> SEQ ID NO 11
<211> LENGTH: 24
<212> TYPE: DNA
<213> ORGANISM: Artificial
<220> FEATURE:
<223> OTHER INFORMATION: probe KIR2DL1

<400> SEQUENCE: 11
cgcatgacgc aagacctggc aggg                                          24

<210> SEQ ID NO 12
<211> LENGTH: 24
<212> TYPE: DNA
<213> ORGANISM: Artificial
<220> FEATURE:
<223> OTHER INFORMATION: probe KIR2DS1

<400> SEQUENCE: 12
cgcatgaagc aagacctggc aggg                                          24

<210> SEQ ID NO 13
<211> LENGTH: 24
<212> TYPE: DNA
<213> ORGANISM: Artificial
<220> FEATURE:
<223> OTHER INFORMATION: probe KIR2DS4

<400> SEQUENCE: 13
cccatgatgc ctgtccttgc agga                                          24

<210> SEQ ID NO 14
<211> LENGTH: 24
<212> TYPE: DNA
<213> ORGANISM: Artificial
<220> FEATURE:
<223> OTHER INFORMATION: probe KIR3DS1

<400> SEQUENCE: 14
tccatgatgc gtgcccttgc aggg                                          24

<210> SEQ ID NO 15
<211> LENGTH: 24
<212> TYPE: DNA
<213> ORGANISM: Artificial
<220> FEATURE:
<223> OTHER INFORMATION: probe KIR2DL3

<400> SEQUENCE: 15
cccatgatgc aagaccttgc aggg                                          24

<210> SEQ ID NO 16
<211> LENGTH: 24
<212> TYPE: DNA
<213> ORGANISM: Artificial
<220> FEATURE:
<223> OTHER INFORMATION: probe KIR3DP1

<400> SEQUENCE: 16
cgcatgacgc aagaccttgc aggg                                          24

<210> SEQ ID NO 17
```

<211> LENGTH: 24
<212> TYPE: DNA
<213> ORGANISM: Artificial
<220> FEATURE:
<223> OTHER INFORMATION: probe KIR3DL2

<400> SEQUENCE: 17
cccttgatgc ctgtccttgc agga                                         24

<210> SEQ ID NO 18
<211> LENGTH: 24
<212> TYPE: DNA
<213> ORGANISM: Artificial
<220> FEATURE:
<223> OTHER INFORMATION: probe KIR3DL3

<400> SEQUENCE: 18
cccatgacac ctgcccttgc aggg                                         24

<210> SEQ ID NO 19
<211> LENGTH: 48
<212> TYPE: DNA
<213> ORGANISM: Artificial
<220> FEATURE:
<223> OTHER INFORMATION: probe

<400> SEQUENCE: 19
gggttcccta agggttggac tgaccttggg ccctgcagag aacctaca               48

<210> SEQ ID NO 20
<211> LENGTH: 48
<212> TYPE: DNA
<213> ORGANISM: Artificial
<220> FEATURE:
<223> OTHER INFORMATION: probe

<400> SEQUENCE: 20
ttcatgggcc tccccctccc tggatgtcta gattgatctt gctggcac               48

<210> SEQ ID NO 21
<211> LENGTH: 50
<212> TYPE: DNA
<213> ORGANISM: Artificial
<220> FEATURE:
<223> OTHER INFORMATION: probe

<400> SEQUENCE: 21
gggttcccta agggttggat agatgcttcg gctctttccg tgccctgccc             50

<210> SEQ ID NO 22
<211> LENGTH: 50
<212> TYPE: DNA
<213> ORGANISM: Artificial
<220> FEATURE:
<223> OTHER INFORMATION: probe

<400> SEQUENCE: 22
cacgcgtggt cagacccgag tgacccgtct agattggatc ttgctggcac             50

<210> SEQ ID NO 23
<211> LENGTH: 54
<212> TYPE: DNA
<213> ORGANISM: Artificial
<220> FEATURE:
<223> OTHER INFORMATION: probe

<400> SEQUENCE: 23

```
gggttccota agggttggac catcacgatg tccagagggt cactgggagc tgaa        54
```

<210> SEQ ID NO 24
<211> LENGTH: 54
<212> TYPE: DNA
<213> ORGANISM: Artificial
<220> FEATURE:
<223> OTHER INFORMATION: probe

<400> SEQUENCE: 24

```
aactgatagg gggagtgagg aacagagacc gtctagattg gatcttgctg gcac        54
```

<210> SEQ ID NO 25
<211> LENGTH: 55
<212> TYPE: DNA
<213> ORGANISM: Artificial
<220> FEATURE:
<223> OTHER INFORMATION: probe

<400> SEQUENCE: 25

```
gggttccota agggttggaa tccaccctaa ggtttgggga aggactcacc catga       55
```

<210> SEQ ID NO 26
<211> LENGTH: 56
<212> TYPE: DNA
<213> ORGANISM: Artificial
<220> FEATURE:
<223> OTHER INFORMATION: probe

<400> SEQUENCE: 26

```
gtggccaggc ccctgcagc aagaagaacc ctgtctagat tggatcttgc tggcgc       56
```

<210> SEQ ID NO 27
<211> LENGTH: 65
<212> TYPE: DNA
<213> ORGANISM: Artificial
<220> FEATURE:
<223> OTHER INFORMATION: probe

<400> SEQUENCE: 27

```
gggttccota agggttggac ccaaggtggt caggacaagc ccttgctgtc tgcctggccc  60
agctc                                                             65
```

<210> SEQ ID NO 28
<211> LENGTH: 56
<212> TYPE: DNA
<213> ORGANISM: Artificial
<220> FEATURE:
<223> OTHER INFORMATION: probe

<400> SEQUENCE: 28

```
tgtggtgcct ccaggacatg tgattcttcg gtgtctagat tggatcttgc tggcgc      56
```

<210> SEQ ID NO 29
<211> LENGTH: 66
<212> TYPE: DNA
<213> ORGANISM: Artificial
<220> FEATURE:
<223> OTHER INFORMATION: probe

<400> SEQUENCE: 29

```
gggttccota agggttggac accatgatca ccaggggggtt gctgggtgct gaccacccag 60
tgagga                                                            66
```

<210> SEQ ID NO 30
<211> LENGTH: 59
<212> TYPE: DNA
<213> ORGANISM: Artificial
<220> FEATURE:
<223> OTHER INFORMATION: probe

<400> SEQUENCE: 30
agtgtgggtg tgaaccccga catctgtagg tccctgtcta gattggatct tgctggcgc    59

<210> SEQ ID NO 31
<211> LENGTH: 61
<212> TYPE: DNA
<213> ORGANISM: Artificial
<220> FEATURE:
<223> OTHER INFORMATION: probe

<400> SEQUENCE: 31
gggttcccta agggttggac tcccctctct gtgcagaagg aagtgctcaa acatgacatc    60
c                                                                   61

<210> SEQ ID NO 32
<211> LENGTH: 76
<212> TYPE: DNA
<213> ORGANISM: Artificial
<220> FEATURE:
<223> OTHER INFORMATION: probe

<400> SEQUENCE: 32
gaccaacatt gcaggatgac tgtctcttct gatttcacca ggtgacctgg gagtctagat    60
tggatcttgc tggcac                                                   76

<210> SEQ ID NO 33
<211> LENGTH: 57
<212> TYPE: DNA
<213> ORGANISM: Artificial
<220> FEATURE:
<223> OTHER INFORMATION: probe

<400> SEQUENCE: 33
gggttcccta agggttggac tcaggtgtga ggggagctgt gacaaggaag aacctcc       57

<210> SEQ ID NO 34
<211> LENGTH: 32
<212> TYPE: DNA
<213> ORGANISM: Artificial
<220> FEATURE:
<223> OTHER INFORMATION: probe

<400> SEQUENCE: 34
ctgaggaaac tgcctcttct tccaggtcta tt                                  32

<210> SEQ ID NO 35
<211> LENGTH: 53
<212> TYPE: DNA
<213> ORGANISM: Artificial
<220> FEATURE:
<223> OTHER INFORMATION: probe

<400> SEQUENCE: 35
tgggaaacct tcactctcag cccagccggg tctagattgg atcttgctgg cgc           53

<210> SEQ ID NO 36
<211> LENGTH: 74

```
<212> TYPE: DNA
<213> ORGANISM: Artificial
<220> FEATURE:
<223> OTHER INFORMATION: probe

<400> SEQUENCE: 36
gggttcccta agggttggac gtgttcttat ctaggatact ccaaggccaa tttctccatc    60
ggtcccatga tgct                                                     74

<210> SEQ ID NO 37
<211> LENGTH: 75
<212> TYPE: DNA
<213> ORGANISM: Artificial
<220> FEATURE:
<223> OTHER INFORMATION: probe

<400> SEQUENCE: 37
tgcccttgca gggacctaca gatgctacgg ttctgttctc tcgtcagacg tgtctagatt    60
ggatcttgct ggcac                                                    75

<210> SEQ ID NO 38
<211> LENGTH: 69
<212> TYPE: DNA
<213> ORGANISM: Artificial
<220> FEATURE:
<223> OTHER INFORMATION: probe

<400> SEQUENCE: 38
gggttcccta agggttggac ggggcgcggc tgcctgtctg caccggcagc accatgtcgc    60
tcatggtca                                                           69

<210> SEQ ID NO 39
<211> LENGTH: 32
<212> TYPE: DNA
<213> ORGANISM: Artificial
<220> FEATURE:
<223> OTHER INFORMATION: probe

<400> SEQUENCE: 39
tcagcatggc gtgtgttggt gagtcctgga aa                                 32

<210> SEQ ID NO 40
<211> LENGTH: 67
<212> TYPE: DNA
<213> ORGANISM: Artificial
<220> FEATURE:
<223> OTHER INFORMATION: probe

<400> SEQUENCE: 40
tgaccatgag cgacatggtg ctgccggtgc agacgggagg ttggtctaga ttggatcttg    60
ctggcac                                                             67

<210> SEQ ID NO 41
<211> LENGTH: 59
<212> TYPE: DNA
<213> ORGANISM: Artificial
<220> FEATURE:
<223> OTHER INFORMATION: probe

<400> SEQUENCE: 41
gggttcccta agggttggac ctgcttcaga acatggctct ctgctgggga gacacccaa    59

<210> SEQ ID NO 42
```

```
<211> LENGTH: 54
<212> TYPE: DNA
<213> ORGANISM: Artificial
<220> FEATURE:
<223> OTHER INFORMATION: probe

<400> SEQUENCE: 42
tctgcaggcc catagtgtaa ccctggtgct ccttcccttc caggactcac caag         54

<210> SEQ ID NO 43
<211> LENGTH: 57
<212> TYPE: DNA
<213> ORGANISM: Artificial
<220> FEATURE:
<223> OTHER INFORMATION: probe

<400> SEQUENCE: 43
acatgccagg atgatgaccg tgggtgacat ggagtctaga ttggatcttg ctggcac      57

<210> SEQ ID NO 44
<211> LENGTH: 67
<212> TYPE: DNA
<213> ORGANISM: Artificial
<220> FEATURE:
<223> OTHER INFORMATION: probe

<400> SEQUENCE: 44
gggttcccta agggttggac cgagtaaacc ggaaaatttt catctgcaca gagagggac    60 gtttaac                                                              67

<210> SEQ ID NO 45
<211> LENGTH: 47
<212> TYPE: DNA
<213> ORGANISM: Artificial
<220> FEATURE:
<223> OTHER INFORMATION: probe

<400> SEQUENCE: 45
cacactttgc gcctcattgg agagcacatt gatggggtct ccaaggg                  47

<210> SEQ ID NO 46
<211> LENGTH: 71
<212> TYPE: DNA
<213> ORGANISM: Artificial
<220> FEATURE:
<223> OTHER INFORMATION: probe

<400> SEQUENCE: 46
caacttctcc atcggtcgca tgacacaaga cctggcatag cgaatacgtc tagattggat    60
cttgctggca c                                                         71

<210> SEQ ID NO 47
<211> LENGTH: 72
<212> TYPE: DNA
<213> ORGANISM: Artificial
<220> FEATURE:
<223> OTHER INFORMATION: probe

<400> SEQUENCE: 47
gggttcccta agggttggac taccccatcg ctcttcatgc tggatcattc actctgcatc    60
ccaatgacaa tg                                                        72

<210> SEQ ID NO 48
<211> LENGTH: 64
```

```
<212> TYPE: DNA
<213> ORGANISM: Artificial
<220> FEATURE:
<223> OTHER INFORMATION: probe

<400> SEQUENCE: 48
agaagaaagt ctggacactc tcacctatga tcacgatgtc cagagggtca ctgggagctg    60
acac                                                                64

<210> SEQ ID NO 49
<211> LENGTH: 53
<212> TYPE: DNA
<213> ORGANISM: Artificial
<220> FEATURE:
<223> OTHER INFORMATION: probe

<400> SEQUENCE: 49
ctgatagggg gagtgagtaa cagaaccgta gtctagattg atcttgctgg cac           53

<210> SEQ ID NO 50
<211> LENGTH: 78
<212> TYPE: DNA
<213> ORGANISM: Artificial
<220> FEATURE:
<223> OTHER INFORMATION: probe

<400> SEQUENCE: 50 gggttccctaa agggttggac acagggccca tgaaaaggct gttccagaat attatgttgt   60
agagctcagg gacaggca                                                 78

<210> SEQ ID NO 51
<211> LENGTH: 67
<212> TYPE: DNA
<213> ORGANISM: Artificial
<220> FEATURE:
<223> OTHER INFORMATION: probe

<400> SEQUENCE: 51
ccccatcttc cttttacaga ctgaagttgt taaacccaag ataagaatga cactgaagaa    60
tcacata                                                             67

<210> SEQ ID NO 52
<211> LENGTH: 50
<212> TYPE: DNA
<213> ORGANISM: Artificial
<220> FEATURE:
<223> OTHER INFORMATION: probe

<400> SEQUENCE: 52
tcctggaggc accacagggc ttggccagtc tagattgatc ttgctggcgc               50

<210> SEQ ID NO 53
<211> LENGTH: 70
<212> TYPE: DNA
<213> ORGANISM: Artificial
<220> FEATURE:
<223> OTHER INFORMATION: probe

<400> SEQUENCE: 53 gggttccctaa agggttggac tgcacagttg gatcactgcg ttttcacaca gagaaaaatc   60
actcgccctt                                                          70

<210> SEQ ID NO 54
```

```
<211> LENGTH: 66
<212> TYPE: DNA
<213> ORGANISM: Artificial
<220> FEATURE:
<223> OTHER INFORMATION: probe

<400> SEQUENCE: 54
ctcagaggcc caagacaccc ccaacagata tcatcgtgta cacggaactt ccaaatgctg    60
agccct                                                              66

<210> SEQ ID NO 55
<211> LENGTH: 67
<212> TYPE: DNA
<213> ORGANISM: Artificial
<220> FEATURE:
<223> OTHER INFORMATION: probe

<400> SEQUENCE: 55
gatccaaagt tgtctcctgc ccatgagcac cacagtcagg ccttgtctag attgatcttg    60
ctggcgc                                                             67

<210> SEQ ID NO 56
<211> LENGTH: 81
<212> TYPE: DNA
<213> ORGANISM: Artificial
<220> FEATURE:
<223> OTHER INFORMATION: probe

<400> SEQUENCE: 56
gggttcccta agggttggac ttgttcatca gaatcctgga gagagggaaa tgctgagtga    60
gggagggtgc tcacattttt c                                             81

<210> SEQ ID NO 57
<211> LENGTH: 64
<212> TYPE: DNA
<213> ORGANISM: Artificial
<220> FEATURE:
<223> OTHER INFORMATION: probe

<400> SEQUENCE: 57
aggactcttt gggaataaca ctagccacga ggctgggccg aggagcacct acctcgctgt    60
tcac                                                                64

<210> SEQ ID NO 58
<211> LENGTH: 74
<212> TYPE: DNA
<213> ORGANISM: Artificial
<220> FEATURE:
<223> OTHER INFORMATION: probe

<400> SEQUENCE: 58
ttctgttccc tgcaggctct tggtccatta cagcagcatc tgtaggaaga cgtctagatt    60
gatcttgctg gcgc                                                     74

<210> SEQ ID NO 59
<211> LENGTH: 50
<212> TYPE: DNA
<213> ORGANISM: Artificial
<220> FEATURE:
<223> OTHER INFORMATION: probe

<400> SEQUENCE: 59
caygcgtggt cagacccgag tgacccgtct agattggatc ttgctggcac               50
```

<210> SEQ ID NO 60
<211> LENGTH: 70
<212> TYPE: DNA
<213> ORGANISM: Artificial
<220> FEATURE:
<223> OTHER INFORMATION: probe

<400> SEQUENCE: 60
gggttcccta agggttggac yrcacagttg ratcactgcg ttttcacaca gagaaaaatc    60 actcrccctt                                                           70

<210> SEQ ID NO 61
<211> LENGTH: 58
<212> TYPE: DNA
<213> ORGANISM: Artificial
<220> FEATURE:
<223> OTHER INFORMATION: probe

<400> SEQUENCE: 61
gggttcccta agggttggac ctgcagggga cgtgagggta cagttcagat tcaggcaa      58

<210> SEQ ID NO 62
<211> LENGTH: 30
<212> TYPE: DNA
<213> ORGANISM: Artificial
<220> FEATURE:
<223> OTHER INFORMATION: probe

<400> SEQUENCE: 62
cggtctgtga gctgaaggca ggggaaggga                                     30

<210> SEQ ID NO 63
<211> LENGTH: 59
<212> TYPE: DNA
<213> ORGANISM: Artificial
<220> FEATURE:
<223> OTHER INFORMATION: probe

<400> SEQUENCE: 63
atctggtgct ctctctagaa agtcctgcct ctgtggtcta gattggatct tgctggcac     59

<210> SEQ ID NO 64
<211> LENGTH: 58
<212> TYPE: DNA
<213> ORGANISM: Artificial
<220> FEATURE:
<223> OTHER INFORMATION: probe

<400> SEQUENCE: 64
gggttcccta agggttggac ctgcagggga cgtgagggta cagttcagaa tcaggcaa      58

<210> SEQ ID NO 65
<211> LENGTH: 44
<212> TYPE: DNA
<213> ORGANISM: Artificial
<220> FEATURE:
<223> OTHER INFORMATION: probe

<400> SEQUENCE: 65
ttttggagca ccagcgatga aggagaaaga agggaaggat ggta                     44

<210> SEQ ID NO 66
<211> LENGTH: 57
<212> TYPE: DNA

```
<213> ORGANISM: Artificial
<220> FEATURE:
<223> OTHER INFORMATION: probe

<400> SEQUENCE: 66
aagaggatga tggccactga gtacctaatc acagtctaga ttggatcttg ctggcac        57

<210> SEQ ID NO 67
<211> LENGTH: 40
<212> TYPE: DNA
<213> ORGANISM: Artificial
<220> FEATURE:
<223> OTHER INFORMATION: probe

<400> SEQUENCE: 67
gggttcccta agggttggac ccctcahgcc tcgytggaca                            40

<210> SEQ ID NO 68
<211> LENGTH: 51
<212> TYPE: DNA
<213> ORGANISM: Artificial
<220> FEATURE:
<223> OTHER INFORMATION: probe

<400> SEQUENCE: 68
gatccatgat ggggtctcca aggccaattt ctccatyggt cccatgatgc t               51

<210> SEQ ID NO 69
<211> LENGTH: 59
<212> TYPE: DNA
<213> ORGANISM: Artificial
<220> FEATURE:
<223> OTHER INFORMATION: probe

<400> SEQUENCE: 69
tgcccttgca grgacctaca gatgctacgg ttctggtcta gattggatct tgctggcac      59

<210> SEQ ID NO 70
<211> LENGTH: 45
<212> TYPE: DNA
<213> ORGANISM: Artificial
<220> FEATURE:
<223> OTHER INFORMATION: probe

<400> SEQUENCE: 70
gggttcccta agggttggac aaggacccct cacgcctcgt tggac                      45

<210> SEQ ID NO 71
<211> LENGTH: 80
<212> TYPE: DNA
<213> ORGANISM: Artificial
<220> FEATURE:
<223> OTHER INFORMATION: probe

<400> SEQUENCE: 71
gggttcccta agggttggac atgttagcac agattttagg catctcgtgt tcggataaaa     60
atacatgaaa agtctttcac                                                  80

<210> SEQ ID NO 72
<211> LENGTH: 79
<212> TYPE: DNA
<213> ORGANISM: Artificial
<220> FEATURE:
<223> OTHER INFORMATION: probe

<400> SEQUENCE: 72
```
gttagcacag attttaggca tcttgtgttc gggaggttgg atctgagacg tgttgtgagt    60
tggtcatagt gaaggacgt                                                79

<210> SEQ ID NO 73
<211> LENGTH: 70
<212> TYPE: DNA
<213> ORGANISM: Artificial
<220> FEATURE:
<223> OTHER INFORMATION: probe

<400> SEQUENCE: 73
gaggtgccaa ttctagtgag aacaatttcc aggaagccgt gttccggtct agattggatc    60
ttgctggcac                                                          70

<210> SEQ ID NO 74
<211> LENGTH: 53
<212> TYPE: DNA
<213> ORGANISM: Artificial
<220> FEATURE:
<223> OTHER INFORMATION: probe

<400> SEQUENCE: 74
aactgatagg gggagtgagg aacagaaccg tctagattgg atcttgctgg cac           53

<210> SEQ ID NO 75
<211> LENGTH: 74
<212> TYPE: DNA
<213> ORGANISM: Artificial
<220> FEATURE:
<223> OTHER INFORMATION: probe

<400> SEQUENCE: 75
ttctgttccc tgcaggctct tggtccatta cagcagcatc tgtagaagac gtctagattg    60
gatcttgctg gcac                                                     74

<210> SEQ ID NO 76
<211> LENGTH: 54
<212> TYPE: DNA
<213> ORGANISM: Artificial
<220> FEATURE:
<223> OTHER INFORMATION: probe

<400> SEQUENCE: 76
gggttcccta agggttggac aagggtgaga ggcaggtctg tattctctca ccta          54

<210> SEQ ID NO 77
<211> LENGTH: 48
<212> TYPE: DNA
<213> ORGANISM: Artificial
<220> FEATURE:
<223> OTHER INFORMATION: probe

<400> SEQUENCE: 77
cgaccacgat gtccagaggg tcactgggag ccgacaactc atagggta                 48

<210> SEQ ID NO 78
<211> LENGTH: 52
<212> TYPE: DNA
<213> ORGANISM: Artificial
<220> FEATURE:
<223> OTHER INFORMATION: probe

<400> SEQUENCE: 78
agtgagtgac agaaccaaag catctgtagt ctagattgga tcttgctggc ac    52

<210> SEQ ID NO 79
<211> LENGTH: 48
<212> TYPE: DNA
<213> ORGANISM: Artificial
<220> FEATURE:
<223> OTHER INFORMATION: probe

<400> SEQUENCE: 79
cgaccacgat gtccagaggg tcactgggag cygacaactc atagggta    48

<210> SEQ ID NO 80
<211> LENGTH: 75
<212> TYPE: DNA
<213> ORGANISM: Artificial
<220> FEATURE:
<223> OTHER INFORMATION: probe

<400> SEQUENCE: 80
gggttcccta agggttggac tgctgccttg ggccagggac catcctgtct gtgaggaaca    60
cacacctgag tgctg    75

<210> SEQ ID NO 81
<211> LENGTH: 69
<212> TYPE: DNA
<213> ORGANISM: Artificial
<220> FEATURE:
<223> OTHER INFORMATION: probe

<400> SEQUENCE: 81
ccatcctgct tccccacatg gccctgagct ctctggcctc tgcttcgtga gacttacttt    60
ttttgttgc    69

<210> SEQ ID NO 82
<211> LENGTH: 70
<212> TYPE: DNA
<213> ORGANISM: Artificial
<220> FEATURE:
<223> OTHER INFORMATION: probe

<400> SEQUENCE: 82
agcaccagcg atgaaggaga aagaagagga ggaggatgaa gaggatgtct agattggatc    60
ttgctggcac    70

<210> SEQ ID NO 83
<211> LENGTH: 50
<212> TYPE: DNA
<213> ORGANISM: Artificial
<220> FEATURE:
<223> OTHER INFORMATION: probe

<400> SEQUENCE: 83
gggttcccta agggttggac cggccgagca ccccagggtc ctctcttccc    50

<210> SEQ ID NO 84
<211> LENGTH: 50
<212> TYPE: DNA
<213> ORGANISM: Artificial
<220> FEATURE:
<223> OTHER INFORMATION: probe

<400> SEQUENCE: 84
agtttatgag agactccctg acaggacgtc tagattgatc ttgctggcac    50

<210> SEQ ID NO 85
<211> LENGTH: 74
<212> TYPE: DNA
<213> ORGANISM: Artificial
<220> FEATURE:
<223> OTHER INFORMATION: probe

<400> SEQUENCE: 85
gggttcccta agggttggac atgtcctatg atcctagagc cttagctgag gagcttcctg    60
ctgatgatgg agat                                                      74

<210> SEQ ID NO 86
<211> LENGTH: 71
<212> TYPE: DNA
<213> ORGANISM: Artificial
<220> FEATURE:
<223> OTHER INFORMATION: probe

<400> SEQUENCE: 86
aagcatggac agatgcagag agaagacgaa gcttgggtgt gagggaggtc tagattggat    60
cttgctggca c                                                         71

<210> SEQ ID NO 87
<211> LENGTH: 60
<212> TYPE: DNA
<213> ORGANISM: Artificial
<220> FEATURE:
<223> OTHER INFORMATION: probe

<400> SEQUENCE: 87
gggttcccta agggttggac cagggaccta cagatgctac ggttctgtta ctcactcccc    60

<210> SEQ ID NO 88
<211> LENGTH: 65
<212> TYPE: DNA
<213> ORGANISM: Artificial
<220> FEATURE:
<223> OTHER INFORMATION: probe

<400> SEQUENCE: 88
catcagttgt cagctcccag tgaccctctg gacatcgtca tgtctagatt ggatcttgct    60
ggcac                                                                65

<210> SEQ ID NO 89
<211> LENGTH: 47
<212> TYPE: DNA
<213> ORGANISM: Artificial
<220> FEATURE:
<223> OTHER INFORMATION: probe

<400> SEQUENCE: 89
gggttcccta agggttggac atcctgtgcg ctgctgagct gagctcg                  47

<210> SEQ ID NO 90
<211> LENGTH: 50
<212> TYPE: DNA
<213> ORGANISM: Artificial
<220> FEATURE:
<223> OTHER INFORMATION: probe

<400> SEQUENCE: 90
gtcgcggctg cctgtctgct ccggcagtct agattggatc ttgctggcac               50

<210> SEQ ID NO 91
<211> LENGTH: 61
<212> TYPE: DNA
<213> ORGANISM: Artificial
<220> FEATURE:
<223> OTHER INFORMATION: probe

<400> SEQUENCE: 91
gggttcccta agggttggac gctgaggcct ggaaaggaat agagggaggg agtgccacat    60
c                                                                   61

<210> SEQ ID NO 92
<211> LENGTH: 60
<212> TYPE: DNA
<213> ORGANISM: Artificial
<220> FEATURE:
<223> OTHER INFORMATION: probe

<400> SEQUENCE: 92
ctcctctcta aggtggcgcc tccttctccc ccaggtgtct agattggatc ttgctggcac    60

<210> SEQ ID NO 93
<211> LENGTH: 73
<212> TYPE: DNA
<213> ORGANISM: Artificial
<220> FEATURE:
<223> OTHER INFORMATION: probe

<400> SEQUENCE: 93
gggttcccta agggttggac ccgcttagaa agaagaaatg gggagaatct tctgagcaca    60
gggagggagg ggc                                                      73

<210> SEQ ID NO 94
<211> LENGTH: 68
<212> TYPE: DNA
<213> ORGANISM: Artificial
<220> FEATURE:
<223> OTHER INFORMATION: probe

<400> SEQUENCE: 94
agctcaacat actcctctct gaggcggcat ctccttctcc ccaaggtggt caggacaagc    60
ccttctgc                                                            68

<210> SEQ ID NO 95
<211> LENGTH: 77
<212> TYPE: DNA
<213> ORGANISM: Artificial
<220> FEATURE:
<223> OTHER INFORMATION: probe

<400> SEQUENCE: 95
tctgcctggc ccagcgctgt ggtgcctcaa ggaggacacg tgactcttcg gtggtctaga    60
ttggatcttg ctggcac                                                  77

<210> SEQ ID NO 96
<211> LENGTH: 60
<212> TYPE: DNA
<213> ORGANISM: Artificial
<220> FEATURE:
<223> OTHER INFORMATION: probe

<400> SEQUENCE: 96
gggttcccta agggttggac tcagctcagg tatgagggga gctatgacaa ggaagaacct    60

<210> SEQ ID NO 97
<211> LENGTH: 34
<212> TYPE: DNA
<213> ORGANISM: Artificial
<220> FEATURE:
<223> OTHER INFORMATION: probe

<400> SEQUENCE: 97
ccctgaggaa actgcctctt ctccttccag gtcc                                    34

<210> SEQ ID NO 98
<211> LENGTH: 56
<212> TYPE: DNA
<213> ORGANISM: Artificial
<220> FEATURE:
<223> OTHER INFORMATION: probe

<400> SEQUENCE: 98
atatgagaaa ccttctctct cagcccagcc gggtctagat tggatcttgc tggcac            56

<210> SEQ ID NO 99
<211> LENGTH: 54
<212> TYPE: DNA
<213> ORGANISM: Artificial
<220> FEATURE:
<223> OTHER INFORMATION: probe

<400> SEQUENCE: 99
gggttcccta agggttggac cgacctacac atgcttcggc tctctccatg actc              54

<210> SEQ ID NO 100
<211> LENGTH: 54
<212> TYPE: DNA
<213> ORGANISM: Artificial
<220> FEATURE:
<223> OTHER INFORMATION: probe

<400> SEQUENCE: 100
gggttcccta agggttggac cgacctacac atgcttyrgc tctctccatg actc              54

<210> SEQ ID NO 101
<211> LENGTH: 54
<212> TYPE: DNA
<213> ORGANISM: Artificial
<220> FEATURE:
<223> OTHER INFORMATION: probe

<400> SEQUENCE: 101
accctatgag tggtcagacc cgagtgaccc gtctagattg gatcttgctg gcac              54

<210> SEQ ID NO 102
<211> LENGTH: 69
<212> TYPE: DNA
<213> ORGANISM: Artificial
<220> FEATURE:
<223> OTHER INFORMATION: probe

<400> SEQUENCE: 102
gggttcccta agggttggac ggggcgcggc tgcctgtctg caccggcagc accatgtcgc        60
tcatggtca                                                                69

<210> SEQ ID NO 103
<211> LENGTH: 32
<212> TYPE: DNA

```
<213> ORGANISM: Artificial
<220> FEATURE:
<223> OTHER INFORMATION: probe

<400> SEQUENCE: 103
tcagcatggc gtgtgttggt gagtcctgga aa                                32

<210> SEQ ID NO 104
<211> LENGTH: 67
<212> TYPE: DNA
<213> ORGANISM: Artificial
<220> FEATURE:
<223> OTHER INFORMATION: probe

<400> SEQUENCE: 104
tgaccatgag cgacatggtg ctgccggtgc agacgggagg ttggtctaga ttggatcttg   60
ctggcac                                                             67

<210> SEQ ID NO 105
<211> LENGTH: 52
<212> TYPE: DNA
<213> ORGANISM: Artificial
<220> FEATURE:
<223> OTHER INFORMATION: probe

<400> SEQUENCE: 105
gggttcccta agggttggac ggaaagagcc gaagcatctg taggttcctc ct           52

<210> SEQ ID NO 106
<211> LENGTH: 60
<212> TYPE: DNA
<213> ORGANISM: Artificial
<220> FEATURE:
<223> OTHER INFORMATION: probe

<400> SEQUENCE: 106
tgggtggcag ggcccagagg aaagtcggcc tggaatgtct agattggatc ttgctggcac   60

<210> SEQ ID NO 107
<211> LENGTH: 76
<212> TYPE: DNA
<213> ORGANISM: Artificial
<220> FEATURE:
<223> OTHER INFORMATION: probe

<400> SEQUENCE: 107
gggttcccta agggttggac aaggaaggcc tggtttgcct gcagatggat ggtccatcat   60
gatctttctt tccagc                                                   76

<210> SEQ ID NO 108
<211> LENGTH: 65
<212> TYPE: DNA
<213> ORGANISM: Artificial
<220> FEATURE:
<223> OTHER INFORMATION: probe

<400> SEQUENCE: 108
gttcttcttg ctgcagggggg cctggccacr tgagggtaag tgtctagatt ggatcttgct   60
ggcac                                                               65

<210> SEQ ID NO 109
<211> LENGTH: 53
<212> TYPE: DNA
<213> ORGANISM: Artificial
```

```
<220> FEATURE:
<223> OTHER INFORMATION: probe

<400> SEQUENCE: 109
gggttcccta agggttggac acttctttct gcacaragag kggatctcta agg    53

<210> SEQ ID NO 110
<211> LENGTH: 73
<212> TYPE: DNA
<213> ORGANISM: Artificial
<220> FEATURE:
<223> OTHER INFORMATION: probe

<400> SEQUENCE: 110
acccctcacr cctcgttgga cagatccatg atggggtctc caaggccart ttctccatcg    60
gttccatgat gcg    73

<210> SEQ ID NO 111
<211> LENGTH: 69
<212> TYPE: DNA
<213> ORGANISM: Artificial
<220> FEATURE:
<223> OTHER INFORMATION: probe

<400> SEQUENCE: 111
gggttcccta agggttggac agatatcatg tttgagcact tctttctgca caaagagtgg    60
atctctaaa    69

<210> SEQ ID NO 112
<211> LENGTH: 59
<212> TYPE: DNA
<213> ORGANISM: Artificial
<220> FEATURE:
<223> OTHER INFORMATION: probe

<400> SEQUENCE: 112
tgcccttgca gggacctaca gatgctacgg ttctggtcta gattggatct tgctggcac    59

<210> SEQ ID NO 113
<211> LENGTH: 61
<212> TYPE: DNA
<213> ORGANISM: Artificial
<220> FEATURE:
<223> OTHER INFORMATION: probe

<400> SEQUENCE: 113
gggttcccta agggttggac cttgggccca gaggaaagtc rgcctggaat gttccgtkga    60
t    61

<210> SEQ ID NO 114
<211> LENGTH: 42
<212> TYPE: DNA
<213> ORGANISM: Artificial
<220> FEATURE:
<223> OTHER INFORMATION: probe

<400> SEQUENCE: 114
gctgcgcact gcagggagcc tacgttcatg ggcctcccy tc    42

<210> SEQ ID NO 115
<211> LENGTH: 86
<212> TYPE: DNA
<213> ORGANISM: Artificial
<220> FEATURE:
```

<223> OTHER INFORMATION: probe

<400> SEQUENCE: 115
cctggataga tggtacatgt cataggagct ccgggagctg caggacaagg tcacattctc    60
tcgtctagat tggatcttgc tggcac    86

<210> SEQ ID NO 116
<211> LENGTH: 57
<212> TYPE: DNA
<213> ORGANISM: Artificial
<220> FEATURE:
<223> OTHER INFORMATION: probe

<400> SEQUENCE: 116
cctggataga tggagctgca ggacaaggtc acagtctaga ttggatcttg ctggcac    57

<210> SEQ ID NO 117
<211> LENGTH: 49
<212> TYPE: DNA
<213> ORGANISM: Artificial
<220> FEATURE:
<223> OTHER INFORMATION: probe

<400> SEQUENCE: 117
gggttcccta agggttggac taggagaccg tggaaaaggc aattcccga    49

<210> SEQ ID NO 118
<211> LENGTH: 28
<212> TYPE: DNA
<213> ORGANISM: Artificial
<220> FEATURE:
<223> OTHER INFORMATION: probe

<400> SEQUENCE: 118
cccactggtg aaatgtggtg ctgatttt    28

<210> SEQ ID NO 119
<211> LENGTH: 57
<212> TYPE: DNA
<213> ORGANISM: Artificial
<220> FEATURE:
<223> OTHER INFORMATION: probe

<400> SEQUENCE: 119
gacactaagt ggatgaagca gatggatata agcgtctaga ttggatcttg ctggcac    57

<210> SEQ ID NO 120
<211> LENGTH: 69
<212> TYPE: DNA
<213> ORGANISM: Artificial
<220> FEATURE:
<223> OTHER INFORMATION: probe

<400> SEQUENCE: 120
gggttcccta agggttggac ctgaagctcc tcagctatgg ctctaggatc ataagacatg    60
ggacagaca    69

<210> SEQ ID NO 121
<211> LENGTH: 60
<212> TYPE: DNA
<213> ORGANISM: Artificial
<220> FEATURE:
<223> OTHER INFORMATION: probe

<400> SEQUENCE: 121

```
cgggttttcc tcacctgtga cagaaacaag cagtgggtca cttgagtttg accacacgca    60
```

<210> SEQ ID NO 122
<211> LENGTH: 65
<212> TYPE: DNA
<213> ORGANISM: Artificial
<220> FEATURE:
<223> OTHER INFORMATION: probe

<400> SEQUENCE: 122

```
gggcagggca cggaaagagc cgaagcatct gtagttccct cgtctagatt ggatcttgct    60
ggcac                                                                65
```

<210> SEQ ID NO 123
<211> LENGTH: 65
<212> TYPE: DNA
<213> ORGANISM: Artificial
<220> FEATURE:
<223> OTHER INFORMATION: probe

<400> SEQUENCE: 123

```
ggkcayrgca cggaaagagc cgaagcatct gtagktccct cgtctagatt ggatcttgct    60
ggcac                                                                65
```

<210> SEQ ID NO 124
<211> LENGTH: 45
<212> TYPE: DNA
<213> ORGANISM: Artificial
<220> FEATURE:
<223> OTHER INFORMATION: control probe

<400> SEQUENCE: 124

```
gggttcccta agggttggat agagggctcc aggttatccg ggctc                    45
```

<210> SEQ ID NO 125
<211> LENGTH: 45
<212> TYPE: DNA
<213> ORGANISM: Artificial
<220> FEATURE:
<223> OTHER INFORMATION: control probe

<400> SEQUENCE: 125

```
gggttcccta agggttggat agagggctcc aggttatccg ggctc                    45
```

<210> SEQ ID NO 126
<211> LENGTH: 52
<212> TYPE: DNA
<213> ORGANISM: Artificial
<220> FEATURE:
<223> OTHER INFORMATION: control probe

<400> SEQUENCE: 126

```
gggttcccta agggttggat tcaggagtga tacttcacag atcctggagg aa            52
```

<210> SEQ ID NO 127
<211> LENGTH: 52
<212> TYPE: DNA
<213> ORGANISM: Artificial
<220> FEATURE:
<223> OTHER INFORMATION: control probe

<400> SEQUENCE: 127

```
aacatcccag tccttaaggc caaactgagt ctagattgga tcttgctggc ac            52
```

<210> SEQ ID NO 128
<211> LENGTH: 58
<212> TYPE: DNA
<213> ORGANISM: Artificial
<220> FEATURE:
<223> OTHER INFORMATION: control probe

<400> SEQUENCE: 128
gggttcccta agggttggac tgcgtgagac caagcgccgt catgagaccc gactggtg            58

<210> SEQ ID NO 129
<211> LENGTH: 58
<212> TYPE: DNA
<213> ORGANISM: Artificial
<220> FEATURE:
<223> OTHER INFORMATION: control probe

<400> SEQUENCE: 129
gagattgaca atgggaagca gcgtgagttt gagagtctag attggatctt gctggcac            58

<210> SEQ ID NO 130
<211> LENGTH: 44
<212> TYPE: DNA
<213> ORGANISM: Artificial
<220> FEATURE:
<223> OTHER INFORMATION: control probe

<400> SEQUENCE: 130
gggttcccta agggttggac caggcgttct cagcctccgg atga            44

<210> SEQ ID NO 131
<211> LENGTH: 41
<212> TYPE: DNA
<213> ORGANISM: Artificial
<220> FEATURE:
<223> OTHER INFORMATION: control probe

<400> SEQUENCE: 131
cacaaatacc agagcacaga ttcaagtgca atccatgtat c            41

<210> SEQ ID NO 132
<211> LENGTH: 45
<212> TYPE: DNA
<213> ORGANISM: Artificial
<220> FEATURE:
<223> OTHER INFORMATION: control probe

<400> SEQUENCE: 132
tgtatgggtc attctcacct ggtctagatt ggatcttgct ggcac            45

<210> SEQ ID NO 133
<211> LENGTH: 60
<212> TYPE: DNA
<213> ORGANISM: Artificial
<220> FEATURE:
<223> OTHER INFORMATION: control probe

<400> SEQUENCE: 133
gggttcccta agggttggac gcaggacaga aggagcaagc tgtggaatgg tataagaaag            60

<210> SEQ ID NO 134
<211> LENGTH: 60
<212> TYPE: DNA
<213> ORGANISM: Artificial
<220> FEATURE:
<223> OTHER INFORMATION: control probe

<400> SEQUENCE: 134
gtattgaaga actggaagaa ggaatagctg ttatagttac aggacaaggt aagattgtat    60

<210> SEQ ID NO 135
<211> LENGTH: 60
<212> TYPE: DNA
<213> ORGANISM: Artificial
<220> FEATURE:
<223> OTHER INFORMATION: control probe

<400> SEQUENCE: 135
ttgtttatag ccatcccaaa ttatgatata ttcacactct agattggatc ttgctggcac    60

<210> SEQ ID NO 136
<211> LENGTH: 58
<212> TYPE: DNA
<213> ORGANISM: Artificial
<220> FEATURE:
<223> OTHER INFORMATION: control probe

<400> SEQUENCE: 136
gggttcccta agggttggac ctgctcccag tagggtcagc atctggaccc caggctga      58

<210> SEQ ID NO 137
<211> LENGTH: 59
<212> TYPE: DNA
<213> ORGANISM: Artificial
<220> FEATURE:
<223> OTHER INFORMATION: control probe

<400> SEQUENCE: 137
gagtcaggct ctgattccag atctagcctc catcatgaag aagctcttga ccaagtatg     59

<210> SEQ ID NO 138
<211> LENGTH: 58
<212> TYPE: DNA
<213> ORGANISM: Artificial
<220> FEATURE:
<223> OTHER INFORMATION: control probe

<400> SEQUENCE: 138
acaacctctt tgagacgtcc tttccctact ccatgtctag attggatctt gctggcac      58

<210> SEQ ID NO 139
<211> LENGTH: 60
<212> TYPE: DNA
<213> ORGANISM: Artificial
<220> FEATURE:
<223> OTHER INFORMATION: control probe

<400> SEQUENCE: 139
gggttcccta agggttggac gcaggacaga aggagcaagc tgtggaatgg tataagaaag    60

<210> SEQ ID NO 140
<211> LENGTH: 60
<212> TYPE: DNA
<213> ORGANISM: Artificial
<220> FEATURE:
<223> OTHER INFORMATION: control probe

<400> SEQUENCE: 140
gtattgaaga actggaagaa ggaatagctg ttatagttac aggacaaggt aagattgtat    60

<210> SEQ ID NO 141

```
<211> LENGTH: 60
<212> TYPE: DNA
<213> ORGANISM: Artificial
<220> FEATURE:
<223> OTHER INFORMATION: control probe

<400> SEQUENCE: 141
ttgtttatag ccatcccaaa ttatgatata ttcacactct agattggatc ttgctggcac    60

<210> SEQ ID NO 142
<211> LENGTH: 73
<212> TYPE: DNA
<213> ORGANISM: Artificial
<220> FEATURE:
<223> OTHER INFORMATION: control probe

<400> SEQUENCE: 142
gggttcccta agggttggac cagccagcag cagccccaag ctgataagat taatctaaag    60
agcaaattat ggt                                                      73

<210> SEQ ID NO 143
<211> LENGTH: 69
<212> TYPE: DNA
<213> ORGANISM: Artificial
<220> FEATURE:
<223> OTHER INFORMATION: control probe

<400> SEQUENCE: 143
gtaatttcct atgctgaaac tttgtagtta attttttaaa aaggtttcat tttcctattg    60
gtctgattt                                                           69

<210> SEQ ID NO 144
<211> LENGTH: 66
<212> TYPE: DNA
<213> ORGANISM: Artificial
<220> FEATURE:
<223> OTHER INFORMATION: control probe

<400> SEQUENCE: 144
cacaggaaca ttttacctgt ttgtgaggca ttttttctcc tggtctagat tggatcttgc    60
tggcac                                                              66

<210> SEQ ID NO 145
<211> LENGTH: 73
<212> TYPE: DNA
<213> ORGANISM: Artificial
<220> FEATURE:
<223> OTHER INFORMATION: control probe

<400> SEQUENCE: 145
gggttcccta agggttggac cagccagcag cagccccaag ctgataagat taatctaaag    60
agcaaattat ggt                                                      73

<210> SEQ ID NO 146
<211> LENGTH: 69
<212> TYPE: DNA
<213> ORGANISM: Artificial
<220> FEATURE:
<223> OTHER INFORMATION: control probe

<400> SEQUENCE: 146
gtaatttcct atgctgaaac tttgtagtta attttttaaa aaggtttcat tttcctattg    60
gtctgattt                                                           69
```

```
<210> SEQ ID NO 147
<211> LENGTH: 66
<212> TYPE: DNA
<213> ORGANISM: Artificial
<220> FEATURE:
<223> OTHER INFORMATION: control probe

<400> SEQUENCE: 147
cacaggaaca ttttacctgt ttgtgaggca ttttttctcc tggtctagat tggatcttgc    60
tggcac                                                               66

<210> SEQ ID NO 148
<211> LENGTH: 65
<212> TYPE: DNA
<213> ORGANISM: Artificial
<220> FEATURE:
<223> OTHER INFORMATION: control probe

<400> SEQUENCE: 148
gggttcccta agggttggac cccttaatc caaagtgctg ctcaacaaga gttcgaagac     60
aactg                                                                65

<210> SEQ ID NO 149
<211> LENGTH: 69
<212> TYPE: DNA
<213> ORGANISM: Artificial
<220> FEATURE:
<223> OTHER INFORMATION: control probe

<400> SEQUENCE: 149
gacaggaatc tcacctttca taaaatggtg gcatggatga ttgcactcta gattggatct    60
tgctggcac                                                            69

<210> SEQ ID NO 150
<211> LENGTH: 57
<212> TYPE: DNA
<213> ORGANISM: Artificial
<220> FEATURE:
<223> OTHER INFORMATION: control probe

<400> SEQUENCE: 150
gggttcccta agggttggac accctttac actgacatcc gccctgagg aagactt         57

<210> SEQ ID NO 151
<211> LENGTH: 56
<212> TYPE: DNA
<213> ORGANISM: Artificial
<220> FEATURE:
<223> OTHER INFORMATION: control probe

<400> SEQUENCE: 151
ctttagtatc catatccgca tcgttgggga ctggacagag ggctgttca atgctt          56

<210> SEQ ID NO 152
<211> LENGTH: 57
<212> TYPE: DNA
<213> ORGANISM: Artificial
<220> FEATURE:
<223> OTHER INFORMATION: control probe

<400> SEQUENCE: 152
gtggctgtga taagcaggag tttcaagatg cgtgtctaga ttggatcttg ctggcac        57
```

```
<210> SEQ ID NO 153
<211> LENGTH: 19
<212> TYPE: DNA
<213> ORGANISM: Artificial
<220> FEATURE:
<223> OTHER INFORMATION: short left probe KIR3DL1 WT

<400> SEQUENCE: 153
gcctggttgg acagatcca                                                  19

<210> SEQ ID NO 154
<211> LENGTH: 36
<212> TYPE: DNA
<213> ORGANISM: Artificial
<220> FEATURE:
<223> OTHER INFORMATION: long left probe KIR3DL1 WT

<400> SEQUENCE: 154
ctctaaggac ccctcacgcc tcgttggaca gatcca                                36

<210> SEQ ID NO 155
<211> LENGTH: 18
<212> TYPE: DNA
<213> ORGANISM: Artificial
<220> FEATURE:
<223> OTHER INFORMATION: short left probe KIR3DL1 1*024N

<400> SEQUENCE: 155
gcctggttgg acgatcca                                                   18

<210> SEQ ID NO 156
<211> LENGTH: 35
<212> TYPE: DNA
<213> ORGANISM: Artificial
<220> FEATURE:
<223> OTHER INFORMATION: long left probe KIR3DL1 1*024N

<400> SEQUENCE: 156
ctctaaggac ccctcacgcc tcgttggacg atcca                                 35

<210> SEQ ID NO 157
<211> LENGTH: 24
<212> TYPE: DNA
<213> ORGANISM: Artificial
<220> FEATURE:
<223> OTHER INFORMATION: short right probe KIR3DL1 WT

<400> SEQUENCE: 157
cccatgatgc ttgcccttgc agrg                                            24

<210> SEQ ID NO 158
<211> LENGTH: 44
<212> TYPE: DNA
<213> ORGANISM: Artificial
<220> FEATURE:
<223> OTHER INFORMATION: long right probe KIR3DL1 WT

<400> SEQUENCE: 158
cccatgatgc ttgcccttgc agrgacctac agatgctacg gttc                      44

<210> SEQ ID NO 159
<211> LENGTH: 66
<212> TYPE: DNA
<213> ORGANISM: Artificial Sequence
<220> FEATURE:
<223> OTHER INFORMATION: probe
```

```
<400> SEQUENCE: 159
gggttcccta agggttggac cgatggcagg gcccagagga aagtcggcct ggaatgttcc      60
gttgat                                                                66

<210> SEQ ID NO 160
<211> LENGTH: 71
<212> TYPE: DNA
<213> ORGANISM: Artificial Sequence
<220> FEATURE:
<223> OTHER INFORMATION: probe

<400> SEQUENCE: 160
gctgcgcact gcagggagcc tacgttcatg ggcctcccct tcccttggtc tagattggat      60
cttgctggca c                                                          71

<210> SEQ ID NO 161
<211> LENGTH: 66
<212> TYPE: DNA
<213> ORGANISM: Artificial Sequence
<220> FEATURE:
<223> OTHER INFORMATION: probe

<400> SEQUENCE: 161
gggttcccta agggttggac ctctccagcc aggatgatcc atccccgcac tccctccctc      60
tattcc                                                                66

<210> SEQ ID NO 162
<211> LENGTH: 32
<212> TYPE: DNA
<213> ORGANISM: Artificial Sequence
<220> FEATURE:
<223> OTHER INFORMATION: probe

<400> SEQUENCE: 162
tttccaggac tcaccaacac acgccatgct ga                                   32

<210> SEQ ID NO 163
<211> LENGTH: 44
<212> TYPE: DNA
<213> ORGANISM: Artificial Sequence
<220> FEATURE:
<223> OTHER INFORMATION: long right probe KIR3DL1 1*024N

<400> SEQUENCE: 163
cccatgatgc ttgcccttgc agggacctac agatgctacg gttc                      44
```